US009194870B2

(12) United States Patent
Mehra et al.

(10) Patent No.: US 9,194,870 B2
(45) Date of Patent: Nov. 24, 2015

(54) **PEPTIDES, DEVICES, AND METHODS FOR THE DETECTION OF *ANAPLASMA* ANTIBODIES**

(71) Applicant: Abaxis, Inc., Union City, CA (US)

(72) Inventors: Rajesh K. Mehra, Hayward, CA (US); Kenneth P. Aron, San Francisco, CA (US); Dennis M. Bleile, San Ramon, CA (US); Andrew P. Rogers, Union City, CA (US); Timothy P. Forsyth, Hayward, CA (US); Jeremy D. Walker, Castro Valley, CA (US); Christina R. Cuesico, Fremont, CA (US)

(73) Assignee: ABAXIS, INC., Union City, CA (US)

( * ) Notice: Subject to any disclaimer, the term of this patent is extended or adjusted under 35 U.S.C. 154(b) by 0 days.

(21) Appl. No.: 14/511,916

(22) Filed: Oct. 10, 2014

(65) Prior Publication Data

US 2015/0204868 A1 Jul. 23, 2015

Related U.S. Application Data

(60) Provisional application No. 61/929,655, filed on Jan. 21, 2014.

(51) Int. Cl.
*C07K 14/195* (2006.01)
*G01N 33/569* (2006.01)

(52) U.S. Cl.
CPC ........ *G01N 33/56911* (2013.01); *C07K 14/195* (2013.01); *G01N 2333/29* (2013.01); *G01N 2469/20* (2013.01)

(58) Field of Classification Search
CPC ..... C07K 14/00; A61K 38/00; A61K 39/0233
See application file for complete search history.

(56) References Cited

U.S. PATENT DOCUMENTS

| 5,618,533 | A | 4/1997 | Flavell et al. |
|---|---|---|---|
| 5,643,733 | A | 7/1997 | Robinson et al. |
| 5,643,751 | A | 7/1997 | Robinson et al. |
| 5,932,220 | A | 8/1999 | Barbour et al. |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,306,394 | B1 | 10/2001 | Murphy et al. |
| 6,306,402 | B1 | 10/2001 | Reed et al. |
| 6,355,777 | B1 | 3/2002 | Walker et al. |
| 6,403,093 | B1 | 6/2002 | Persing et al. |
| 6,436,399 | B1 | 8/2002 | Rikihisa et al. |
| 6,607,728 | B2 | 8/2003 | Reed et al. |
| 6,617,441 | B1 | 9/2003 | Barbour et al. |
| 6,716,574 | B2 | 4/2004 | Mathiesen et al. |
| 6,964,855 | B2 | 11/2005 | O'Connor, Jr. et al. |
| 7,204,992 | B2 | 4/2007 | McBride et al. |
| 7,304,139 | B2 | 12/2007 | Alleman et al. |
| 7,390,626 | B2 | 6/2008 | Vojdani |
| 7,407,770 | B2 | 8/2008 | O'Connor, Jr. |
| 7,439,321 | B2 | 10/2008 | O'Connor et al. |
| 7,507,789 | B2 | 3/2009 | Beall et al. |
| 7,696,310 | B2 | 4/2010 | O'Connor, Jr. et al. |
| 7,887,815 | B2 | 2/2011 | Dattwyler et al. |
| 7,906,296 | B2 | 3/2011 | Beall et al. |
| 7,989,170 | B2 | 8/2011 | Fernandez et al. |
| 8,093,008 | B2 | 1/2012 | Murphy et al. |
| 8,158,370 | B2 | 4/2012 | Liu et al. |
| 8,257,938 | B2 | 9/2012 | Hoey et al. |
| 8,303,959 | B2 | 11/2012 | Liu et al. |
| 8,318,915 | B2 | 11/2012 | Fernandez et al. |
| 8,435,495 | B2 | 5/2013 | Murphy et al. |
| 8,455,211 | B2 | 6/2013 | Dimitrov et al. |
| 8,568,989 | B2 | 10/2013 | Mehra et al. |
| 8,758,772 | B2 | 6/2014 | Mehra et al. |
| 2011/0124125 | A1 | 5/2011 | Mehra et al. |
| 2012/0207779 | A1 | 8/2012 | Liu et al. |
| 2013/0064842 | A1 | 3/2013 | Liu et al. |
| 2013/0115634 | A1 | 5/2013 | Mehra et al. |
| 2014/0121125 | A1 | 5/2014 | Mehra et al. |

FOREIGN PATENT DOCUMENTS

| EP | 1026949 | 9/2010 |
|---|---|---|
| EP | 1576350 | 3/2013 |
| WO | WO 2006/138509 | 12/2006 |
| WO | WO 2008/137881 | 11/2008 |
| WO | WO 2012/135701 | 10/2012 |

OTHER PUBLICATIONS

Outer membrane protein.1x [*Anaplasma platys*]; GenBank: AEH96269.1; Jun. 19, 2011; pp. 1-2.*
GenBank Accession No. AAO30097.1, major surface protein 2 [*Anaplasma phagocytophilum*], Mar. 26, 2003.
GenBank Accession No. ACV85580.1, P44 major outer membrane protein, partial [*Anaplasma phagocytophilum*], Nov. 13, 2009.
GenBank Accession No. ACV85559.1, P44 major outer membrane protein, partial [*Anaplasma phagocytophilum*], Nov. 13, 1999.
GenBank Accession No. AEH96270.1, outer membrane protein, partial [*Anaplasma platys*], Jun. 19, 2011.

(Continued)

*Primary Examiner* — Karlheinz R Skowronek
*Assistant Examiner* — Lianko Garyu
(74) *Attorney, Agent, or Firm* — Cooley LLP

(57) ABSTRACT

The invention provides populations of isolated peptides useful for the detection of antibodies that bind to *Anaplasma* antigens. The peptide populations comprise peptides derived from immunogenic fragments of the *Anaplasma* Outer Membrane Protein proteins. The invention also provides devices, methods, and kits comprising the populations of isolated peptides useful for the detection of antibodies that bind to *Anaplasma* antigens and the diagnosis of anaplasmosis. Methods of identifying the particular *Anaplasma* species infecting a subject using the peptide populations of the invention are also disclosed.

17 Claims, 8 Drawing Sheets

(56) References Cited

OTHER PUBLICATIONS

GenBank Accession No. ADU56850.1, P44 outer membrane protein [*Anaplasma platys*], Jun. 18, 2011.
GenBank Accession No. AAQ91849.1, major surface protein, partial [*Anaplasma phagocytophilum*], Oct. 8, 2003.
Kahlon, A. et al., "*Anaplasma phagocytophilum* Asp14 is an invasin that interacts with mammalian host cells via its C terminus to facilitate infection," Infect. Immun., 81(1): 65-79 (2013).
Zhi, N. et al., "Comparison of major antigenic proteins of six strains of the human granulocytic ehrlichiosis agent by Western immunoblot analysis," J. Clin. Microbiol., 35(10): 2606-2611 (1997).

* cited by examiner

```
                          SEQUENCE LISTING

<160> NUMBER OF SEQ ID NOS: 543

<210> SEQ ID NO 1
<211> LENGTH: 36
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (9)..(9)
<223> OTHER INFORMATION: Xaa is Ile, Pro or His
<220> FEATURE:
<221> NAME/KEY: MISC_FEATURE
<222> LOCATION: (17)..(17)
<223> OTHER INFORMATION: Xaa is Ile, Trp or Tyr
<220> FEATURE:
<221> NAME/KEY: MISC_FEATURE
<222> LOCATION: (21)..(21)
<223> OTHER INFORMATION: Xaa is Arg, Asp or Asn
<220> FEATURE:
<221> NAME/KEY: MISC_FEATURE
<222> LOCATION: (28)..(28)
<223> OTHER INFORMATION: Xaa is Glu or Asn
<220> FEATURE:
<221> NAME/KEY: MISC_FEATURE
<222> LOCATION: (31)..(31)
<223> OTHER INFORMATION: Xaa is Leu of Val

<400> SEQUENCE: 1

Glu Thr Arg Val Ala Tyr Pro Tyr Xaa Lys Asp Gly Arg Thr Val Lys
1               5                   10                  15

Xaa Asp Ser His Xaa Phe Asp Trp Gln Thr Pro Xaa Pro Lys Xaa Gly
                20                  25                  30

Phe Lys Asp Cys
                35

<210> SEQ ID NO 2
<211> LENGTH: 21
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (3)..(3)
<223> OTHER INFORMATION: Xaa is Leu, Val or Ala
<220> FEATURE:
<221> NAME/KEY: MISC_FEATURE
<222> LOCATION: (7)..(7)
<223> OTHER INFORMATION: Xaa is Lys, Asn or Gln
<220> FEATURE:
<221> NAME/KEY: MISC_FEATURE
<222> LOCATION: (11)..(11)
<223> OTHER INFORMATION: Xaa is Arg, Asp or Asn
<220> FEATURE:
<221> NAME/KEY: MISC_FEATURE
<222> LOCATION: (15)..(15)
<223> OTHER INFORMATION: Xaa is Glu, Asn or Gln

<400> SEQUENCE: 2
```

```
Ile Glu Xaa Gly Tyr Glu Xaa Phe Lys Thr Xaa Gly Ile Arg Xaa Ser
1               5                   10                  15

Gly Thr Lys Glu Cys
            20

<210> SEQ ID NO 3
<211> LENGTH: 67
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (5)..(5)
<223> OTHER INFORMATION: Xaa is Val or Ala
<220> FEATURE:
<221> NAME/KEY: MISC_FEATURE
<222> LOCATION: (7)..(7)
<223> OTHER INFORMATION: Xaa is Gly, Ile or His
<220> FEATURE:
<221> NAME/KEY: MISC_FEATURE
<222> LOCATION: (11)..(11)
<223> OTHER INFORMATION: Xaa is Glu, Asn or Gln
<220> FEATURE:
<221> NAME/KEY: MISC_FEATURE
<222> LOCATION: (18)..(18)
<223> OTHER INFORMATION: Xaa is Asp or Asn
<220> FEATURE:
<221> NAME/KEY: MISC_FEATURE
<222> LOCATION: (21)..(21)
<223> OTHER INFORMATION: Xaa is Arg, Asp or Asn
<220> FEATURE:
<221> NAME/KEY: MISC_FEATURE
<222> LOCATION: (25)..(25)
<223> OTHER INFORMATION: Xaa is Gln, Asp or Glu
<220> FEATURE:
<221> NAME/KEY: MISC_FEATURE
<222> LOCATION: (28)..(28)
<223> OTHER INFORMATION: Xaa is Glu or Asn
<220> FEATURE:
<221> NAME/KEY: MISC_FEATURE
<222> LOCATION: (31)..(31)
<223> OTHER INFORMATION: Xaa is Leu or Val
<220> FEATURE:
<221> NAME/KEY: MISC_FEATURE
<222> LOCATION: (45)..(45)
<223> OTHER INFORMATION: Xaa is Lys or Gln
<220> FEATURE:
<221> NAME/KEY: MISC_FEATURE
<222> LOCATION: (48)..(48)
<223> OTHER INFORMATION: Xaa is Phe or Val
<220> FEATURE:
<221> NAME/KEY: MISC_FEATURE
<222> LOCATION: (51)..(51)
<223> OTHER INFORMATION: Xaa is Asp or Asn
<220> FEATURE:
<221> NAME/KEY: MISC_FEATURE
<222> LOCATION: (54)..(54)
<223> OTHER INFORMATION: Xaa is Glu or Gln
<220> FEATURE:
<221> NAME/KEY: MISC_FEATURE
<222> LOCATION: (57)..(57)
<223> OTHER INFORMATION: Xaa is Ser or Gln
<220> FEATURE:
<221> NAME/KEY: MISC_FEATURE
<222> LOCATION: (60)..(60)
<223> OTHER INFORMATION: Xaa is Phe or Trp
<220> FEATURE:
<221> NAME/KEY: MISC_FEATURE
<222> LOCATION: (63)..(63)
<223> OTHER INFORMATION: Xaa is Ile or Val
<220> FEATURE:
<221> NAME/KEY: MISC_FEATURE
<222> LOCATION: (66)..(66)
<223> OTHER INFORMATION: Xaa is Gln or Asp
```

<400> SEQUENCE: 3

Glu Thr Lys Val Xaa Tyr Xaa Tyr Leu Lys Xaa Gly Arg Thr Val Lys
1               5                   10                  15

Leu Xaa Ser His Xaa Phe Asp Trp Xaa Thr Pro Xaa Pro Lys Xaa Gly
            20                  25                  30

Phe Lys Asp Gly Gly Gly Gly Lys Asp Gly Thr Xaa Val Glu Xaa
        35                  40                  45

Lys Ala Xaa Lys Phe Xaa Trp Asn Xaa Pro Asp Xaa Arg Ile Xaa Phe
50                  55                  60

Lys Xaa Cys
65

<210> SEQ ID NO 4
<211> LENGTH: 27
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (6)..(6)
<223> OTHER INFORMATION: Xaa is Lys or Gln
<220> FEATURE:
<221> NAME/KEY: MISC_FEATURE
<222> LOCATION: (9)..(9)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Asp or Asn
<220> FEATURE:
<221> NAME/KEY: MISC_FEATURE
<222> LOCATION: (15)..(15)
<223> OTHER INFORMATION: Xaa is Glu or Gln
<220> FEATURE:
<221> NAME/KEY: MISC_FEATURE
<222> LOCATION: (18)..(18)
<223> OTHER INFORMATION: Xaa is Ser or Gln
<220> FEATURE:
<221> NAME/KEY: MISC_FEATURE
<222> LOCATION: (21)..(21)
<223> OTHER INFORMATION: Xaa is Phe or Trp
<220> FEATURE:
<221> NAME/KEY: MISC_FEATURE
<222> LOCATION: (24)..(24)
<223> OTHER INFORMATION: Xaa is Ile or Val
<220> FEATURE:
<221> NAME/KEY: MISC_FEATURE
<222> LOCATION: (27)..(27)
<223> OTHER INFORMATION: Xaa is Gln or Asp

<400> SEQUENCE: 4

Cys Lys Asp Gly Thr Xaa Val Glu Xaa Lys Ala Xaa Lys Phe Xaa Trp
1               5                   10                  15

Asn Xaa Pro Asp Xaa Arg Ile Xaa Phe Lys Xaa
            20                  25

<210> SEQ ID NO 5
<211> LENGTH: 40
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (2)..(2)
<223> OTHER INFORMATION: Xaa is Ile or Val
<220> FEATURE:
<221> NAME/KEY: MISC_FEATURE
<222> LOCATION: (10)..(10)

```
<223> OTHER INFORMATION: Xaa is Ser or Tyr
<220> FEATURE:
<221> NAME/KEY: MISC_FEATURE
<222> LOCATION: (23)..(23)
<223> OTHER INFORMATION: Xaa is Glu or Asn

<400> SEQUENCE: 5

Cys Xaa Gly Gly Lys Ser Pro Ala Arg Xaa Thr Glu Glu Arg Val Ala
1               5                   10                  15

Gly Asp Leu Asp His Lys Xaa Val Asp Ser Asp Lys Lys His Asp Ala
            20                  25                  30

Glu Lys Thr Glu Glu Lys Arg His
        35                  40

<210> SEQ ID NO 6
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 6

Cys Gly Lys Ile Leu Asn Leu Val Ser Ala Val Gln Glu Lys Lys Pro
1               5                   10                  15

Pro Glu Ala Pro Ala Ala Asp Glu Ala Ala Gly Pro Ala Thr His
            20                  25                  30

<210> SEQ ID NO 7
<211> LENGTH: 27
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (5)..(5)
<223> OTHER INFORMATION: Xaa is Ser or Gln
<220> FEATURE:
<221> NAME/KEY: MISC_FEATURE
<222> LOCATION: (9)..(9)
<223> OTHER INFORMATION: Xaa is Phe or Tyr
<220> FEATURE:
<221> NAME/KEY: MISC_FEATURE
<222> LOCATION: (13)..(13)
<223> OTHER INFORMATION: Xaa is Arg or His
<220> FEATURE:
<221> NAME/KEY: MISC_FEATURE
<222> LOCATION: (16)..(16)
<223> OTHER INFORMATION: Xaa is Trp or Tyr
<220> FEATURE:
<221> NAME/KEY: MISC_FEATURE
<222> LOCATION: (18)..(18)
<223> OTHER INFORMATION: Xaa is Ser or Gln
<220> FEATURE:
<221> NAME/KEY: MISC_FEATURE
<222> LOCATION: (22)..(22)
<223> OTHER INFORMATION: Xaa is Lys or His
<220> FEATURE:
<221> NAME/KEY: MISC_FEATURE
<222> LOCATION: (27)..(27)
<223> OTHER INFORMATION: Xaa is Asn or Asp

<400> SEQUENCE: 7

Cys Lys Asp Gly Xaa Arg Val Glu Xaa Lys Ala Glu Xaa Phe Asn Xaa
1               5                   10                  15

Gln Xaa Pro Asn Pro Xaa Ile Lys Tyr Arg Xaa
            20                  25

<210> SEQ ID NO 8
```

```
<211> LENGTH: 31
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (10)..(10)
<223> OTHER INFORMATION: Xaa is Val, Leu or Ile
<220> FEATURE:
<221> NAME/KEY: MISC_FEATURE
<222> LOCATION: (11)..(11)
<223> OTHER INFORMATION: Xaa is Ala or Leu

<400> SEQUENCE: 8

Cys Gly Lys Ile Leu Asn Leu Val Ser Xaa Xaa Asn Glu Lys Lys Pro
 1               5                  10                  15

Pro Glu Ala Pro Ala Ala Asp Glu Ala Ala Gly Pro Ala Thr His

-continued

```
Glu Thr Arg Val Ala Tyr Pro Tyr Ile Lys Asp Gly Arg Thr Val Lys
1               5                   10                  15

Ile Asp Ser His Arg Phe Asp Trp Gln Thr Pro Glu Pro Lys Leu Gly
            20                  25                  30

Phe Lys Asp Cys
        35

<210> SEQ ID NO 11
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 11

Glu Thr Arg Val Ala Tyr Pro Tyr Pro Lys Asp Gly Arg Thr Val Lys
1               5                   10                  15

Ile Asp Ser His Arg Phe Asp Trp Gln Thr Pro Glu Pro Lys Leu Gly
            20                  25                  30

Phe Lys Asp Cys
        35

<210> SEQ ID NO 12
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 12

Glu Thr Arg Val Ala Tyr Pro Tyr His Lys Asp Gly Arg Thr Val Lys
1               5                   10                  15

Ile Asp Ser His Arg Phe Asp Trp Gln Thr Pro Glu Pro Lys Leu Gly
            20                  25                  30

Phe Lys Asp Cys
        35

<210> SEQ ID NO 13
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 13

Glu Thr Arg Val Ala Tyr Pro Tyr Ile Lys Asp Gly Arg Thr Val Lys
1               5                   10                  15

Trp Asp Ser His Arg Phe Asp Trp Gln Thr Pro Glu Pro Lys Leu Gly
            20                  25                  30

Phe Lys Asp Cys
        35

<210> SEQ ID NO 14
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 14

Glu Thr Arg Val Ala Tyr Pro Tyr Ile Lys Asp Gly Arg Thr Val Lys
1               5                   10                  15
```

```
Tyr Asp Ser His Arg Phe Asp Trp Gln Thr Pro Glu Pro Lys Leu Gly
            20                  25                  30

Phe Lys Asp Cys
        35

<210> SEQ ID NO 15
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 15

Glu Thr Arg Val Ala Tyr Pro Tyr Pro Lys Asp Gly Arg Thr Val Lys
1               5                   10                  15

Trp Asp Ser His Arg Phe Asp Trp Gln Thr Pro Glu Pro Lys Leu Gly
            20                  25                  30

Phe Lys Asp Cys
        35

<210> SEQ ID NO 16
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 16

Glu Thr Arg Val Ala Tyr Pro Tyr Pro Lys Asp Gly Arg Thr Val Lys
1               5                   10                  15

Tyr Asp Ser His Arg Phe Asp Trp Gln Thr Pro Glu Pro Lys Leu Gly
            20                  25                  30

Phe Lys Asp Cys
        35

<210> SEQ ID NO 17
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 17

Glu Thr Arg Val Ala Tyr Pro Tyr His Lys Asp Gly Arg Thr Val Lys
1               5                   10                  15

Trp Asp Ser His Arg Phe Asp Trp Gln Thr Pro Glu Pro Lys Leu Gly
            20                  25                  30

Phe Lys Asp Cys
        35

<210> SEQ ID NO 18
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 18

Glu Thr Arg Val Ala Tyr Pro Tyr His Lys Asp Gly Arg Thr Val Lys
1               5                   10                  15

Tyr Asp Ser His Arg Phe Asp Trp Gln Thr Pro Glu Pro Lys Leu Gly
            20                  25                  30
```

Phe Lys Asp Cys
        35

<210> SEQ ID NO 19
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 19

Glu Thr Arg Val Ala Tyr Pro Tyr Ile Lys Asp Gly Arg Thr Val Lys
1               5                   10                  15

Ile Asp Ser His Asp Phe Asp Trp Gln Thr Pro Glu Pro Lys Leu Gly
            20                  25                  30

Phe Lys Asp Cys
        35

<210> SEQ ID NO 20
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 20

Glu Thr Arg Val Ala Tyr Pro Tyr Ile Lys Asp Gly Arg Thr Val Lys
1               5                   10                  15

Trp Asp Ser His Asp Phe Asp Trp Gln Thr Pro Glu Pro Lys Leu Gly
            20                  25                  30

Phe Lys Asp Cys
        35

<210> SEQ ID NO 21
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 21

Glu Thr Arg Val Ala Tyr Pro Tyr Ile Lys Asp Gly Arg Thr Val Lys
1               5                   10                  15

Tyr Asp Ser His Asp Phe Asp Trp Gln Thr Pro Glu Pro Lys Leu Gly
            20                  25                  30

Phe Lys Asp Cys
        35

<210> SEQ ID NO 22
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 22

Glu Thr Arg Val Ala Tyr Pro Tyr Pro Lys Asp Gly Arg Thr Val Lys
1               5                   10                  15

Ile Asp Ser His Asp Phe Asp Trp Gln Thr Pro Glu Pro Lys Leu Gly
            20                  25                  30

Phe Lys Asp Cys
        35

<210> SEQ ID NO 23
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 23

Glu Thr Arg Val Ala Tyr Pro Tyr Pro Lys Asp Gly Arg Thr Val Lys
1               5                   10                  15

Trp Asp Ser His Asp Phe Asp Trp Gln Thr Pro Glu Pro Lys Leu Gly
            20                  25                  30

Phe Lys Asp Cys
        35

<210> SEQ ID NO 24
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 24

Glu Thr Arg Val Ala Tyr Pro Tyr Pro Lys Asp Gly Arg Thr Val Lys
1               5                   10                  15

Tyr Asp Ser His Asp Phe Asp Trp Gln Thr Pro Glu Pro Lys Leu Gly
            20                  25                  30

Phe Lys Asp Cys
        35

<210> SEQ ID NO 25
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 25

Glu Thr Arg Val Ala Tyr Pro Tyr His Lys Asp Gly Arg Thr Val Lys
1               5                   10                  15

Ile Asp Ser His Asp Phe Asp Trp Gln Thr Pro Glu Pro Lys Leu Gly
            20                  25                  30

Phe Lys Asp Cys
        35

<210> SEQ ID NO 26
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 26

Glu Thr Arg Val Ala Tyr Pro Tyr His Lys Asp Gly Arg Thr Val Lys
1               5                   10                  15

Trp Asp Ser His Asp Phe Asp Trp Gln Thr Pro Glu Pro Lys Leu Gly
            20                  25                  30

Phe Lys Asp Cys
        35

<210> SEQ ID NO 27
<211> LENGTH: 36

<212> TYPE: PRT
<213> ORGANISM: Artificial Sequence
<220> FEATURE:
<223> OTHER INFORMATION: Anaplasma antigenic peptide

<400> SEQUENCE: 27

Glu Thr Arg Val Ala Tyr Pro Tyr His Lys Asp Gly Arg Thr Val Lys
1               5                   10                  15

Tyr Asp Ser His Asp Phe Asp Trp Gln Thr Pro Glu Pro Lys Leu Gly
            20                  25                  30

Phe Lys Asp Cys
        35

<210> SEQ ID NO 28
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 28

Glu Thr Arg Val Ala Tyr Pro Tyr Ile Lys Asp Gly Arg Thr Val Lys
1               5                   10                  15

Ile Asp Ser His Asn Phe Asp Trp Gln Thr Pro Glu Pro Lys Leu Gly
            20                  25                  30

Phe Lys Asp Cys
        35

<210> SEQ ID NO 29
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 29

Glu Thr Arg Val Ala Tyr Pro Tyr Ile Lys Asp Gly Arg Thr Val Lys
1               5                   10                  15

Trp Asp Ser His Asn Phe Asp Trp Gln Thr Pro Glu Pro Lys Leu Gly
            20                  25                  30

Phe Lys Asp Cys
        35

<210> SEQ ID NO 30
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 30

Glu Thr Arg Val Ala Tyr Pro Tyr Ile Lys Asp Gly Arg Thr Val Lys
1               5                   10                  15

Tyr Asp Ser His Asn Phe Asp Trp Gln Thr Pro Glu Pro Lys Leu Gly
            20                  25                  30

Phe Lys Asp Cys
        35

<210> SEQ ID NO 31
<211> LENGTH: 36
<212> TYPE: PRT
<213> ORGANISM: Artificial Sequence
<220> FEATURE:

<223> OTHER INFORMATION: Anaplasma antigenic peptide

<400> SEQUENCE: 31

Glu Thr Arg Val Ala Tyr Pro Tyr Pro Lys Asp Gly Arg Thr Val Lys
1               5                   10                  15

Ile Asp Ser His Asn Phe Asp Trp Gln Thr Pro Glu Pro Lys Leu Gly
            20                  25                  30

Phe Lys Asp Cys
        35

<210> SEQ ID NO 32
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 32

Glu Thr Arg Val Ala Tyr Pro Tyr Pro Lys Asp Gly Arg Thr Val Lys
1               5                   10                  15

Trp Asp Ser His Asn Phe Asp Trp Gln Thr Pro Glu Pro Lys Leu Gly
            20                  25                  30

Phe Lys Asp Cys
        35

<210> SEQ ID NO 33
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 33

Glu Thr Arg Val Ala Tyr Pro Tyr Pro Lys Asp Gly Arg Thr Val Lys
1               5                   10                  15

Tyr Asp Ser His Asn Phe Asp Trp Gln Thr Pro Glu Pro Lys Leu Gly
            20                  25                  30

Phe Lys Asp Cys
        35

<210> SEQ ID NO 34
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 34

Glu Thr Arg Val Ala Tyr Pro Tyr His Lys Asp Gly Arg Thr Val Lys
1               5                   10                  15

Ile Asp Ser His Asn Phe Asp Trp Gln Thr Pro Glu Pro Lys Leu Gly
            20                  25                  30

Phe Lys Asp Cys
        35

<210> SEQ ID NO 35
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 35

Glu Thr Arg Val Ala Tyr Pro Tyr His Lys Asp Gly Arg Thr Val Lys
1               5                   10                  15

Trp Asp Ser His Asn Phe Asp Trp Gln Thr Pro Glu Pro Lys Leu Gly
            20                  25                  30

Phe Lys Asp Cys
        35

<210> SEQ ID NO 36
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 36

Glu Thr Arg Val Ala Tyr Pro Tyr His Lys Asp Gly Arg Thr Val Lys
1               5                   10                  15

Tyr Asp Ser His Asn Phe Asp Trp Gln Thr Pro Glu Pro Lys Leu Gly
            20                  25                  30

Phe Lys Asp Cys
        35

<210> SEQ ID NO 37
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 37

Glu Thr Arg Val Ala Tyr Pro Tyr Ile Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 38
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 38

Glu Thr Arg Val Ala Tyr Pro Tyr Pro Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 39
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 39

Glu Thr Arg Val Ala Tyr Pro Tyr His Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 40
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 40

Glu Thr Arg Val Ala Tyr Pro Tyr Ile Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 41
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 41

Glu Thr Arg Val Ala Tyr Pro Tyr Ile Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 42
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 42

Glu Thr Arg Val Ala Tyr Pro Tyr Pro Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 43
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 43

Glu Thr Arg Val Ala Tyr Pro Tyr Pro Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 44
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 44

Glu Thr Arg Val Ala Tyr Pro Tyr His Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 45
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 45

Glu Thr Arg Val Ala Tyr Pro Tyr His Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 46
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 46

Glu Thr Arg Val Ala Tyr Pro Tyr Ile Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 47
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 47

Glu Thr Arg Val Ala Tyr Pro Tyr Ile Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 48
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 48

Glu Thr Arg Val Ala Tyr Pro Tyr Ile Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 49
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 49

Glu Thr Arg Val Ala Tyr Pro Tyr Pro Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 50
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 50

Glu Thr Arg Val Ala Tyr Pro Tyr Pro Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 51
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 51

Glu Thr Arg Val Ala Tyr Pro Tyr Pro Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 52

```
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 52

Glu Thr Arg Val Ala Tyr Pro Tyr His Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 53
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 53

Glu Thr Arg Val Ala Tyr Pro Tyr His Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 54
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 54

Glu Thr Arg Val Ala Tyr Pro Tyr His Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 55
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 55

Glu Thr Arg Val Ala Tyr Pro Tyr Ile Lys Asp Gly Arg Thr Val Lys
1               5                   10                  15

Ile Asp Ser His Asn Phe Asp Trp Gln Thr Pro Asn Pro Lys Leu Gly
            20                  25                  30

Phe Lys Asp Cys
        35

<210> SEQ ID NO 56
<211> LENGTH: 36
<212> TYPE: PRT
<213> ORGANISM: Artificial Sequence
```

<220> FEATURE:
<223> OTHER INFORMATION: Anaplasma antigenic peptide

<400> SEQUENCE: 56

Glu Thr Arg Val Ala Tyr Pro Tyr Ile Lys Asp Gly Arg Thr Val Lys
1               5                   10                  15

Trp Asp Ser His Asn Phe Asp Trp Gln Thr Pro Asn Pro Lys Leu Gly
            20                  25                  30

Phe Lys Asp Cys
        35

<210> SEQ ID NO 57
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 57

Glu Thr Arg Val Ala Tyr Pro Tyr Ile Lys Asp Gly Arg Thr Val Lys
1               5                   10                  15

Tyr Asp Ser His Asn Phe Asp Trp Gln Thr Pro Asn Pro Lys Leu Gly
            20                  25                  30

Phe Lys Asp Cys
        35

<210> SEQ ID NO 58
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 58

Glu Thr Arg Val Ala Tyr Pro Tyr Pro Lys Asp Gly Arg Thr Val Lys
1               5                   10                  15

Ile Asp Ser His Asn Phe Asp Trp Gln Thr Pro Asn Pro Lys Leu Gly
            20                  25                  30

Phe Lys Asp Cys
        35

<210> SEQ ID NO 59
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 59

Glu Thr Arg Val Ala Tyr Pro Tyr Pro Lys Asp Gly Arg Thr Val Lys
1               5                   10                  15

Trp Asp Ser His Asn Phe Asp Trp Gln Thr Pro Asn Pro Lys Leu Gly
            20                  25                  30

Phe Lys Asp Cys
        35

<210> SEQ ID NO 60
<211> LENGTH: 36
<212> TYPE: PRT
<213> ORGANISM: Artificial Sequence
<220> FEATURE:
<223> OTHER INFORMATION: Anaplasma antigenic peptide

```
<400> SEQUENCE: 60

Glu Thr Arg Val Ala Tyr Pro Tyr Pro Lys Asp Gly Arg Thr Val Lys
1               5                   10                  15

Tyr Asp Ser His Asn Phe Asp Trp Gln Thr Pro Asn Pro Lys Leu Gly
                20                  25                  30

Phe Lys Asp Cys
        35

<210> SEQ ID NO 61
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 61

Glu Thr Arg Val Ala Tyr Pro Tyr His Lys Asp Gly Arg Thr Val Lys
1               5                   10                  15

Ile Asp Ser His Asn Phe Asp Trp Gln Thr Pro Asn Pro Lys Leu Gly
                20                  25                  30

Phe Lys Asp Cys
        35

<210> SEQ ID NO 62
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 62

Glu Thr Arg Val Ala Tyr Pro Tyr His Lys Asp Gly Arg Thr Val Lys
1               5                   10                  15

Trp Asp Ser His Asn Phe Asp Trp Gln Thr Pro Asn Pro Lys Leu Gly
                20                  25                  30

Phe Lys Asp Cys
        35

<210> SEQ ID NO 63
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 63

Glu Thr Arg Val Ala Tyr Pro Tyr His Lys Asp Gly Arg Thr Val Lys
1               5                   10                  15

Tyr Asp Ser His Asn Phe Asp Trp Gln Thr Pro Asn Pro Lys Leu Gly
                20                  25                  30

Phe Lys Asp Cys
        35

<210> SEQ ID NO 64
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 64

Glu Thr Arg Val Ala Tyr Pro Tyr Ile Lys Asp Gly Arg Thr Val Lys
```

```
1               5                   10                  15
Ile Asp Ser His Arg Phe Asp Trp Gln Thr Pro Glu Pro Lys Val Gly
            20                  25                  30

Phe Lys Asp Cys
        35

<210> SEQ ID NO 65
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 65

Glu Thr Arg Val Ala Tyr Pro Tyr Pro Lys Asp Gly Arg Thr Val Lys
1               5                   10                  15

Ile Asp Ser His Arg Phe Asp Trp Gln Thr Pro Glu Pro Lys Val Gly
            20                  25                  30

Phe Lys Asp Cys
        35

<210> SEQ ID NO 66
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 66

Glu Thr Arg Val Ala Tyr Pro Tyr His Lys Asp Gly Arg Thr Val Lys
1               5                   10                  15

Ile Asp Ser His Arg Phe Asp Trp Gln Thr Pro Glu Pro Lys Val Gly
            20                  25                  30

Phe Lys Asp Cys
        35

<210> SEQ ID NO 67
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 67

Glu Thr Arg Val Ala Tyr Pro Tyr Ile Lys Asp Gly Arg Thr Val Lys
1               5                   10                  15

Trp Asp Ser His Arg Phe Asp Trp Gln Thr Pro Glu Pro Lys Val Gly
            20                  25                  30

Phe Lys Asp Cys
        35

<210> SEQ ID NO 68
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 68

Glu Thr Arg Val Ala Tyr Pro Tyr Ile Lys Asp Gly Arg Thr Val Lys
1               5                   10                  15

Tyr Asp Ser His Arg Phe Asp Trp Gln Thr Pro Glu Pro Lys Val Gly
```

Phe Lys Asp Cys
        35

<210> SEQ ID NO 69
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 69

Glu Thr Arg Val Ala Tyr Pro Tyr Pro Lys Asp Gly Arg Thr Val Lys
1               5                   10                  15

Trp Asp Ser His Arg Phe Asp Trp Gln Thr Pro Glu Pro Lys Val Gly
            20                  25                  30

Phe Lys Asp Cys
        35

<210> SEQ ID NO 70
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 70

Glu Thr Arg Val Ala Tyr Pro Tyr Pro Lys Asp Gly Arg Thr Val Lys
1               5                   10                  15

Tyr Asp Ser His Arg Phe Asp Trp Gln Thr Pro Glu Pro Lys Val Gly
            20                  25                  30

Phe Lys Asp Cys
        35

<210> SEQ ID NO 71
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 71

Glu Thr Arg Val Ala Tyr Pro Tyr His Lys Asp Gly Arg Thr Val Lys
1               5                   10                  15

Trp Asp Ser His Arg Phe Asp Trp Gln Thr Pro Glu Pro Lys Val Gly
            20                  25                  30

Phe Lys Asp Cys
        35

<210> SEQ ID NO 72
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 72

Glu Thr Arg Val Ala Tyr Pro Tyr His Lys Asp Gly Arg Thr Val Lys
1               5                   10                  15

Tyr Asp Ser His Arg Phe Asp Trp Gln Thr Pro Glu Pro Lys Val Gly
            20                  25                  30

Phe Lys Asp Cys

-continued

```
<210> SEQ ID NO 73
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 73

Glu Thr Arg Val Ala Tyr Pro Tyr Ile Lys Asp Gly Arg Thr Val Lys
1               5                   10                  15

Ile Asp Ser His Asp Phe Asp Trp Gln Thr Pro Glu Pro Lys Val Gly
            20                  25                  30

Phe Lys Asp Cys
        35

<210> SEQ ID NO 74
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 74

Glu Thr Arg Val Ala Tyr Pro Tyr Ile Lys Asp Gly Arg Thr Val Lys
1               5                   10                  15

Trp Asp Ser His Asp Phe Asp Trp Gln Thr Pro Glu Pro Lys Val Gly
            20                  25                  30

Phe Lys Asp Cys
        35

<210> SEQ ID NO 75
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 75

Glu Thr Arg Val Ala Tyr Pro Tyr Ile Lys Asp Gly Arg Thr Val Lys
1               5                   10                  15

Tyr Asp Ser His Asp Phe Asp Trp Gln Thr Pro Glu Pro Lys Val Gly
            20                  25                  30

Phe Lys Asp Cys
        35

<210> SEQ ID NO 76
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 76

Glu Thr Arg Val Ala Tyr Pro Tyr Pro Lys Asp Gly Arg Thr Val Lys
1               5                   10                  15

Ile Asp Ser His Asp Phe Asp Trp Gln Thr Pro Glu Pro Lys Val Gly
            20                  25                  30

Phe Lys Asp Cys
        35
```

```
<210> SEQ ID NO 77
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 77
```

Glu Thr Arg Val Ala Tyr Pro Tyr Pro Lys Asp Gly Arg Thr Val Lys
1               5                   10                  15

Trp Asp Ser His Asp Phe Asp Trp Gln Thr Pro Glu Pro Lys Val Gly
            20                  25                  30

Phe Lys Asp Cys
        35

```
<210> SEQ ID NO 78
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 78
```

Glu Thr Arg Val Ala Tyr Pro Tyr Pro Lys Asp Gly Arg Thr Val Lys
1               5                   10                  15

Tyr Asp Ser His Asp Phe Asp Trp Gln Thr Pro Glu Pro Lys Val Gly
            20                  25                  30

Phe Lys Asp Cys
        35

```
<210> SEQ ID NO 79
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 79
```

Glu Thr Arg Val Ala Tyr Pro Tyr His Lys Asp Gly Arg Thr Val Lys
1               5                   10                  15

Ile Asp Ser His Asp Phe Asp Trp Gln Thr Pro Glu Pro Lys Val Gly
            20                  25                  30

Phe Lys Asp Cys
        35

```
<210> SEQ ID NO 80
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 80
```

Glu Thr Arg Val Ala Tyr Pro Tyr His Lys Asp Gly Arg Thr Val Lys
1               5                   10                  15

Trp Asp Ser His Asp Phe Asp Trp Gln Thr Pro Glu Pro Lys Val Gly
            20                  25                  30

Phe Lys Asp Cys
        35

```
<210> SEQ ID NO 81
<211> LENGTH: 36
<212> TYPE: PRT
```

<213> ORGANISM: Artificial Sequence
<220> FEATURE:
<223> OTHER INFORMATION: Anaplasma antigenic peptide

<400> SEQUENCE: 81

Glu Thr Arg Val Ala Tyr Pro Tyr His Lys Asp Gly Arg Thr Val Lys
1               5                   10                  15

Tyr Asp Ser His Asp Phe Asp Trp Gln Thr Pro Glu Pro Lys Val Gly
            20                  25                  30

Phe Lys Asp Cys
        35

<210> SEQ ID NO 82
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 82

Glu Thr Arg Val Ala Tyr Pro Tyr Ile Lys Asp Gly Arg Thr Val Lys
1               5                   10                  15

Ile Asp Ser His Asn Phe Asp Trp Gln Thr Pro Glu Pro Lys Val Gly
            20                  25                  30

Phe Lys Asp Cys
        35

<210> SEQ ID NO 83
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 83

Glu Thr Arg Val Ala Tyr Pro Tyr Ile Lys Asp Gly Arg Thr Val Lys
1               5                   10                  15

Trp Asp Ser His Asn Phe Asp Trp Gln Thr Pro Glu Pro Lys Val Gly
            20                  25                  30

Phe Lys Asp Cys
        35

<210> SEQ ID NO 84
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 84

Glu Thr Arg Val Ala Tyr Pro Tyr Ile Lys Asp Gly Arg Thr Val Lys
1               5                   10                  15

Tyr Asp Ser His Asn Phe Asp Trp Gln Thr Pro Glu Pro Lys Val Gly
            20                  25                  30

Phe Lys Asp Cys
        35

<210> SEQ ID NO 85
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 85

Glu Thr Arg Val Ala Tyr Pro Tyr Pro Lys Asp Gly Arg Thr Val Lys
1               5                   10                  15

Ile Asp Ser His Asn Phe Asp Trp Gln Thr Pro Glu Pro Lys Val Gly
                20                  25                  30

Phe Lys Asp Cys
        35

<210> SEQ ID NO 86
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 86

Glu Thr Arg Val Ala Tyr Pro Tyr Pro Lys Asp Gly Arg Thr Val Lys
1               5                   10                  15

Trp Asp Ser His Asn Phe Asp Trp Gln Thr Pro Glu Pro Lys Val Gly
                20                  25                  30

Phe Lys Asp Cys
        35

<210> SEQ ID NO 87
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 87

Glu Thr Arg Val Ala Tyr Pro Tyr Pro Lys Asp Gly Arg Thr Val Lys
1               5                   10                  15

Tyr Asp Ser His Asn Phe Asp Trp Gln Thr Pro Glu Pro Lys Val Gly
                20                  25                  30

Phe Lys Asp Cys
        35

<210> SEQ ID NO 88
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 88

Glu Thr Arg Val Ala Tyr Pro Tyr His Lys Asp Gly Arg Thr Val Lys
1               5                   10                  15

Ile Asp Ser His Asn Phe Asp Trp Gln Thr Pro Glu Pro Lys Val Gly
                20                  25                  30

Phe Lys Asp Cys
        35

<210> SEQ ID NO 89
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 89

Glu Thr Arg Val Ala Tyr Pro Tyr His Lys Asp Gly Arg Thr Val Lys
1               5                   10                  15

Trp Asp Ser His Asn Phe Asp Trp Gln Thr Pro Glu Pro Lys Val Gly
            20                  25                  30

Phe Lys Asp Cys
        35

<210> SEQ ID NO 90
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 90

Glu Thr Arg Val Ala Tyr Pro Tyr His Lys Asp Gly Arg Thr Val Lys
1               5                   10                  15

Tyr Asp Ser His Asn Phe Asp Trp Gln Thr Pro Glu Pro Lys Val Gly
            20                  25                  30

Phe Lys Asp Cys
        35

<210> SEQ ID NO 91
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 91

Glu Thr Arg Val Ala Tyr Pro Tyr Ile Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 92
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 92

Glu Thr Arg Val Ala Tyr Pro Tyr Pro Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 93
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 93

Glu Thr Arg Val Ala Tyr Pro Tyr His Lys Asp Gly Arg Thr Val Lys
1               5                   10                  15

Ile Asp Ser His Arg Phe Asp Trp Gln Thr Pro Asn Pro Lys Leu Gly
            20                  25                  30

Phe Lys Asp Cys
        35

<210> SEQ ID NO 94
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 94

Glu Thr Arg Val Ala Tyr Pro Tyr Ile Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 95
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 95

Glu Thr Arg Val Ala Tyr Pro Tyr Ile Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 96
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 96

Glu Thr Arg Val Ala Tyr Pro Tyr Pro Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 97
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 97

Glu Thr Arg Val Ala Tyr Pro Tyr Pro Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 98
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 98

Glu Thr Arg Val Ala Tyr Pro Tyr His Lys Asp Gly Arg Thr Val Lys
1               5                   10                  15

Trp Asp Ser His Arg Phe Asp Trp Gln Thr Pro Asn Pro Lys Leu Gly
            20                  25                  30

Phe Lys Asp Cys
        35

<210> SEQ ID NO 99
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 99

Glu Thr Arg Val Ala Tyr Pro Tyr His Lys Asp Gly Arg Thr Val Lys
1               5                   10                  15

Tyr Asp Ser His Arg Phe Asp Trp Gln Thr Pro Asn Pro Lys Leu Gly
            20                  25                  30

Phe Lys Asp Cys
        35

<210> SEQ ID NO 100
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 100

Glu Thr Arg Val Ala Tyr Pro Tyr Ile Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 101
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 101

Glu Thr Arg Val Ala Tyr Pro Tyr Ile Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 102
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 102

Glu Thr Arg Val Ala Tyr Pro Tyr Ile Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 103
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 103

Glu Thr Arg Val Ala Tyr Pro Tyr Pro Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 104
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 104

Glu Thr Arg Val Ala Tyr Pro Tyr Pro Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 105
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 105

Glu Thr Arg Val Ala Tyr Pro Tyr Pro Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 106
<211> LENGTH: 36

```
<212> TYPE: PRT
<213> ORGANISM: Artificial Sequence
<220> FEATURE:
<223> OTHER INFORMATION: Anaplasma antigenic peptide

<400> SEQUENCE: 106

Glu Thr Arg Val Ala Tyr Pro Tyr His Lys Asp Gly Arg Thr Val Lys
1               5                   10                  15

Ile Asp Ser His Asp Phe Asp Trp Gln Thr Pro Asn Pro Lys Leu Gly
            20                  25                  30

Phe Lys Asp Cys
        35

<210> SEQ ID NO 107
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 107

Glu Thr Arg Val Ala Tyr Pro Tyr His Lys Asp Gly Arg Thr Val Lys
1               5                   10                  15

Trp Asp Ser His Asp Phe Asp Trp Gln Thr Pro Asn Pro Lys Leu Gly
            20                  25                  30

Phe Lys Asp Cys
        35

<210> SEQ ID NO 108
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 108

Glu Thr Arg Val Ala Tyr Pro Tyr His Lys Asp Gly Arg Thr Val Lys
1               5                   10                  15

Tyr Asp Ser His Asp Phe Asp Trp Gln Thr Pro Asn Pro Lys Leu Gly
            20                  25                  30

Phe Lys Asp Cys
        35

<210> SEQ ID NO 109
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 109

Glu Thr Arg Val Ala Tyr Pro Tyr Ile Lys Asp Gly Arg Thr Val Lys
1               5                   10                  15

Ile Asp Ser His Asn Phe Asp Trp Gln Thr Pro Asn Pro Lys Leu Gly
            20                  25                  30

Phe Lys Asp Cys
        35

<210> SEQ ID NO 110
<211> LENGTH: 36
<212> TYPE: PRT
<213> ORGANISM: Artificial Sequence
<220> FEATURE:
```

<223> OTHER INFORMATION: Anaplasma antigenic peptide

<400> SEQUENCE: 110

Glu Thr Arg Val Ala Tyr Pro Tyr Ile Lys Asp Gly Arg Thr Val Lys
1               5                   10                  15

Trp Asp Ser His Asn Phe Asp Trp Gln Thr Pro Asn Pro Lys Leu Gly
            20                  25                  30

Phe Lys Asp Cys
        35

<210> SEQ ID NO 111
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 111

Glu Thr Arg Val Ala Tyr Pro Tyr Ile Lys Asp Gly Arg Thr Val Lys
1               5                   10                  15

Tyr Asp Ser His Asn Phe Asp Trp Gln Thr Pro Asn Pro Lys Leu Gly
            20                  25                  30

Phe Lys Asp Cys
        35

<210> SEQ ID NO 112
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 112

Glu Thr Arg Val Ala Tyr Pro Tyr Pro Lys Asp Gly Arg Thr Val Lys
1               5                   10                  15

Ile Asp Ser His Asn Phe Asp Trp Gln Thr Pro Asn Pro Lys Leu Gly
            20                  25                  30

Phe Lys Asp Cys
        35

<210> SEQ ID NO 113
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 113

Glu Thr Arg Val Ala Tyr Pro Tyr Pro Lys Asp Gly Arg Thr Val Lys
1               5                   10                  15

Trp Asp Ser His Asn Phe Asp Trp Gln Thr Pro Asn Pro Lys Leu Gly
            20                  25                  30

Phe Lys Asp Cys
        35

<210> SEQ ID NO 114
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 114

```
Glu Thr Arg Val Ala Tyr Pro Tyr Pro Lys Asp Gly Arg Thr Val Lys
1               5                   10                  15

Tyr Asp Ser His Asn Phe Asp Trp Gln Thr Pro Asn Pro Lys Leu Gly
            20                  25                  30

Phe Lys Asp Cys
        35

<210> SEQ ID NO 115
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 115

Glu Thr Arg Val Ala Tyr Pro Tyr His Lys Asp Gly Arg Thr Val Lys
1               5                   10                  15

Ile Asp Ser His Asn Phe Asp Trp Gln Thr Pro Asn Pro Lys Leu Gly
            20                  25                  30

Phe Lys Asp Cys
        35

<210> SEQ ID NO 116
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 116

Glu Thr Arg Val Ala Tyr Pro Tyr His Lys Asp Gly Arg Thr Val Lys
1               5                   10                  15

Trp Asp Ser His Asn Phe Asp Trp Gln Thr Pro Asn Pro Lys Leu Gly
            20                  25                  30

Phe Lys Asp Cys
        35

<210> SEQ ID NO 117
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 117

Glu Thr Arg Val Ala Tyr Pro Tyr His Lys Asp Gly Arg Thr Val Lys
1               5                   10                  15

Tyr Asp Ser His Asn Phe Asp Trp Gln Thr Pro Asn Pro Lys Leu Gly
            20                  25                  30

Phe Lys Asp Cys
        35

<210> SEQ ID NO 118
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 118

Ile Glu Leu Gly Tyr Glu Lys Phe Lys Thr Arg Gly Ile Arg Glu Ser
1               5                   10                  15
```

```
Gly Thr Lys Glu Cys
        20

<210> SEQ ID NO 119
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 119

Ile Glu Leu Gly Tyr Glu Asn Phe Lys Thr Arg Gly Ile Arg Glu Ser
1               5                   10                  15

Gly Thr Lys Glu Cys
        20

<210> SEQ ID NO 120
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 120

Ile Glu Leu Gly Tyr Glu Gln Phe Lys Thr Arg Gly Ile Arg Glu Ser
1               5                   10                  15

Gly Thr Lys Glu Cys
        20

<210> SEQ ID NO 121
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 121

Ile Glu Val Gly Tyr Glu Lys Phe Lys Thr Arg Gly Ile Arg Glu Ser
1               5                   10                  15

Gly Thr Lys Glu Cys
        20

<210> SEQ ID NO 122
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 122

Ile Glu Ala Gly Tyr Glu Lys Phe Lys Thr Arg Gly Ile Arg Glu Ser
1               5                   10                  15

Gly Thr Lys Glu Cys
        20

<210> SEQ ID NO 123
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 123

Ile Glu Val Gly Tyr Glu Asn Phe Lys Thr Arg Gly Ile Arg Glu Ser
```

```
                1               5                   10                  15

Gly Thr Lys Glu Cys
            20

<210> SEQ ID NO 124
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 124

Ile Glu Val Gly Tyr Glu Gln Phe Lys Thr Arg Gly Ile Arg Glu Ser
1               5                   10                  15

Gly Thr Lys Glu Cys
            20

<210> SEQ ID NO 125
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 125

Ile Glu Ala Gly Tyr Glu Asn Phe Lys Thr Arg Gly Ile Arg Glu Ser
1               5                   10                  15

Gly Thr Lys Glu Cys
            20

<210> SEQ ID NO 126
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 126

Ile Glu Ala Gly Tyr Glu Gln Phe Lys Thr Arg Gly Ile Arg Glu Ser
1               5                   10                  15

Gly Thr Lys Glu Cys
            20

<210> SEQ ID NO 127
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 127

Ile Glu Leu Gly Tyr Glu Lys Phe Lys Thr Asp Gly Ile Arg Glu Ser
1               5                   10                  15

Gly Thr Lys Glu Cys
            20

<210> SEQ ID NO 128
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 128
```

```
Ile Glu Leu Gly Tyr Glu Asn Phe Lys Thr Asp Gly Ile Arg Glu Ser
1               5                   10                  15

Gly Thr Lys Glu Cys
            20

<210> SEQ ID NO 129
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 129

Ile Glu Leu Gly Tyr Glu Gln Phe Lys Thr Asp Gly Ile Arg Glu Ser
1               5                   10                  15

Gly Thr Lys Glu Cys
            20

<210> SEQ ID NO 130
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 130

Ile Glu Val Gly Tyr Glu Lys Phe Lys Thr Asp Gly Ile Arg Glu Ser
1               5                   10                  15

Gly Thr Lys Glu Cys
            20

<210> SEQ ID NO 131
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 131

Ile Glu Ala Gly Tyr Glu Lys Phe Lys Thr Asp Gly Ile Arg Glu Ser
1               5                   10                  15

Gly Thr Lys Glu Cys
            20

<210> SEQ ID NO 132
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 132

Ile Glu Val Gly Tyr Glu Asn Phe Lys Thr Asp Gly Ile Arg Glu Ser
1               5                   10                  15

Gly Thr Lys Glu Cys
            20

<210> SEQ ID NO 133
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 133
```

Ile Glu Val Gly Tyr Glu Gln Phe Lys Thr Asp Gly Ile Arg Glu Ser
1               5                   10                  15

Gly Thr Lys Glu Cys
            20

<210> SEQ ID NO 134
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 134

Ile Glu Ala Gly Tyr Glu Asn Phe Lys Thr Asp Gly Ile Arg Glu Ser
1               5                   10                  15

Gly Thr Lys Glu Cys
            20

<210> SEQ ID NO 135
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 135

Ile Glu Ala Gly Tyr Glu Gln Phe Lys Thr Asp Gly Ile Arg Glu Ser
1               5                   10                  15

Gly Thr Lys Glu Cys
            20

<210> SEQ ID NO 136
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 136

Ile Glu Leu Gly Tyr Glu Lys Phe Lys Thr Asn Gly Ile Arg Glu Ser
1               5                   10                  15

Gly Thr Lys Glu Cys
            20

<210> SEQ ID NO 137
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 137

Ile Glu Leu Gly Tyr Glu Asn Phe Lys Thr Asn Gly Ile Arg Glu Ser
1               5                   10                  15

Gly Thr Lys Glu Cys
            20

<210> SEQ ID NO 138
<211> LENGTH: 21
<212> TYPE: PRT
<213> ORGANISM: Artificial Sequence
<220> FEATURE:
<223> OTHER INFORMATION: Anaplasma antigenic peptide -continued

```
<400> SEQUENCE: 138

Ile Glu Leu Gly Tyr Glu Gln Phe Lys Thr Asn Gly Ile Arg Glu Ser
1               5                   10                  15

Gly Thr Lys Glu Cys
            20

<210> SEQ ID NO 139
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 139

Ile Glu Val Gly Tyr Glu Lys Phe Lys Thr Asn Gly Ile Arg Glu Ser
1               5                   10                  15

Gly Thr Lys Glu Cys
            20

<210> SEQ ID NO 140
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 140

Ile Glu Ala Gly Tyr Glu Lys Phe Lys Thr Asn Gly Ile Arg Glu Ser
1               5                   10                  15

Gly Thr Lys Glu Cys
            20

<210> SEQ ID NO 141
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 141

Ile Glu Val Gly Tyr Glu Asn Phe Lys Thr Asn Gly Ile Arg Glu Ser
1               5                   10                  15

Gly Thr Lys Glu Cys
            20

<210> SEQ ID NO 142
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 142

Ile Glu Val Gly Tyr Glu Gln Phe Lys Thr Asn Gly Ile Arg Glu Ser
1               5                   10                  15

Gly Thr Lys Glu Cys
            20

<210> SEQ ID NO 143
<211> LENGTH: 21
<212> TYPE: PRT
<213> ORGANISM: Artificial Sequence
<220> FEATURE:
<223> OTHER INFORMATION: Anaplasma antigenic peptide
```

```
<400> SEQUENCE: 143

Ile Glu Ala Gly Tyr Glu Asn Phe Lys Thr Asn Gly Ile Arg Glu Ser
1               5                   10                  15

Gly Thr Lys Glu Cys
            20

<210> SEQ ID NO 144
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 144

Ile Glu Ala Gly Tyr Glu Gln Phe Lys Thr Asn Gly Ile Arg Glu Ser
1               5                   10                  15

Gly Thr Lys Glu Cys
            20

<210> SEQ ID NO 145
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 145

Ile Glu Leu Gly Tyr Glu Lys Phe Lys Thr Arg Gly Ile Arg Asn Ser
1               5                   10                  15

Gly Thr Lys Glu Cys
            20

<210> SEQ ID NO 146
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 146

Ile Glu Leu Gly Tyr Glu Asn Phe Lys Thr Arg Gly Ile Arg Asn Ser
1               5                   10                  15

Gly Thr Lys Glu Cys
            20

<210> SEQ ID NO 147
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 147

Ile Glu Leu Gly Tyr Glu Gln Phe Lys Thr Arg Gly Ile Arg Asn Ser
1               5                   10                  15

Gly Thr Lys Glu Cys
            20

<210> SEQ ID NO 148
<211> LENGTH: 21
<212> TYPE: PRT
<213> ORGANISM: Artificial Sequence
<220> FEATURE:
```

<223> OTHER INFORMATION: Anaplasma antigenic peptide

<400> SEQUENCE: 148

Ile Glu Val Gly Tyr Glu Lys Phe Lys Thr Arg Gly Ile Arg Asn Ser
1               5                   10                  15

Gly Thr Lys Glu Cys
            20

<210> SEQ ID NO 149
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 149

Ile Glu Ala Gly Tyr Glu Lys Phe Lys Thr Arg Gly Ile Arg Asn Ser
1               5                   10                  15

Gly Thr Lys Glu Cys
            20

<210> SEQ ID NO 150
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 150

Ile Glu Val Gly Tyr Glu Asn Phe Lys Thr Arg Gly Ile Arg Asn Ser
1               5                   10                  15

Gly Thr Lys Glu Cys
            20

<210> SEQ ID NO 151
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 151

Ile Glu Val Gly Tyr Glu Gln Phe Lys Thr Arg Gly Ile Arg Asn Ser
1               5                   10                  15

Gly Thr Lys Glu Cys
            20

<210> SEQ ID NO 152
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 152

Ile Glu Ala Gly Tyr Glu Asn Phe Lys Thr Arg Gly Ile Arg Asn Ser
1               5                   10                  15

Gly Thr Lys Glu Cys
            20

<210> SEQ ID NO 153
<211> LENGTH: 21
<212> TYPE: PRT
<213> ORGANISM: Artificial Sequence

```
<220> FEATURE:
<223> OTHER INFORMATION: Anaplasma antigenic peptide

<400> SEQUENCE: 153

Ile Glu Ala Gly Tyr Glu Gln Phe Lys Thr Arg Gly Ile Arg Asn Ser
1               5                   10                  15

Gly Thr Lys Glu Cys
            20

<210> SEQ ID NO 154
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 154

Ile Glu Leu Gly Tyr Glu Lys Phe Lys Thr Asp Gly Ile Arg Asn Ser
1               5                   10                  15

Gly Thr Lys Glu Cys
            20

<210> SEQ ID NO 155
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 155

Ile Glu Leu Gly Tyr Glu Asn Phe Lys Thr Asp Gly Ile Arg Asn Ser
1               5                   10                  15

Gly Thr Lys Glu Cys
            20

<210> SEQ ID NO 156
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 156

Ile Glu Leu Gly Tyr Glu Gln Phe Lys Thr Asp Gly Ile Arg Asn Ser
1               5                   10                  15

Gly Thr Lys Glu Cys
            20

<210> SEQ ID NO 157
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 157

Ile Glu Val Gly Tyr Glu Lys Phe Lys Thr Asp Gly Ile Arg Asn Ser
1               5                   10                  15

Gly Thr Lys Glu Cys
            20

<210> SEQ ID NO 158
<211> LENGTH: 21
<212> TYPE: PRT
```

```
<213> ORGANISM: Artificial Sequence
<220> FEATURE:
<223> OTHER INFORMATION: Anaplasma antigenic peptide

<400> SEQUENCE: 158

Ile Glu Ala Gly Tyr Glu Lys Phe Lys Thr Asp Gly Ile Arg Asn Ser
1               5                   10                  15

Gly Thr Lys Glu Cys
            20

<210> SEQ ID NO 159
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 159

Ile Glu Val Gly Tyr Glu Asn Phe Lys Thr Asp Gly Ile Arg Asn Ser
1               5                   10                  15

Gly Thr Lys Glu Cys
            20

<210> SEQ ID NO 160
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 160

Ile Glu Val Gly Tyr Glu Gln Phe Lys Thr Asp Gly Ile Arg Asn Ser
1               5                   10                  15

Gly Thr Lys Glu Cys
            20

<210> SEQ ID NO 161
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 161

Ile Glu Ala Gly Tyr Glu Asn Phe Lys Thr Asp Gly Ile Arg Asn Ser
1               5                   10                  15

Gly Thr Lys Glu Cys
            20

<210> SEQ ID NO 162
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 162

Ile Glu Ala Gly Tyr Glu Gln Phe Lys Thr Asp Gly Ile Arg Asn Ser
1               5                   10                  15

Gly Thr Lys Glu Cys
            20

<210> SEQ ID NO 163
<211> LENGTH: 21
```

<212> TYPE: PRT
<213> ORGANISM: Artificial Sequence
<220> FEATURE:
<223> OTHER INFORMATION: Anaplasma antigenic peptide

<400> SEQUENCE: 163

Ile Glu Leu Gly Tyr Glu Lys Phe Lys Thr Asn Gly Ile Arg Asn Ser
1               5                   10                  15

Gly Thr Lys Glu Cys
            20

<210> SEQ ID NO 164
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 164

Ile Glu Leu Gly Tyr Glu Asn Phe Lys Thr Asn Gly Ile Arg Asn Ser
1               5                   10                  15

Gly Thr Lys Glu Cys
            20

<210> SEQ ID NO 165
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 165

Ile Glu Leu Gly Tyr Glu Gln Phe Lys Thr Asn Gly Ile Arg Asn Ser
1               5                   10                  15

Gly Thr Lys Glu Cys
            20

<210> SEQ ID NO 166
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 166

Ile Glu Val Gly Tyr Glu Lys Phe Lys Thr Asn Gly Ile Arg Asn Ser
1               5                   10                  15

Gly Thr Lys Glu Cys
            20

<210> SEQ ID NO 167
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 167

Ile Glu Ala Gly Tyr Glu Lys Phe Lys Thr Asn Gly Ile Arg Asn Ser
1               5                   10                  15

Gly Thr Lys Glu Cys
            20

<210> SEQ ID NO 168

-continued

```
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 168

Ile Glu Val Gly Tyr Glu Asn Phe Lys Thr Asn Gly Ile Arg Asn Ser
1               5                   10                  15

Gly Thr Lys Glu Cys
            20

<210> SEQ ID NO 169
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 169

Ile Glu Val Gly Tyr Glu Gln Phe Lys Thr Asn Gly Ile Arg Asn Ser
1               5                   10                  15

Gly Thr Lys Glu Cys
            20

<210> SEQ ID NO 170
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 170

Ile Glu Ala Gly Tyr Glu Asn Phe Lys Thr Asn Gly Ile Arg Asn Ser
1               5                   10                  15

Gly Thr Lys Glu Cys
            20

<210> SEQ ID NO 171
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 171

Ile Glu Ala Gly Tyr Glu Gln Phe Lys Thr Asn Gly Ile Arg Asn Ser
1               5                   10                  15

Gly Thr Lys Glu Cys
            20

<210> SEQ ID NO 172
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 172

Ile Glu Leu Gly Tyr Glu Lys Phe Lys Thr Arg Gly Ile Arg Gln Ser
1               5                   10                  15

Gly Thr Lys Glu Cys
            20
```

```
<210> SEQ ID NO 173
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 173

Ile Glu Leu Gly Tyr Glu Asn Phe Lys Thr Arg Gly Ile Arg Gln Ser
1               5                   10                  15

Gly Thr Lys Glu Cys
            20

<210> SEQ ID NO 174
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 174

Ile Glu Leu Gly Tyr Glu Gln Phe Lys Thr Arg Gly Ile Arg Gln Ser
1               5                   10                  15

Gly Thr Lys Glu Cys
            20

<210> SEQ ID NO 175
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 175

Ile Glu Val Gly Tyr Glu Lys Phe Lys Thr Arg Gly Ile Arg Gln Ser
1               5                   10                  15

Gly Thr Lys Glu Cys
            20

<210> SEQ ID NO 176
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 176

Ile Glu Ala Gly Tyr Glu Lys Phe Lys Thr Arg Gly Ile Arg Gln Ser
1               5                   10                  15

Gly Thr Lys Glu Cys
            20

<210> SEQ ID NO 177
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 177

Ile Glu Val Gly Tyr Glu Asn Phe Lys Thr Arg Gly Ile Arg Gln Ser
1               5                   10                  15

Gly Thr Lys Glu Cys
            20
```

<210> SEQ ID NO 178
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 178

Ile Glu Val Gly Tyr Glu Gln Phe Lys Thr Arg Gly Ile Arg Gln Ser
1               5                   10                  15

Gly Thr Lys Glu Cys
            20

<210> SEQ ID NO 179
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 179

Ile Glu Ala Gly Tyr Glu Asn Phe Lys Thr Arg Gly Ile Arg Gln Ser
1               5                   10                  15

Gly Thr Lys Glu Cys
            20

<210> SEQ ID NO 180
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 180

Ile Glu Ala Gly Tyr Glu Gln Phe Lys Thr Arg Gly Ile Arg Gln Ser
1               5                   10                  15

Gly Thr Lys Glu Cys
            20

<210> SEQ ID NO 181
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 181

Ile Glu Leu Gly Tyr Glu Lys Phe Lys Thr Asp Gly Ile Arg Gln Ser
1               5                   10                  15

Gly Thr Lys Glu Cys
            20

<210> SEQ ID NO 182
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 182

Ile Glu Leu Gly Tyr Glu Asn Phe Lys Thr Asp Gly Ile Arg Gln Ser
1               5                   10                  15

Gly Thr Lys Glu Cys
            20

<210> SEQ ID NO 183
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 183

Ile Glu Leu Gly Tyr Glu Gln Phe Lys Thr Asp Gly Ile Arg Gln Ser
1               5                   10                  15

Gly Thr Lys Glu Cys
            20

<210> SEQ ID NO 184
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 184

Ile Glu Val Gly Tyr Glu Lys Phe Lys Thr Asp Gly Ile Arg Gln Ser
1               5                   10                  15

Gly Thr Lys Glu Cys
            20

<210> SEQ ID NO 185
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 185

Ile Glu Ala Gly Tyr Glu Lys Phe Lys Thr Asp Gly Ile Arg Gln Ser
1               5                   10                  15

Gly Thr Lys Glu Cys
            20

<210> SEQ ID NO 186
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 186

Ile Glu Val Gly Tyr Glu Asn Phe Lys Thr Asp Gly Ile Arg Gln Ser
1               5                   10                  15

Gly Thr Lys Glu Cys
            20

<210> SEQ ID NO 187
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 187

Ile Glu Val Gly Tyr Glu Gln Phe Lys Thr Asp Gly Ile Arg Gln Ser
1               5                   10                  15

Gly Thr Lys Glu Cys

20

<210> SEQ ID NO 188
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 188

Ile Glu Ala Gly Tyr Glu Asn Phe Lys Thr Asp Gly Ile Arg Gln Ser
1               5                   10                  15

Gly Thr Lys Glu Cys
            20

<210> SEQ ID NO 189
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 189

Ile Glu Ala Gly Tyr Glu Gln Phe Lys Thr Asp Gly Ile Arg Gln Ser
1               5                   10                  15

Gly Thr Lys Glu Cys
            20

<210> SEQ ID NO 190
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 190

Ile Glu Leu Gly Tyr Glu Lys Phe Lys Thr Asn Gly Ile Arg Gln Ser
1               5                   10                  15

Gly Thr Lys Glu Cys
            20

<210> SEQ ID NO 191
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 191

Ile Glu Leu Gly Tyr Glu Asn Phe Lys Thr Asn Gly Ile Arg Gln Ser
1               5                   10                  15

Gly Thr Lys Glu Cys
            20

<210> SEQ ID NO 192
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 192

Ile Glu Leu Gly Tyr Glu Gln Phe Lys Thr Asn Gly Ile Arg Gln Ser
1               5                   10                  15

```
Gly Thr Lys Glu Cys
        20

<210> SEQ ID NO 193
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 193

Ile Glu Val Gly Tyr Glu Lys Phe Lys Thr Asn Gly Ile Arg Gln Ser
1               5                   10                  15

Gly Thr Lys Glu Cys
        20

<210> SEQ ID NO 194
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 194

Ile Glu Ala Gly Tyr Glu Lys Phe Lys Thr Asn Gly Ile Arg Gln Ser
1               5                   10                  15

Gly Thr Lys Glu Cys
        20

<210> SEQ ID NO 195
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 195

Ile Glu Val Gly Tyr Glu Asn Phe Lys Thr Asn Gly Ile Arg Gln Ser
1               5                   10                  15

Gly Thr Lys Glu Cys
        20

<210> SEQ ID NO 196
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 196

Ile Glu Val Gly Tyr Glu Gln Phe Lys Thr Asn Gly Ile Arg Gln Ser
1               5                   10                  15

Gly Thr Lys Glu Cys
        20

<210> SEQ ID NO 197
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 197

Ile Glu Ala Gly Tyr Glu Asn Phe Lys Thr Asn Gly Ile Arg Gln Ser
1               5                   10                  15
```

```
Gly Thr Lys Glu Cys
            20

<210> SEQ ID NO 198
<211> LENGTH: 21
<212> TYPE: PRT
<213> ORGANISM: Artificial Sequence
<220> FEATURE:
<223> OTHER INFORMATION: Anaplasma antigenic peptide

<400> SEQUENCE: 198

Ile Glu Ala Gly Tyr Glu Gln Phe Lys Thr Asn Gly Ile Arg Gln Ser
1               5                  10                  15

Gly Thr Lys Glu Cys
            20

<210> SEQ ID NO 199
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 199

Glu Thr Lys Val Val Tyr Gly Tyr Leu Lys Glu Gly Arg Thr Val Lys
1               5                  10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 200
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 200

Glu Thr Lys Val Val Tyr Ile Tyr Leu Lys Glu Gly Arg Thr Val Lys
1               5                  10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 201
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 201
```

Glu Thr Lys Val Val Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 202
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 202

Glu Thr Lys Val Ala Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 203
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 203

Glu Thr Lys Val Ala Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 204
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 204

Glu Thr Lys Val Ala Tyr His Tyr Leu Lys Glu Gly Arg Thr Val Lys
1               5                   10                  15

```
Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 205
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 205

```
Glu Thr Lys Val Val Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 206
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 206

```
Glu Thr Lys Val Val Tyr Ile Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 207
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 207

```
Glu Thr Lys Val Val Tyr His Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
```

```
                 35                  40                  45
Lys Ala Asp Lys Phe Glu Trp Asn Ser Pro Asp Phe Arg Ile Ile Phe
         50                  55                  60

Lys Gln Cys
 65

<210> SEQ ID NO 208
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 208

Glu Thr Lys Val Ala Tyr Gly Tyr Leu Lys Asn Gly Arg Thr Val Lys
 1               5                  10                  15

Leu Asp Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
         50                  55                  60

Lys Gln Cys
 65

<210> SEQ ID NO 209
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 209

Glu Thr Lys Val Ala Tyr Ile Tyr Leu Lys Asn Gly Arg Thr Val Lys
 1               5                  10                  15

Leu Asp Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
         50                  55                  60

Lys Gln Cys
 65

<210> SEQ ID NO 210
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 210

Glu Thr Lys Val Ala Tyr His Tyr Leu Lys Asn Gly Arg Thr Val Lys
 1               5                  10                  15

Leu Asp Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
         50                  55                  60
```

```
Lys Gln Cys
 65

<210> SEQ ID NO 211
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 211

Glu Thr Lys Val Val Tyr Gly Tyr Leu Lys Gln Gly Arg Thr Val Lys
 1               5                  10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
     50                  55                  60

Lys Gln Cys
 65

<210> SEQ ID NO 212
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 212

Glu Thr Lys Val Val Tyr Ile Tyr Leu Lys Gln Gly Arg Thr Val Lys
 1               5                  10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
     50                  55                  60

Lys Gln Cys
 65

<210> SEQ ID NO 213
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 213

Glu Thr Lys Val Val Tyr His Tyr Leu Lys Gln Gly Arg Thr Val Lys
 1               5                  10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
     50                  55                  60

Lys Gln Cys
 65
```

<210> SEQ ID NO 214
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 214

```
Glu Thr Lys Val Ala Tyr Gly Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 215
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 215

```
Glu Thr Lys Val Ala Tyr Ile Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 216
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 216

```
Glu Thr Lys Val Ala Tyr His Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 217
<211> LENGTH: 67
<212> TYPE: PRT

```
<213> ORGANISM: Artificial Sequence
<220> FEATURE:
<223> OTHER INFORMATION: Anaplasma antigenic peptide

<400> SEQUENCE: 217

Glu Thr Lys Val Val Tyr Gly Tyr Leu Lys Glu Gly Arg Thr Val Lys
1               5                   10                  15

```
<400> SEQUENCE: 220

Glu Thr Lys Val Ala Tyr Gly Tyr Leu Lys Glu Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
50                  55                      60

Lys Gln Cys
65

<210> SEQ ID NO 221
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 221

Glu Thr Lys Val Ala Tyr Ile Tyr Leu Lys Glu Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
50                  55                      60

Lys Gln Cys
65

<210> SEQ ID NO 222
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 222

Glu Thr Lys Val Ala Tyr His Tyr Leu Lys Glu Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
50                  55                      60

Lys Gln Cys
65

<210> SEQ ID NO 223
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 223

Glu Thr Lys Val Val Tyr Gly Tyr Leu Lys Asn Gly Arg Thr Val Lys
1               5                   10                  15
```

```
Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 224
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 224

Glu Thr Lys Val Val Tyr Ile Tyr Leu Lys Asn Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 225
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 225

Glu Thr Lys Val Val His Tyr Leu Lys Asn Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 226
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 226

Glu Thr Lys Val Ala Tyr Gly Tyr Leu Lys Asn Gly Arg Thr Val Lys
1               5                   10                  15

Leu Asn Ser His Arg Phe Asp Trp Gln Thr Pro Glu Pro Lys Leu Gly
            20                  25                  30
```

```
Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 227
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 227

Glu Thr Lys Val Ala Tyr Ile Tyr Leu Lys Asn Gly Arg Thr Val Lys
 1               5                  10                  15

Leu Asn Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 228
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 228

Glu Thr Lys Val Ala His Tyr Leu Lys Asn Gly Arg Thr Val Lys
 1               5                  10                  15

Leu Asn Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 229
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 229

Glu Thr Lys Val Val Tyr Gly Tyr Leu Lys Gln Gly Arg Thr Val Lys
 1               5                  10                  15

Leu Asn Ser His Arg Phe Asp Trp Gln Thr Pro Glu Pro Lys Leu Gly
             20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
```

Lys Gln Cys
65

<210> SEQ ID NO 230
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 230

Glu Thr Lys Val Val Tyr Ile Tyr Leu Lys Gln Gly Arg Thr Val Lys
1               5                   10                  15

Leu Asn Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 231
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 231

Glu Thr Lys Val Val Tyr His Tyr Leu Lys Gln Gly Arg Thr Val Lys
1               5                   10                  15

Leu Asn Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 232
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 232

Glu Thr Lys Val Ala Tyr Gly Tyr Leu Lys Gln Gly Arg Thr Val Lys
1               5                   10                  15

Leu Asn Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 233
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 233

Glu Thr Lys Val Ala Tyr Ile Tyr Leu Lys Gln Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 234
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 234

Glu Thr Lys Val Ala Tyr His Tyr Leu Lys Gln Gly Arg Thr Val Lys
1               5                   10                  15

Leu Asn Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 235
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 235

Glu Thr Lys Val Val Tyr Gly Tyr Leu Lys Glu Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 236
<211> LENGTH: 67

<212> TYPE: PRT
<213> ORGANISM: Artificial Sequence
<220> FEATURE:
<223> OTHER INFORMATION: Anaplasma antigenic peptide

<400> SEQUENCE: 236

Glu Thr Lys Val Val Tyr Ile Tyr Leu Lys Glu Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 237
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 237

Glu Thr Lys Val Val Tyr His Tyr Leu Lys Glu Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 238
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 238

Glu Thr Lys Val Ala Tyr Gly Tyr Leu Lys Gly Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 239
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 239

Glu Thr Lys Val Ala Tyr Ile Tyr Leu Lys Glu Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 240
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 240

Glu Thr Lys Val Ala Tyr His Tyr Leu Lys Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 241
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 241

Glu Thr Lys Val Val Tyr Gly Tyr Leu Lys Asn Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 242
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 242

Glu Thr Lys Val Val Tyr Ile Tyr Leu Lys Asn Gly Arg Thr Val Lys

```
1               5                   10                  15
Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
 50                      55                  60

Lys Gln Cys
 65

<210> SEQ ID NO 243
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 243

Glu Thr Lys Val Val Tyr His Tyr Leu Lys Asn Gly Arg Thr Val Lys
 1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
 50                      55                  60

Lys Gln Cys
 65

<210> SEQ ID NO 244
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 244

Glu Thr Lys Val Ala Tyr Gly Tyr Leu Lys Asn Gly Arg Thr Val Lys
 1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
 50                      55                  60

Lys Gln Cys
 65

<210> SEQ ID NO 245
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 245

Glu Thr Lys Val Ala Tyr Ile Tyr Leu Lys Asn Gly Arg Thr Val Lys
 1               5                   10                  15

Leu Asp Ser His Asp Phe Asp Trp Gln Thr Pro Glu Pro Lys Leu Gly
            20                  25                  30
```

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 246
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 246

Glu Thr Lys Val Ala Tyr His Tyr Leu Lys Asn Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 247
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 247

Glu Thr Lys Val Val Tyr Gly Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 248
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 248

Glu Thr Lys Val Val Tyr Ile Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
 65

<210> SEQ ID NO 249
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 249

Glu Thr Lys Val Val Tyr His Tyr Leu Lys Gln Gly Arg Thr Val Lys
 1               5                  10                  15

Leu Asp Ser His Asp Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
 65

<210> SEQ ID NO 250
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 250

Glu Thr Lys Val Ala Tyr Gly Tyr Leu Lys Gln Gly Arg Thr Val Lys
 1               5                  10                  15

Leu Asp Ser His Asp Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
 65

<210> SEQ ID NO 251
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 251

Glu Thr Lys Val Ala Tyr Ile Tyr Leu Lys Gln Gly Arg Thr Val Lys
 1               5                  10                  15

Leu Asp Ser His Asp Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys

<210> SEQ ID NO 252
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 252

Glu Thr Lys Val Ala Tyr His Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 253
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 253

Glu Thr Lys Val Val Tyr Gly Tyr Leu Lys Gln Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 254
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 254

Glu Thr Lys Val Val Tyr Ile Tyr Leu Lys Gln Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 255

```
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 255

Glu Thr Lys Val Val Tyr His Tyr Leu Lys Glu Gly Arg Th

<223> OTHER INFORMATION: Anaplasma antigenic peptide

<400> SEQUENCE: 258

Glu Thr Lys Val Ala Tyr His Tyr Leu Lys Glu Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 259
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 259

Glu Thr Lys Val Val Tyr Gly Tyr Leu Lys Asn Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 260
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 260

Glu Thr Lys Val Val Tyr Ile Tyr Leu Lys Asn Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 261
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 261

```
Glu Thr Lys Val Val Tyr His Tyr Leu Lys Asn Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 262
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 262

Glu Thr Lys Val Ala Tyr Gly Tyr Leu Lys Asn Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 263
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 263

Glu Thr Lys Val Ala Tyr Ile Tyr Leu Lys Asn Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 264
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 264

Glu Thr Lys Val Ala Tyr His Tyr Leu Lys Asn Gly Arg Thr Val Lys
1               5                   10                  15

Leu Asn Ser His Asp Phe Asp Trp Gln Thr Pro Glu Pro Lys Leu Gly
```

20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 265
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 265

Glu Thr Lys Val Val Tyr Gly Tyr Leu Lys Gln Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 266
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 266

Glu Thr Lys Val Val Tyr Ile Tyr Leu Lys Gln Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 267
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 267

Glu Thr Lys Val Val Tyr His Tyr Leu Lys Gln Gly Arg Thr Val Lys
1               5                   10                  15

Leu Asn Ser His Asp Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

-continued

Lys Ala Asp Lys Phe Glu Trp Asn Ser Pro Asp Phe Arg Ile Ile Phe
                50                  55                  60

Lys Gln Cys
 65

<210> SEQ ID NO 268
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 268

Glu Thr Lys Val Ala Tyr Gly Tyr Leu Lys Gln Gly Arg Thr Val Lys
 1               5                  10                  15

Leu Asn Ser His Asp Phe Asp Trp Gln Thr Pro Glu Pro Lys Leu Gly
                20                  25                  30

Phe Lys Asp Gly Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
 65

<210> SEQ ID NO 269
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 269

Glu Thr Lys Val Ala Tyr Ile Tyr Leu Lys Gln Gly Arg Thr Val Lys
 1               5                  10                  15

Leu Asn Ser His Asp Phe Asp Trp Gln Thr Pro Glu Pro Lys Leu Gly
                20                  25                  30

Phe Lys Asp Gly Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
 65

<210> SEQ ID NO 270
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 270

Glu Thr Lys Val Ala Tyr His Tyr Leu Lys Gln Gly Arg Thr Val Lys
 1               5                  10                  15

Leu Asn Ser His Asp Phe Asp Trp Gln Thr Pro Glu Pro Lys Leu Gly
                20                  25                  30

Phe Lys Asp Gly Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Gln Cys
65

<210> SEQ ID NO 271
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 271

Glu Thr Lys Val Val Tyr Gly Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 272
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 272

Glu Thr Lys Val Val Tyr Ile Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 273
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 273

Glu Thr Lys Val Val Tyr His Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 274
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 274

```
Glu Thr Lys Val Ala Tyr Gly Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 275
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 275

```
Glu Thr Lys Val Ala Tyr Ile Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 276
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 276

```
Glu Thr Lys Val Ala Tyr His Tyr Leu Lys Glu Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 277
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 277

Glu Thr Lys Val Val Tyr Gly Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 278
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 278

Glu Thr Lys Val Val Tyr Ile Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 279
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 279

Glu Thr Lys Val Val Tyr His Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 280
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 280

Glu Thr Lys Val Ala Tyr Gly Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 281
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 281

Glu Thr Lys Val Ala Tyr Ile Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 282
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 282

Glu Thr Lys Val Ala Tyr His Tyr Leu Lys Asn Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 283
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 283

Glu Thr Lys Val Val Tyr Gly Tyr Leu Lys Gln Gly Arg Thr Val Lys
1               5                   10                  15

```
Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
 50                  55                  60

Lys Gln Cys
 65
```

<210> SEQ ID NO 284
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 284

```
Glu Thr Lys Val Val Tyr Ile Tyr Leu Lys Gln Gly Arg Thr Val Lys
 1               5                  10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
 50                  55                  60

Lys Gln Cys
 65
```

<210> SEQ ID NO 285
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 285

```
Glu Thr Lys Val Val Tyr His Tyr Leu Lys Gln Gly Arg Thr Val Lys
 1               5                  10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
 50                  55                  60

Lys Gln Cys
 65
```

<210> SEQ ID NO 286
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 286

```
Glu Thr Lys Val Ala Tyr Gly Tyr Leu Lys Gln Gly Arg Thr Val Lys
 1               5                  10                  15

Leu Asp Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
```

```
                35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 287
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 287

Glu Thr Lys Val Ala Tyr Ile Tyr Leu Lys Gln Gly Arg Thr Val Lys
 1               5                  10                  15

Leu Asp Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
                35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 288
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 288

Glu Thr Lys Val Ala Tyr His Tyr Leu Lys Gln Gly Arg Thr Val Lys
 1               5                  10                  15

Leu Asp Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
                35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 289
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 289

Glu Thr Lys Val Val Tyr Gly Tyr Leu Lys Glu Gly Arg Thr Val Lys
 1               5                  10                  15

Leu Asn Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
                35                  40                  45

Lys Ala Asp Lys Phe Glu Trp Asn Ser Pro Asp Phe Arg Ile Ile Phe
 50                  55                  60
```

Lys Gln Cys
65

<210> SEQ ID NO 290
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 290

Glu Thr Lys Val Val Tyr Ile Tyr Leu Lys Glu Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 291
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 291

Glu Thr Lys Val Val Tyr His Tyr Leu Lys Glu Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 292
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 292

Glu Thr Lys Val Ala Tyr Gly Tyr Leu Lys Glu Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 293
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 293

Glu Thr Lys Val Ala Tyr Ile Tyr Leu Lys Glu Gly Arg Thr Val Lys
1               5                   10                  15

Leu Asn Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 294
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 294

Glu Thr Lys Val Ala Tyr His Tyr Leu Lys Glu Gly Arg Thr Val Lys
1               5                   10                  15

Leu Asn Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 295
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 295

Glu Thr Lys Val Val Tyr Gly Tyr Leu Lys Asn Gly Arg Thr Val Lys
1               5                   10                  15

Leu Asn Ser His Asn Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 296
<211> LENGTH: 67
<212> TYPE: PRT

<213> ORGANISM: Artificial Sequence
<220> FEATURE:
<223> OTHER INFORMATION: Anaplasma antigenic peptide

<400> SEQUENCE: 296

```
Glu Thr Lys Val Val Tyr Ile Tyr Leu Lys Asn Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 297
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 297

```
Glu Thr Lys Val Val Tyr His Tyr Leu Lys Asn Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 298
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 298

```
Glu Thr Lys Val Ala Tyr Gly Tyr Leu Lys Asn Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65
```

<210> SEQ ID NO 299
<211> LENGTH: 67
<212> TYPE: PRT
<213> ORGANISM: Artificial Sequence
<220> FEATURE:
<223> OTHER INFORMATION: Anaplasma antigenic peptide

```
<400> SEQUENCE: 299

Glu Thr Lys Val Ala Tyr Ile Tyr Leu Lys Asn Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 300
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 300

Glu Thr Lys Val Ala Tyr His Tyr Leu Lys Asn Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 301
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 301

Glu Thr Lys Val Val Tyr Gly Tyr Leu Lys Gln Gly Arg Thr Val Lys
1               5                   10                  15

Leu Asn Ser His Asn Phe

-continued

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 303
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 303

Glu Thr Lys Val Val Tyr His Tyr Leu Lys Gln Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 304
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 304

Glu Thr Lys Val Ala Tyr Gly Tyr Leu Lys Gln Gly Arg Thr Val Lys
1               5                   10                  15

Leu Asn Ser His Asn Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Gln Cys
65

<210> SEQ ID NO 305
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 305

Glu Thr Lys Val Ala Tyr Ile Tyr Leu Lys Gln Gly Arg Thr Val Lys
1               5                   10                  15

Leu Asn Ser His Asn Phe Asp Trp Gln Thr Pro Glu Pro Lys Leu Gly
            20                  25                  30

```
Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 306
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 306

Glu Thr Lys Val Ala Tyr His Tyr Leu Lys Gln Gly Arg Thr Val Lys
 1               5                  10                  15

Leu Asn Ser His Asn Phe Asp Trp Gln Thr Pro Glu Pro Lys Leu Gly
                 20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Gln Cys
 65

<210> SEQ ID NO 307
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 307

Glu Thr Lys Val Val Tyr Gly Tyr Leu Lys Glu Gly Arg Thr Val Lys
 1               5                  10                  15

Leu Asp Ser His Arg Phe Asp Trp Gln Thr Pro Glu Pro Lys Leu Gly
                 20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
 50                  55                  60

Lys Asp Cys
 65

<210> SEQ ID NO 308
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 308

Glu Thr Lys Val Val Tyr Ile Tyr Leu Lys Glu Gly Arg Thr Val Lys
 1               5                  10                  15

Leu Asp Ser His Arg Phe Asp Trp Gln Thr Pro Glu Pro Lys Leu Gly
                 20                  25                  30

Phe Lys Asp Gly Gly Gly Gly Lys Asp Gly Thr Lys Val Glu Phe
         35                  40                  45

Lys Ala Asp Lys Phe Glu Trp Asn Ser Pro Asp Phe Arg Ile Ile Phe
```

Lys Asp Cys
65

<210> SEQ ID NO 309
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 309

Glu Thr Lys Val Val Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Asp Cys
65

<210> SEQ ID NO 310
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 310

Glu Thr Lys Val Ala Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Asp Cys
65

<210> SEQ ID NO 311
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 311

Glu Thr Lys Val Ala Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Asp Cys
65

<210> SEQ ID NO 312
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 312

```
Glu Thr Lys Val Ala Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Asp Cys
65
```

<210> SEQ ID NO 313
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 313

```
Glu Thr Lys Val Val Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Asp Cys
65
```

<210> SEQ ID NO 314
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 314

```
Glu Thr Lys Val Val Tyr Ile Tyr Leu Lys Asn Gly Arg Thr Val Lys
1               5                   10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Ile Phe
        50                  55                  60

Lys Asp Cys
65
```

<210> SEQ ID NO 315
<211> LENGTH: 67

<212> TYPE: PRT
<213> ORGANISM: Artificial Sequence
<220> FEATURE:
<223> OTHER INFORMATION: Anaplasma antigenic peptide

<400> SEQUENCE: 315

Glu Thr Lys Val Val Tyr His Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Asp Cys
65

<210> SEQ ID NO 316
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 316

Glu Thr Lys Val Ala Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Ile Phe
    50                  55                  60

Lys Asp Cys
65

<210> SEQ ID NO 317
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 317

Glu Thr Lys Val Val Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
    50                  55                  60

Lys Asp Cys
65

<210> SEQ ID NO 318
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 318

Glu Thr Lys Val Val Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
    50                  55                  60

Lys Asp Cys
65

<210> SEQ ID NO 319
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 319

Glu Thr Lys Val Val Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
    50                  55                  60

Lys Asp Cys
65

<210> SEQ ID NO 320
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 320

Glu Thr Lys Val Ala Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
    50                  55                  60

Lys Asp Cys
65

<210> SEQ ID NO 321
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 321

Glu Thr Lys Val Ala Tyr Ile Tyr Leu Lys Glu Gly Arg Thr Val Lys

```
                1               5                   10                  15
Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Val Phe
        50                  55                  60

Lys Asp Cys
65

<210> SEQ ID NO 322
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 322

Glu Thr Lys Val Ala Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Val Phe
        50                  55                  60

Lys Asp Cys
65

<210> SEQ ID NO 323
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 323

Glu Thr Lys Val Val Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
                20                  25                  30

Phe Lys Asp Gly Gly Gly Gly Lys Asp Gly Thr Lys Val Glu Phe
            35                  40                  45

Lys Ala Asp Lys Phe Glu Trp Asn Ser Pro Asp Phe Arg Ile Val Phe
        50                  55                  60

Lys Asp Cys
65

<210> SEQ ID NO 324
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 324

Glu Thr Lys Val Val Tyr Ile Tyr Leu Lys Asn Gly Arg Thr Val Lys
1               5                   10                  15

Leu Asp Ser His Arg Phe Asp Trp Gln Thr Pro Glu Pro Lys Leu Gly
                20                  25                  30
```

```
Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
 50                  55                  60

Lys Asp Cys
 65

<210> SEQ ID NO 325
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 325

Glu Thr Lys Val Val Tyr His Tyr Leu Lys Asn Gly Arg Thr Val Lys
 1               5                  10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
 50                  55                  60

Lys Asp Cys
 65

<210> SEQ ID NO 326
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 326

Glu Thr Lys Val Ala Tyr Gly Tyr Leu Lys Asn Gly Arg Thr Val Lys
 1               5                  10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Phe Arg Ile Val Phe
 50                  55                  60

Lys Asp Cys
 65

<210> SEQ ID NO 327
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 327

Glu Thr Lys Val Val Tyr Gly Tyr Leu Lys Glu Gly Arg Thr Val Lys
 1               5                  10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45
```

Lys Ala Asp Lys Phe Glu Trp Asn Ser Pro Asp Trp Arg Ile Val Phe
    50                  55                  60

Lys Asp Cys
65

<210> SEQ ID NO 328
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 328

Glu Thr Lys Val Val Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Trp Arg Ile Val Phe
    50                  55                  60

Lys Asp Cys
65

<210> SEQ ID NO 329
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 329

Glu Thr Lys Val Val Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Trp Arg Ile Val Phe
    50                  55                  60

Lys Asp Cys
65

<210> SEQ ID NO 330
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 330

Glu Thr Lys Val Ala Tyr Gly Tyr Leu Lys Gly Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asp Lys Phe Glu Trp Asn Ser Pro Asp Trp Arg Ile Val Phe
    50                  55                  60

Lys Asp Cys

<210> SEQ ID NO 331
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 331

```
Glu Thr Lys Val Ala Tyr Ile Tyr Leu Lys Glu Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Ser Pro Asp Trp Arg Ile Val Phe
    50                  55                  60
Lys Asp Cys
65
```

<210> SEQ ID NO 332
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 332

```
Glu Thr Lys Val Ala Tyr His Tyr Leu Lys Glu Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Ser Pro Asp Trp Arg Ile Val Phe
    50                  55                  60
Lys Asp Cys
65
```

<210> SEQ ID NO 333
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 333

```
Glu Thr Lys Val Val Tyr Gly Tyr Leu Lys Asn Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Ser Pro Asp Trp Arg Ile Val Phe
    50                  55                  60
Lys Asp Cys
65
```

<210> SEQ ID NO 334

<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 334

Glu Thr Lys Val Val Tyr Ile Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly G

<223> OTHER INFORMATION: Anaplasma antigenic peptide

<400> SEQUENCE: 337

```
Glu Thr Lys Val Val Tyr Gly Tyr Leu Lys Glu Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Gln Pro Asp Trp Arg Ile Val Phe
    50                  55                  60
Lys Asp Cys
65
```

<210> SEQ ID NO 338
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 338

```
Glu Thr Lys Val Val Tyr Ile Tyr Leu Lys Glu Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Gln Pro Asp Trp Arg Ile Val Phe
    50                  55                  60
Lys Asp Cys
65
```

<210> SEQ ID NO 339
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 339

```
Glu Thr Lys Val Val Tyr His Tyr Leu Lys Glu Gly Arg Thr Val Lys
1               5                   10                  15
Leu Asp Ser His Arg Phe Asp Trp Gln Thr Pro Glu Pro Lys Leu Gly
            20                  25                  30
Phe Lys Asp Gly Gly Gly Gly Lys Asp Gly Thr Lys Val Glu Phe
        35                  40                  45
Lys Ala Asp Lys Phe Glu Trp Asn Gln Pro Asp Trp Arg Ile Val Phe
    50                  55                  60
Lys Asp Cys
65
```

<210> SEQ ID NO 340
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 340

```
Glu Thr Lys Val Ala Tyr Gly Tyr Leu Lys Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Gln Pro Asp Trp Arg Ile Val Phe
        50                  55                  60

Lys Asp Cys
65

<210> SEQ ID NO 341
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 341

Glu Thr Lys Val Ala Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Gln Pro Asp Trp Arg Ile Val Phe
        50                  55                  60

Lys Asp Cys
65

<210> SEQ ID NO 342
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 342

Glu Thr Lys Val Ala Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
            35                  40                  45

Lys Ala Asp Lys Phe Glu Trp Asn Gln Pro Asp Trp Arg Ile Val Phe
        50                  55                  60

Lys Asp Cys
65

<210> SEQ ID NO 343
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 343

Glu Thr Lys Val Val Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
```

20                  25                  30

Phe Lys Asp Gly Gly Gly Gly Gly Lys Asp Gly Thr Lys Val Glu Phe
            35

```
Lys Ala Asp Lys Phe Glu Trp Asn Gln Pro Asp Trp Arg Ile Val Phe
         50                  55                  60

Lys Asp Cys
65

<210> SEQ ID NO 347
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 347

Glu Thr Lys Val Val Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asp Lys Phe Gln Trp Asn Gln Pro Asp Trp Arg Ile Val Phe
         50                  55                  60

Lys Asp Cys
65

<210> SEQ ID NO 348
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 348

Glu Thr Lys Val Val Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asp Lys Phe Gln Trp Asn Gln Pro Asp Trp Arg Ile Val Phe
         50                  55                  60

Lys Asp Cys
65

<210> SEQ ID NO 349
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 349

Glu Thr Lys Val Val Tyr Gly Tyr Leu Lys Gly Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Gly Lys Asp Gly Thr Lys Val Glu Phe
        35                  40                  45

Lys Ala Asn Lys Phe Gln Trp Asn Gln Pro Asp Trp Arg Ile Val Phe
         50                  55                  60
```

-continued

Lys Asp Cys
65

<210> SEQ ID NO 350
<211> LENGTH: 67
<212> TYPE: PRT
<213> ORGANISM: Artificial Sequence
<220> FEATURE:
<223> OTHER INFORMATION: Anaplasma antigenic peptide

<400> SEQUENCE: 350

Glu Thr Lys Val Val Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Gly Gly Gly Gly Lys Asp Gly Thr Lys Val Glu Phe
        35                  40                  45

Lys Ala Asn Lys Phe Gln Trp Asn Gln Pro Asp Trp Arg Ile Val Phe
    50                  55                  60

Lys Asp Cys
65

<210> SEQ ID NO 351
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 351

Cys Lys Asp Gly Thr Lys Val Glu Phe Lys Ala Asp Lys Phe Glu Trp
1               5                   10                  15

Asn Ser Pro Asp Phe Arg Ile Ile Phe Lys Gln
            20                  25

<210> SEQ ID NO 352
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 352

Cys Lys Asp Gly Thr Lys Val Glu Val Lys Ala Asp Lys Phe Glu Trp
1               5                   10                  15

Asn Ser Pro Asp Phe Arg Ile Ile Phe Lys Gln
            20                  25

<210> SEQ ID NO 353
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 353

Cys Lys Asp Gly Thr Gln Val Glu Phe Lys Ala Asp Lys Phe Glu Trp
1               5                   10                  15

Asn Ser Pro Asp Phe Arg Ile Ile Phe Lys Gln
            20                  25

<210> SEQ ID NO 354
<211> LENGTH: 27

```
<212> TYPE: PRT
<213> ORGANISM: Artificial Sequence
<220> FEATURE:
<223> OTHER INFORMATION: Anaplasma antigenic peptide

<400> SEQUENCE: 354

Cys Lys Asp Gly Thr Gln Val Glu Val Lys Ala Asp Lys Phe Glu Trp
1               5                   10                  15

Asn Ser Pro Asp Phe Arg Ile Ile Phe Lys Gln
            20                  25

<210> SEQ ID NO 355
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 355

Cys Lys Asp Gly Thr Lys Val Glu Phe Lys Ala Asn Lys Phe Glu Trp
1               5                   10                  15

Asn Ser Pro Asp Phe Arg Ile Ile Phe Lys Gln
            20                  25

<210> SEQ ID NO 356
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 356

Cys Lys Asp Gly Thr Lys Val Glu Val Lys Ala Asn Lys Phe Glu Trp
1               5                   10                  15

Asn Ser Pro Asp Phe Arg Ile Ile Phe Lys Gln
            20                  25

<210> SEQ ID NO 357
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 357

Cys Lys Asp Gly Thr Gln Val Glu Phe Lys Ala Asn Lys Phe Glu Trp
1               5                   10                  15

Asn Ser Pro Asp Phe Arg Ile Ile Phe Lys Gln
            20                  25

<210> SEQ ID NO 358
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 358

Cys Lys Asp Gly Thr Gln Val Glu Val Lys Ala Asn Lys Phe Glu Trp
1               5                   10                  15

Asn Ser Pro Asp Phe Arg Ile Ile Phe Lys Gln
            20                  25

<210> SEQ ID NO 359
```

<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 359

Cys Lys Asp Gly Thr Lys Val Glu Phe Lys Ala Asp Lys Phe Gln Trp
1               5                   10                  15

Asn Ser Pro Asp Phe Arg Ile Ile Phe Lys Gln
            20                  25

<210> SEQ ID NO 360
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 360

Cys Lys Asp Gly Thr Lys Val Glu Val Lys Ala Asp Lys Phe Gln Trp
1               5                   10                  15

Asn Ser Pro Asp Phe Arg Ile Ile Phe Lys Gln
            20                  25

<210> SEQ ID NO 361
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 361

Cys Lys Asp Gly Thr Gln Val Glu Phe Lys Ala Asp Lys Phe Gln Trp
1               5                   10                  15

Asn Ser Pro Asp Phe Arg Ile Ile Phe Lys Gln
            20                  25

<210> SEQ ID NO 362
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 362

Cys Lys Asp Gly Thr Gln Val Glu Val Lys Ala Asp Lys Phe Gln Trp
1               5                   10                  15

Asn Ser Pro Asp Phe Arg Ile Ile Phe Lys Gln
            20                  25

<210> SEQ ID NO 363
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 363

Cys Lys Asp Gly Thr Lys Val Glu Phe Lys Ala Asn Lys Phe Gln Trp
1               5                   10                  15

Asn Ser Pro Asp Phe Arg Ile Ile Phe Lys Gln
            20                  25

<210> SEQ ID NO 364
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 364

Cys Lys Asp Gly Thr Lys Val Glu Val Lys Ala Asn Lys Phe Gln Trp
1               5                   10                  15

Asn Ser Pro Asp Phe Arg Ile Ile Phe Lys Gln
            20                  25

<210> SEQ ID NO 365
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 365

Cys Lys Asp Gly Thr Gln Val Glu Phe Lys Ala Asn Lys Phe Gln Trp
1               5                   10                  15

Asn Ser Pro Asp Phe Arg Ile Ile Phe Lys Gln
            20                  25

<210> SEQ ID NO 366
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 366

Cys Lys Asp Gly Thr Gln Val Glu Val Lys Ala Asn Lys Phe Gln Trp
1               5                   10                  15

Asn Ser Pro Asp Phe Arg Ile Ile Phe Lys Gln
            20                  25

<210> SEQ ID NO 367
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 367

Cys Lys Asp Gly Thr Lys Val Glu Phe Lys Ala Asp Lys Phe Gln Trp
1               5                   10                  15

Asn Gln Pro Asp Phe Arg Ile Ile Phe Lys Gln
            20                  25

<210> SEQ ID NO 368
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 368

Cys Lys Asp Gly Thr Lys Val Glu Val Lys Ala Asp Lys Phe Gln Trp
1               5                   10                  15

Asn Gln Pro Asp Phe Arg Ile Ile Phe Lys Gln
            20                  25

<210> SEQ ID NO 369
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 369

Cys Lys Asp Gly Thr Gln Val Glu Phe Lys Ala Asp Lys Phe Gln Trp
1               5                   10                  15

Asn Gln Pro Asp Phe Arg Ile Ile Phe Lys Gln
            20                  25

<210> SEQ ID NO 370
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 370

Cys Lys Asp Gly Thr Gln Val Glu Val Lys Ala Asp Lys Phe Gln Trp
1               5                   10                  15

Asn Gln Pro Asp Phe Arg Ile Ile Phe Lys Gln
            20                  25

<210> SEQ ID NO 371
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 371

Cys Lys Asp Gly Thr Lys Val Glu Phe Lys Ala Asn Lys Phe Gln Trp
1               5                   10                  15

Asn Gln Pro Asp Phe Arg Ile Ile Phe Lys Gln
            20                  25

<210> SEQ ID NO 372
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 372

Cys Lys Asp Gly Thr Lys Val Glu Val Lys Ala Asn Lys Phe Gln Trp
1               5                   10                  15

Asn Gln Pro Asp Phe Arg Ile Ile Phe Lys Gln
            20                  25

<210> SEQ ID NO 373
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 373

Cys Lys Asp Gly Thr Gln Val Glu Phe Lys Ala Asn Lys Phe Gln Trp
1               5                   10                  15

Asn Gln Pro Asp Phe Arg Ile Ile Phe Lys Gln
            20                  25

<210> SEQ ID NO 374
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 374

Cys Lys Asp Gly Thr Gln Val Glu Val Lys Ala Asn Lys Phe Gln Trp
1               5                   10                  15

Asn Gln Pro Asp Phe Arg Ile Ile Phe Lys Gln
            20                  25

<210> SEQ ID NO 375
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 375

Cys Lys Asp Gly Thr Lys Val Glu Phe Lys Ala Asp Lys Phe Gln Trp
1               5                   10                  15

Asn Gln Pro Asp Trp Arg Ile Ile Phe Lys Gln
            20                  25

<210> SEQ ID NO 376
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 376

Cys Lys Asp Gly Thr Lys Val Glu Val Lys Ala Asp Lys Phe Gln Trp
1               5                   10                  15

Asn Gln Pro Asp Trp Arg Ile Ile Phe Lys Gln
            20                  25

<210> SEQ ID NO 377
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 377

Cys Lys Asp Gly Thr Gln Val Glu Phe Lys Ala Asp Lys Phe Gln Trp
1               5                   10                  15

Asn Gln Pro Asp Trp Arg Ile Ile Phe Lys Gln
            20                  25

<210> SEQ ID NO 378
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 378

Cys Lys Asp Gly Thr Gln Val Glu Val Lys Ala Asp Lys Phe Gln Trp
1               5                   10                  15

Asn Gln Pro Asp Trp Arg Ile Ile Phe Lys Gln

```
                20                  25

<210> SEQ ID NO 379
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 379

Cys Lys Asp Gly Thr Lys Val Glu Phe Lys Ala Asn Lys Phe Gln Trp
1               5                   10                  15

Asn Gln Pro Asp Trp Arg Ile Ile Phe Lys Gln
            20                  25

<210> SEQ ID NO 380
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 380

Cys Lys Asp Gly Thr Lys Val Glu Val Lys Ala Asn Lys Phe Gln Trp
1               5                   10                  15

Asn Gln Pro Asp Trp Arg Ile Ile Phe Lys Gln
            20                  25

<210> SEQ ID NO 381
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 381

Cys Lys Asp Gly Thr Gln Val Glu Phe Lys Ala Asn Lys Phe Gln Trp
1               5                   10                  15

Asn Gln Pro Asp Trp Arg Ile Ile Phe Lys Gln
            20                  25

<210> SEQ ID NO 382
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 382

Cys Lys Asp Gly Thr Gln Val Glu Val Lys Ala Asn Lys Phe Gln Trp
1               5                   10                  15

Asn Gln Pro Asp Trp Arg Ile Ile Phe Lys Gln
            20                  25

<210> SEQ ID NO 383
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 383

Cys Lys Asp Gly Thr Lys Val Glu Phe Lys Ala Asp Lys Phe Gln Trp
1               5                   10                  15
```

Asn Gln Pro Asp Trp Arg Ile Val Phe Lys Gln
            20                  25

<210> SEQ ID NO 384
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 384

Cys Lys Asp Gly Thr Lys Val Glu Val Lys Ala Asp Lys Phe Gln Trp
1               5                   10                  15

Asn Gln Pro Asp Trp Arg Ile Val Phe Lys Gln
            20                  25

<210> SEQ ID NO 385
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 385

Cys Lys Asp Gly Thr Gln Val Glu Phe Lys Ala Asp Lys Phe Gln Trp
1               5                   10                  15

Asn Gln Pro Asp Trp Arg Ile Val Phe Lys Gln
            20                  25

<210> SEQ ID NO 386
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 386

Cys Lys Asp Gly Thr Gln Val Glu Val Lys Ala Asp Lys Phe Gln Trp
1               5                   10                  15

Asn Gln Pro Asp Trp Arg Ile Val Phe Lys Gln
            20                  25

<210> SEQ ID NO 387
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 387

Cys Lys Asp Gly Thr Lys Val Glu Phe Lys Ala Asn Lys Phe Gln Trp
1               5                   10                  15

Asn Gln Pro Asp Trp Arg Ile Val Phe Lys Gln
            20                  25

<210> SEQ ID NO 388
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 388

Cys Lys Asp Gly Thr Lys Val Glu Val Lys Ala Asn Lys Phe Gln Trp
1               5                   10                  15

Asn Gln Pro Asp Trp Arg Ile Val Phe Lys Gln
            20                  25

<210> SEQ ID NO 389
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 389

Cys Lys Asp Gly Thr Gln Val Glu Phe Lys Ala Asn Lys Phe Gln Trp
1               5                   10                  15

Asn Gln Pro Asp Trp Arg Ile Val Phe Lys Gln
            20                  25

<210> SEQ ID NO 390
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 390

Cys Lys Asp Gly Thr Gln Val Glu Val Lys Ala Asn Lys Phe Gln Trp
1               5                   10                  15

Asn Gln Pro Asp Trp Arg Ile Val Phe Lys Gln
            20                  25

<210> SEQ ID NO 391
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 391

Cys Lys Asp Gly Thr Lys Val Glu Phe Lys Ala Asp Lys Phe Gln Trp
1               5                   10                  15

Asn Gln Pro Asp Trp Arg Ile Val Phe Lys Asp
            20                  25

<210> SEQ ID NO 392
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 392

Cys Lys Asp Gly Thr Lys Val Glu Val Lys Ala Asp Lys Phe Gln Trp
1               5                   10                  15

Asn Gln Pro Asp Trp Arg Ile Val Phe Lys Asp
            20                  25

<210> SEQ ID NO 393
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 393

Cys Lys Asp Gly Thr Gln Val Glu Phe Lys Ala Asp Lys Phe Gln Trp

```
                1               5                  10                  15
Asn Gln Pro Asp Trp Arg Ile Val Phe Lys Asp
            20                  25

<210> SEQ ID NO 394
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 394

Cys Lys Asp Gly Thr Gln Val Glu Val Lys Ala Asp Lys Phe Gln Trp
1               5                   10                  15

Asn Gln Pro Asp Trp Arg Ile Val Phe Lys Asp
            20                  25

<210> SEQ ID NO 395
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 395

Cys Lys Asp Gly Thr Lys Val Glu Phe Lys Ala Asn Lys Phe Gln Trp
1               5                   10                  15

Asn Gln Pro Asp Trp Arg Ile Val Phe Lys Asp
            20                  25

<210> SEQ ID NO 396
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 396

Cys Lys Asp Gly Thr Lys Val Glu Val Lys Ala Asn Lys Phe Gln Trp
1               5                   10                  15

Asn Gln Pro Asp Trp Arg Ile Val Phe Lys Asp
            20                  25

<210> SEQ ID NO 397
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 397

Cys Lys Asp Gly Thr Gln Val Glu Phe Lys Ala Asn Lys Phe Gln Trp
1               5                   10                  15

Asn Gln Pro Asp Trp Arg Ile Val Phe Lys Asp
            20                  25

<210> SEQ ID NO 398
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 398
```

```
Cys Lys Asp Gly Thr Gln Val Glu Val Lys Ala Asn Lys Phe Gln Trp
1               5                   10                  15

Asn Gln Pro Asp Trp Arg Ile Val Phe Lys Asp
            20                  25
```

<210> SEQ ID NO 399
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 399

```
Cys Ile Gly Gly Lys Ser Pro Ala Arg Ser Thr Glu Glu Arg Val Ala
1               5                   10                  15

Gly Asp Leu Asp His Lys Glu Val Asp Ser Asp Lys Lys His Asp Ala
            20                  25                  30

Glu Lys Thr Glu Glu Lys Arg His
        35                  40
```

<210> SEQ ID NO 400
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 400

```
Cys Ile Gly Gly Lys Ser Pro Ala Arg Tyr Thr Glu Glu Arg Val Ala
1               5                   10                  15

Gly Asp Leu Asp His Lys Glu Val Asp Ser Asp Lys Lys His Asp Ala
            20                  25                  30

Glu Lys Thr Glu Glu Lys Arg His
        35                  40
```

<210> SEQ ID NO 401
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 401

```
Cys Val Gly Gly Lys Ser Pro Ala Arg Ser Thr Glu Glu Arg Val Ala
1               5                   10                  15

Gly Asp Leu Asp His Lys Glu Val Asp Ser Asp Lys Lys His Asp Ala
            20                  25                  30

Glu Lys Thr Glu Glu Lys Arg His
        35                  40
```

<210> SEQ ID NO 402
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 402

```
Cys Val Gly Gly Lys Ser Pro Ala Arg Tyr Thr Glu Glu Arg Val Ala
1               5                   10                  15

Gly Asp Leu Asp His Lys Glu Val Asp Ser Asp Lys Lys His Asp Ala
            20                  25                  30
```

Glu Lys Thr Glu Glu Lys Arg His
        35                  40

<210> SEQ ID NO 403
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 403

Cys Ile Gly Gly Lys Ser Pro Ala Arg Ser Thr Glu Glu Arg Val Ala
1               5                   10                  15

Gly Asp Leu Asp His Lys Asn Val Asp Ser Asp Lys Lys His Asp Ala
            20                  25                  30

Glu Lys Thr Glu Glu Lys Arg His
        35                  40

<210> SEQ ID NO 404
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 404

Cys Ile Gly Gly Lys Ser Pro Ala Arg Tyr Thr Glu Glu Arg Val Ala
1               5                   10                  15

Gly Asp Leu Asp His Lys Asn Val Asp Ser Asp Lys Lys His Asp Ala
            20                  25                  30

Glu Lys Thr Glu Glu Lys Arg His
        35                  40

<210> SEQ ID NO 405
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 405

Cys Val Gly Gly Lys Ser Pro Ala Arg Ser Thr Glu Glu Arg Val Ala
1               5                   10                  15

Gly Asp Leu Asp His Lys Asn Val Asp Ser Asp Lys Lys His Asp Ala
            20                  25                  30

Glu Lys Thr Glu Glu Lys Arg His
        35                  40

<210> SEQ ID NO 406
<211> LENGTH: 40
<212> TYPE: PRT
<213> ORGANISM: Artificial Sequence
<220> FEATURE:
<223> OTHER INFORMATION: Anaplasma antigenic peptide

<400> SEQUENCE: 406

Cys Val Gly Gly Lys Ser Pro Ala Arg Tyr Thr Glu Glu Arg Val Ala
1               5                   10                  15

Gly Asp Leu Asp His Lys Asn Val Asp Ser Asp Lys Lys His Asp Ala
            20                  25                  30

Glu Lys Thr Glu Glu Lys Arg His
        35                  40

<210> SEQ ID NO 407
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 407

Cys Lys Asp Gly Ser Arg Val Glu Phe Lys Ala Glu Arg Phe Asn Trp
1               5                   10                  15

Gln Ser Pro Asn Pro Lys Ile Lys Tyr Arg Asn
            20                  25

<210> SEQ ID NO 408
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 408

Cys Lys Asp Gly Ser Arg Val Glu Tyr Lys Ala Glu Arg Phe Asn Trp
1               5                   10                  15

Gln Ser Pro Asn Pro Lys Ile Lys Tyr Arg Asn
            20                  25

<210> SEQ ID NO 409
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 409

Cys Lys Asp Gly Gln Arg Val Glu Phe Lys Ala Glu Arg Phe Asn Trp
1               5                   10                  15

Gln Ser Pro Asn Pro Lys Ile Lys Tyr Arg Asn
            20                  25

<210> SEQ ID NO 410
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 410

Cys Lys Asp Gly Gln Arg Val Glu Tyr Lys Ala Glu Arg Phe Asn Trp
1               5                   10                  15

Gln Ser Pro Asn Pro Lys Ile Lys Tyr Arg Asn
            20                  25

<210> SEQ ID NO 411
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 411

Cys Lys Asp Gly Ser Arg Val Glu Phe Lys Ala Glu His Phe Asn Trp
1               5                   10                  15

Gln Ser Pro Asn Pro Lys Ile Lys Tyr Arg Asn
            20                  25

<210> SEQ ID NO 412
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 412

Cys Lys Asp Gly Ser Arg Val Glu Tyr Lys Ala Glu His Phe Asn Trp
1               5                   10                  15

Gln Ser Pro Asn Pro Lys Ile Lys Tyr Arg Asn
            20                  25

<210> SEQ ID NO 413
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 413

Cys Lys Asp Gly Gln Arg Val Glu Phe Lys Ala Glu His Phe Asn Trp
1               5                   10                  15

Gln Ser Pro Asn Pro Lys Ile Lys Tyr Arg Asn
            20                  25

<210> SEQ ID NO 414
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 414

Cys Lys Asp Gly Gln Arg Val Glu Tyr Lys Ala Glu His Phe Asn Trp
1               5                   10                  15

Gln Ser Pro Asn Pro Lys Ile Lys Tyr Arg Asn
            20                  25

<210> SEQ ID NO 415
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 415

Cys Lys Asp Gly Ser Arg Val Glu Phe Lys Ala Glu Arg Phe Asn Tyr
1               5                   10                  15

Gln Ser Pro Asn Pro Lys Ile Lys Tyr Arg Asn
            20                  25

<210> SEQ ID NO 416
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 416

Cys Lys Asp Gly Ser Arg Val Glu Tyr Lys Ala Glu Arg Phe Asn Tyr
1               5                   10                  15

Gln Ser Pro Asn Pro Lys Ile Lys Tyr Arg Asn

```
                20                  25

<210> SEQ ID NO 417
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 417

Cys Lys Asp Gly Gln Arg Val Glu Phe Lys Ala Glu Arg Phe Asn Tyr
1               5                   10                  15

Gln Ser Pro Asn Pro Lys Ile Lys Tyr Arg Asn
            20                  25

<210> SEQ ID NO 418
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 418

Cys Lys Asp Gly Gln Arg Val Glu Tyr Lys Ala Glu Arg Phe Asn Tyr
1               5                   10                  15

Gln Ser Pro Asn Pro Lys Ile Lys Tyr Arg Asn
            20                  25

<210> SEQ ID NO 419
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 419

Cys Lys Asp Gly Ser Arg Val Glu Phe Lys Ala Glu His Phe Asn Tyr
1               5                   10                  15

Gln Ser Pro Asn Pro Lys Ile Lys Tyr Arg Asn
            20                  25

<210> SEQ ID NO 420
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 420

Cys Lys Asp Gly Ser Arg Val Glu Tyr Lys Ala Glu His Phe Asn Tyr
1               5                   10                  15

Gln Ser Pro Asn Pro Lys Ile Lys Tyr Arg Asn
            20                  25

<210> SEQ ID NO 421
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 421

Cys Lys Asp Gly Gln Arg Val Glu Phe Lys Ala Glu His Phe Asn Tyr
1               5                   10                  15
```

Gln Ser Pro Asn Pro Lys Ile Lys Tyr Arg Asn
            20                  25

<210> SEQ ID NO 422
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 422

Cys Lys Asp Gly Gln Arg Val Glu Tyr Lys Ala Glu His Phe Asn Tyr
1               5                   10                  15

Gln Ser Pro Asn Pro Lys Ile Lys Tyr Arg Asn
            20                  25

<210> SEQ ID NO 423
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 423

Cys Lys Asp Gly Ser Arg Val Glu Phe Lys Ala Glu Arg Phe Asn Trp
1               5                   10                  15

Gln Gln Pro Asn Pro Lys Ile Lys Tyr Arg Asn
            20                  25

<210> SEQ ID NO 424
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 424

Cys Lys Asp Gly Ser Arg Val Glu Tyr Lys Ala Glu Arg Phe Asn Trp
1               5                   10                  15

Gln Gln Pro Asn Pro Lys Ile Lys Tyr Arg Asn
            20                  25

<210> SEQ ID NO 425
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 425

Cys Lys Asp Gly Gln Arg Val Glu Phe Lys Ala Glu Arg Phe Asn Trp
1               5                   10                  15

Gln Gln Pro Asn Pro Lys Ile Lys Tyr Arg Asn
            20                  25

<210> SEQ ID NO 426
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 426

Cys Lys Asp Gly Gln Arg Val Glu Tyr Lys Ala Glu Arg Phe Asn Trp
1               5                   10                  15

Gln Gln Pro Asn Pro Lys Ile Lys Tyr Arg Asn
            20                  25

<210> SEQ ID NO 427
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 427

Cys Lys Asp Gly Ser Arg Val Glu Phe Lys Ala Glu His Phe Asn Trp
1               5                   10                  15

Gln Gln Pro Asn Pro Lys Ile Lys Tyr Arg Asn
            20                  25

<210> SEQ ID NO 428
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 428

Cys Lys Asp Gly Ser Arg Val Glu Tyr Lys Ala Glu His Phe Asn Trp
1               5                   10                  15

Gln Gln Pro Asn Pro Lys Ile Lys Tyr Arg Asn
            20                  25

<210> SEQ ID NO 429
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 429

Cys Lys Asp Gly Gln Arg Val Glu Phe Lys Ala Glu His Phe Asn Trp
1               5                   10                  15

Gln Gln Pro Asn Pro Lys Ile Lys Tyr Arg Asn
            20                  25

<210> SEQ ID NO 430
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 430

Cys Lys Asp Gly Gln Arg Val Glu Tyr Lys Ala Glu His Phe Asn Trp
1               5                   10                  15

Gln Gln Pro Asn Pro Lys Ile Lys Tyr Arg Asn
            20                  25

<210> SEQ ID NO 431
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 431

Cys Lys Asp Gly Ser Arg Val Glu Phe Lys Ala Glu Arg Phe Asn Tyr

Gln Gln Pro Asn Pro Lys Ile Lys Tyr Arg Asn
            20                  25

<210> SEQ ID NO 432
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 432

Cys Lys Asp Gly Ser Arg Val Glu Tyr Lys Ala Glu Arg Phe Asn Tyr
1               5                   10                  15

Gln Gln Pro Asn Pro Lys Ile Lys Tyr Arg Asn
            20                  25

<210> SEQ ID NO 433
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 433

Cys Lys Asp Gly Gln Arg Val Glu Phe Lys Ala Glu Arg Phe Asn Tyr
1               5                   10                  15

Gln Gln Pro Asn Pro Lys Ile Lys Tyr Arg Asn
            20                  25

<210> SEQ ID NO 434
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 434

Cys Lys Asp Gly Gln Arg Val Glu Tyr Lys Ala Glu Arg Phe Asn Tyr
1               5                   10                  15

Gln Gln Pro Asn Pro Lys Ile Lys Tyr Arg Asn
            20                  25

<210> SEQ ID NO 435
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 435

Cys Lys Asp Gly Ser Arg Val Glu Phe Lys Ala Glu His Phe Asn Tyr
1               5                   10                  15

Gln Gln Pro Asn Pro Lys Ile Lys Tyr Arg Asn
            20                  25

<210> SEQ ID NO 436
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 436

Cys Lys Asp Gly Ser Arg Val Glu Tyr Lys Ala Glu His Phe Asn Tyr
1               5                   10                  15

Gln Gln Pro Asn Pro Lys Ile Lys Tyr Arg Asn
            20                  25

<210> SEQ ID NO 437
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 437

Cys Lys Asp Gly Gln Arg Val Glu Phe Lys Ala Glu His Phe Asn Tyr
1               5                   10                  15

Gln Gln Pro Asn Pro Lys Ile Lys Tyr Arg Asn
            20                  25

<210> SEQ ID NO 438
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 438

Cys Lys Asp Gly Gln Arg Val Glu Tyr Lys Ala Glu His Phe Asn Tyr
1               5                   10                  15

Gln Gln Pro Asn Pro Lys Ile Lys Tyr Arg Asn
            20                  25

<210> SEQ ID NO 439
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 439

Cys Lys Asp Gly Gln Arg Val Glu Phe Lys Ala Glu His Phe Asn Trp
1               5                   10                  15

Gln Gln Pro Asn Pro His Ile Lys Tyr Arg Asn
            20                  25

<210> SEQ ID NO 440
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 440

Cys Lys Asp Gly Gln Arg Val Glu Tyr Lys Ala Glu His Phe Asn Trp
1               5                   10                  15

Gln Gln Pro Asn Pro His Ile Lys Tyr Arg Asn
            20                  25

<210> SEQ ID NO 441
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 441

Cys Lys Asp Gly Ser Arg Val Glu Phe Lys Ala Glu Arg Phe Asn Tyr
1               5                   10                  15

Gln Gln Pro Asn Pro His Ile Lys Tyr Arg Asn
            20                  25

<210> SEQ ID NO 442
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 442

Cys Lys Asp Gly Ser Arg Val Glu Tyr Lys Ala Glu Arg Phe Asn Tyr
1               5                   10                  15

Gln Gln Pro Asn Pro His Ile Lys Tyr Arg Asn
            20                  25

<210> SEQ ID NO 443
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 443

Cys Lys Asp Gly Gln Arg Val Glu Phe Lys Ala Glu Arg Phe Asn Tyr
1               5                   10                  15

Gln Gln Pro Asn Pro His Ile Lys Tyr Arg Asn
            20                  25

<210> SEQ ID NO 444
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 444

Cys Lys Asp Gly Gln Arg Val Glu Tyr Lys Ala Glu Arg Phe Asn Tyr
1               5                   10                  15

Gln Gln Pro Asn Pro His Ile Lys Tyr Arg Asn
            20                  25

<210> SEQ ID NO 445
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 445

Cys Lys Asp Gly Ser Arg Val Glu Phe Lys Ala Glu His Phe Asn Tyr
1               5                   10                  15

Gln Gln Pro Asn Pro His Ile Lys Tyr Arg Asn
            20                  25

<210> SEQ ID NO 446
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 446

Cys Lys Asp Gly Ser Arg Val Glu Tyr Lys Ala Glu His Phe Asn Tyr
1               5                   10                  15

Gln Gln Pro Asn Pro His Ile Lys Tyr Arg Asn
            20                  25

<210> SEQ ID NO 447
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 447

Cys Lys Asp Gly Gln Arg Val Glu Phe Lys Ala Glu His Phe Asn Tyr
1               5                   10                  15

Gln Gln Pro Asn Pro His Ile Lys Tyr Arg Asn
            20                  25

<210> SEQ ID NO 448
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 448

Cys Lys Asp Gly Gln Arg Val Glu Tyr Lys Ala Glu His Phe Asn Tyr
1               5                   10                  15

Gln Gln Pro Asn Pro His Ile Lys Tyr Arg Asn
            20                  25

<210> SEQ ID NO 449
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 449

Cys Lys Asp Gly Gln Arg Val Glu Phe Lys Ala Glu His Phe Asn Trp
1               5                   10                  15

Gln Gln Pro Asn Pro His Ile Lys Tyr Arg Asp
            20                  25

<210> SEQ ID NO 450
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 450

Cys Lys Asp Gly Gln Arg Val Glu Tyr Lys Ala Glu His Phe Asn Trp
1               5                   10                  15

Gln Gln Pro Asn Pro His Ile Lys Tyr Arg Asp
            20                  25

<210> SEQ ID NO 451
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 451

Cys Lys Asp Gly Ser Arg Val Glu Phe Lys Ala Glu Arg Phe Asn Tyr
1               5                   10                  15

Gln Gln Pro Asn Pro His Ile Lys Tyr Arg Asp
            20                  25

<210> SEQ ID NO 452
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 452

Cys Lys Asp Gly Ser Arg Val Glu Tyr Lys Ala Glu Arg Phe Asn Tyr
1               5                   10                  15

Gln Gln Pro Asn Pro His Ile Lys Tyr Arg Asp
            20                  25

<210> SEQ ID NO 453
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 453

Cys Lys Asp Gly Gln Arg Val Glu Phe Lys Ala Glu Arg Phe Asn Tyr
1               5                   10                  15

Gln Gln Pro Asn Pro His Ile Lys Tyr Arg Asp
            20                  25

<210> SEQ ID NO 454
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 454

Cys Lys Asp Gly Gln Arg Val Glu Tyr Lys Ala Glu Arg Phe Asn Tyr
1               5                   10                  15

Gln Gln Pro Asn Pro His Ile Lys Tyr Arg Asp
            20                  25

<210> SEQ ID NO 455
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 455

Cys Lys Asp Gly Ser Arg Val Glu Phe Lys Ala Glu His Phe Asn Tyr
1               5                   10                  15

Gln Gln Pro Asn Pro His Ile Lys Tyr Arg Asp
            20                  25

<210> SEQ ID NO 456
<211> LENGTH: 27
<212> TYPE: PRT
<213> ORGANISM: Artificial Sequence
<220> FEATURE:

<223> OTHER INFORMATION: Anaplasma antigenic peptide

<400> SEQUENCE: 456

Cys Lys Asp Gly Ser Arg Val Glu Tyr Lys Ala Glu His Phe Asn Tyr
1               5                   10                  15

Gln Gln Pro Asn Pro His Ile Lys Tyr Arg Asp
            20                  25

<210> SEQ ID NO 457
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 457

Cys Lys Asp Gly Gln Arg Val Glu Phe Lys Ala Glu His Phe Asn Tyr
1               5                   10                  15

Gln Gln Pro Asn Pro His Ile Lys Tyr Arg Asp
            20                  25

<210> SEQ ID NO 458
<211> LENGTH: 27
<212> TYPE: PRT
<213> ORGANISM: Artificial Sequence
<220> FEATURE:
<223> OTHER INFORMATION: Anaplasma antigenic peptide

<400> SEQUENCE: 458

Cys Lys Asp Gly Gln Arg Val Glu Tyr Lys Ala Glu His Phe Asn Tyr
1               5                   10                  15

Gln Gln Pro Asn Pro His Ile Lys Tyr Arg Asp
            20                  25

<210> SEQ ID NO 459
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 459

Cys Gly Lys Ile Leu Asn Leu Val Ser Val Ala Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 460
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 460

Cys Gly Lys Ile Leu Asn Leu Val Ser Val Leu Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 461
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 461

Cys Gly Lys Ile Leu Asn Leu Val Ser Leu Ala Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 462
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 462

Cys Gly Lys Ile Leu Asn Leu Val Ser Leu Leu Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 463
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 463

Cys Gly Lys Ile Leu Asn Leu Val Ser Ile Ala Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 464
<211> LENGTH: 31
<212> TYPE: PRT
<213> ORGANISM: Artificial Sequence
<220> FEATURE:
<223> OTHER INFORMATION: Anaplasma antigenic peptide

<400> SEQUENCE: 464

Cys Gly Lys Ile Leu Asn Leu Val Ser Ile Leu Asn Glu Lys Lys Pro
1               5                   10                  15

Pro Glu Ala Pro Ala Ala Asp Glu Ala Ala Gly Pro Ala Thr His
            20                  25                  30

<210> SEQ ID NO 465
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 465

Glu Thr Lys Val Val Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

```
<210> SEQ ID NO 466
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 466

Glu Thr Lys Val Val Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 467
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 467

Glu Thr Lys Val Val Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 468
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 468

Glu Thr Lys Val Ala Tyr Gly Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 469
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 469

Glu Thr Lys Val Ala Tyr Ile Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 470
<211> LENGTH: 36
<212> TYPE: PRT
```

```
<213> ORGANISM: Artificial Sequence
<220> FEATURE:
<223> OTHER INFORMATION: Anaplasma antigenic peptide

<400> SEQUENCE: 470

Glu Thr Lys Val Ala Tyr His Tyr Leu Lys Glu Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 471
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 471

Glu Thr Lys Val Val Tyr Gly Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 472
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 472

Glu Thr Lys Val Val Tyr Ile Tyr Leu Lys Asn Gly Arg Thr Val Lys
1               5                   10

<400> SEQUENCE: 474

Glu Thr Lys Val Ala Gly Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 475
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 475

Glu Thr Lys Val Ala Tyr Ile Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 476
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 476

Glu Thr Lys Val Ala Tyr His Tyr Leu Lys Asn Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 477
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 477

Glu Thr Lys Val Val Tyr Gly Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 478
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 478

```
Glu Thr Lys Val Val Tyr Ile Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 479
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 479

Glu Thr Lys Val Val Tyr His Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 480
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 480

Glu Thr Lys Val Ala Tyr Gly Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 481
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 481

Glu Thr Lys Val Ala Tyr Ile Tyr Leu Lys Gln Gly Arg Thr Val Lys
1               5                   10                  15

Leu Asp Ser His Arg Phe Asp Trp Gln Thr Pro Glu Pro Lys Leu Gly
            20                  25                  30

Phe Lys Asp Cys
        35

<210> SEQ ID NO 482
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 482

Glu Thr Lys Val Ala Tyr His Tyr Leu Lys Gln Gly Arg Thr Val Lys
1               5                   10                  15
```

```
Leu Asp Ser His Arg Phe Asp Trp Gln Thr Pro Glu Pro Lys Leu Gly
            20                  25                  30

Phe Lys Asp Cys
        35

<210> SEQ ID NO 483
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 483

Glu Thr Lys Val Val Tyr Gly Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Cys
        35

<210> SEQ ID NO 484
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 484

Glu Thr Lys Val Val Tyr Ile Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Cys
        35

<210> SEQ ID NO 485
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 485

Glu Thr Lys Val Val Tyr His Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30

Phe Lys Asp Cys
        35

<210> SEQ ID NO 486
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 486

Glu Thr Lys Val Ala Tyr Gly Tyr Leu Lys Gln Gly Arg Thr Val Lys
1               5                   10                  15

Leu Asp Ser His Asp Phe Asp Trp Gln Thr Pro Glu Pro Lys Leu Gly
            20                  25                  30
```

```
Phe Lys Asp Cys
        35

<210> SEQ ID NO 487
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 487

Glu Thr Lys Val Ala Tyr Ile Tyr Leu Lys Gln Gly Arg Thr Val Lys
 1               5                  10                  15

Leu Asp Ser His Asp Phe Asp Trp Gln Thr Pro Glu Pro Lys Leu Gly
            20                  25                  30

Phe Lys Asp Cys
        35

<210> SEQ ID NO 488
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 488

Glu Thr Lys Val Ala Tyr His Tyr Leu Lys Gln Gly Arg Thr Val Lys
 1               5                  10                  15

Leu Asp Ser His Asp Phe Asp Trp Gln Thr Pro Glu Pro Lys Leu Gly
            20                  25                  30

Phe Lys Asp Cys
        35

<210> SEQ ID NO 489
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 489

Glu Thr Lys Val Val Tyr Gly Tyr Leu Lys Gln Gly Arg Thr Val Lys
 1               5                  10                  15

Leu Asp Ser His Asn Phe Asp Trp Gln Thr Pro Glu Pro Lys Leu Gly
            20                  25                  30

Phe Lys Asp Cys
        35

<210> SEQ ID NO 490
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 490

Glu Thr Lys Val Val Tyr Ile Tyr Leu Lys Gln Gly Arg Thr Val Lys
 1               5                  10                  15

Leu Asp Ser His Asn Phe Asp Trp Gln Thr Pro Glu Pro Lys Leu Gly
            20                  25                  30

Phe Lys Asp Cys
        35
```

-continued

<210> SEQ ID NO 491
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 491

Glu Thr Lys Val Val Tyr His Tyr Leu Lys Gln Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Cys
        35

<210> SEQ ID NO 492
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 492

Glu Thr Lys Val Ala Tyr Gly Tyr Leu Lys Gln Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Cys
        35

<210> SEQ ID NO 493
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 493

Glu Thr Lys Val Ala Tyr Ile Tyr Leu Lys Gln Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Cys
        35

<210> SEQ ID NO 494
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 494

Glu Thr Lys Val Ala Tyr His Tyr Leu Lys Gln Gly Arg Thr Val Lys
1               5                   10                  15

Leu Asp Ser His Asn Phe Asp Trp Gln Thr Pro Glu Pro Lys Leu Gly
            20                  25                  30

Phe Lys Asp Cys
        35

<210> SEQ ID NO 495
<211> LENGTH: 36

```
<212> TYPE: PRT
<213> ORGANISM: Artificial Sequence
<220> FEATURE:
<223> OTHER INFORMATION: Anaplasma antigenic peptide

<400> SEQUENCE: 495

Glu Thr Lys Val Val Tyr Gly Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 496
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 496

Glu Thr Lys Val Val Tyr Ile Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 497
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 497

Glu Thr Lys Val Val Tyr His Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 498
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 498

Glu Thr Lys Val Ala Tyr Gly Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 499
<211> LENGTH: 36
<212> TYPE: PRT
<213> ORGANISM: Artificial Sequence
<220> FEATURE:
```

<223> OTHER INFORMATION: Anaplasma antigenic peptide

<400> SEQUENCE: 499

Glu Thr Lys Val Ala Tyr Ile Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 500
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 500

Glu Thr Lys Val Ala Tyr His Tyr Leu Lys Gln Gly Arg Thr Val Lys
1               5                   10                  15

Leu Asp Ser His Asp Phe Asp Trp Asp Thr Pro Glu Pro Lys Leu Gly
            20                  25                  30

Phe Lys Asp Cys
        35

<210> SEQ ID NO 501
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 501

Glu Thr Lys Val Val Tyr Gly Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 502
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 502

Glu Thr Lys Val Val Tyr Ile Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 503
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 503

-continued

Glu Thr Lys Val Val Tyr His Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 504
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 504

Glu Thr Lys Val Ala Tyr Gly Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 505
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 505

Glu Thr Lys Val Ala Tyr Ile Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 506
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 506

Glu Thr Lys Val Ala Tyr His Tyr Leu Lys Gln Gly Arg Thr Val Lys
1               5                   10                  15

Leu Asp Ser His Asn Phe Asp Trp Asp Thr Pro Glu Pro Lys Leu Gly
            20                  25                  30

Phe Lys Asp Cys
        35

<210> SEQ ID NO 507
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 507

Glu Thr Lys Val Val Tyr Gly Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

Phe Lys Asp Cys
        35

<210> SEQ ID NO 508
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 508

Glu Thr Lys Val Val Tyr Ile Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

Phe Lys Asp Cys
        35

<210> SEQ ID NO 509
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 509

Glu Thr Lys Val Val Tyr His Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

Phe Lys Asp Cys
        35

<210> SEQ ID NO 510
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 510

Glu Thr Lys Val Ala Tyr Gly Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

Phe Lys Asp Cys
        35

<210> SEQ ID NO 511
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 511

Glu Thr Lys Val Ala Tyr Ile Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

-continued

Phe Lys Asp Cys
        35

<210> SEQ ID NO 512
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 512

Glu Thr Lys Val Ala Tyr His Tyr Leu Lys Gln Gly Arg Thr Val Lys
1               5                   10                  15

Leu Asp Ser His Asp Phe Asp Trp Glu Thr Pro Glu Pro Lys Leu Gly
            20                  25                  30

Phe Lys Asp Cys
        35

<210> SEQ ID NO 513
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 513

Glu Thr Lys Val Val Tyr Gly Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 514
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 514

Glu Thr Lys Val Val Tyr Ile Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 515
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 515

Glu Thr Lys Val Val Tyr His Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 516
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 516

Glu Thr Lys Val Ala Tyr Gly Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 517
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 517

Glu Thr Lys Val Ala Tyr Ile Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 518
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 518

Glu Thr Lys Val Ala Tyr His Tyr Leu Lys Gln Gly Arg Thr Val Lys
1               5                   10                  15

Leu Asp Ser His Asn Phe Asp Trp Glu Thr Pro Glu Pro Lys Leu Gly
            20                  25                  30

Phe Lys Asp Cys
        35

<210> SEQ ID NO 519
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 519

Glu Thr Lys Val Val Tyr Gly Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 520

```
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 520

Glu Thr Lys Val Val Tyr Ile Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 521
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 521

Glu Thr Lys Val Val Tyr His Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 522
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 522

Glu Thr Lys Val Ala Tyr Gly Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 523
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 523

Glu Thr Lys Val Ala Tyr Ile Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 524
<211> LENGTH: 36
<212> TYPE: PRT
<213> ORGANISM: Artificial Sequence
```

<220> FEATURE:
<223> OTHER INFORMATION: Anaplasma antigenic peptide

<400> SEQUENCE: 524

Glu Thr Lys Val Ala Tyr His Tyr Leu Lys Gln Gly Arg Thr Val Lys
1               5                   10                  15

Leu Asp Ser His Asp Phe Asp Trp Glu Thr Pro Asn Pro Lys Leu Gly
            20                  25                  30

Phe Lys Asp Cys
        35

<210> SEQ ID NO 525
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 525

Glu Thr Lys Val Val Tyr Gly Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 526
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 526

Glu Thr Lys Val Val Tyr Ile Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 527
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 527

Glu Thr Lys Val Val Tyr His Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 528
<211> LENGTH: 36
<212> TYPE: PRT
<213> ORGANISM: Artificial Sequence
<220> FEATURE:
<223> OTHER INFORMATION: Anaplasma antigenic peptide -continued

<400> SEQUENCE: 528

Glu Thr Lys Val Ala Tyr Gly Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 529
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 529

Glu Thr Lys Val Ala Tyr Ile Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 530
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 530

Glu Thr Lys Val Ala Tyr His Tyr Leu Lys Gln Gly Arg Thr Val Lys
1               5                   10                  15

Leu Asp Ser His Asn Phe Asp Trp Glu Thr Pro Asn Pro Lys Leu Gly
            20                  25                  30

Phe Lys Asp Cys
        35

<210> SEQ ID NO 531
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 531

Glu Thr Lys Val Val Tyr Gly Tyr Leu Lys Gln Gly Arg Thr Val Lys
1               5                   10                  15

Leu Asp Ser His Asp Phe Asp Trp Glu Thr Pro Asn Pro Lys Val Gly
            20                  25                  30

Phe Lys Asp Cys
        35

<210> SEQ ID NO 532
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 532

Glu Thr Lys Val Val Tyr Ile Tyr Leu Lys Gln Gly Arg Thr Val Lys

```
                 1               5                  10                 15
Leu Asp Ser His Asp Phe Asp Trp Glu Thr Pro Asn Pro Lys Val Gly
                20                  25                  30

Phe Lys Asp Cys
            35
```

<210> SEQ ID NO 533
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 533

```
Glu Thr Lys Val Val Tyr His Tyr Leu Lys Gln Gly Arg Thr Val Lys
1               5                   10                  15

Leu Asp Ser His Asp Phe Asp Trp Glu Thr Pro Asn Pro Lys Val Gly
                20                  25                  30

Phe Lys Asp Cys
            35
```

<210> SEQ ID NO 534
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 534

```
Glu Thr Lys Val Ala Tyr Gly Tyr Leu Lys Gln Gly Arg Thr Val Lys
1               5                   10                  15

Leu Asp Ser His Asp Phe Asp Trp Glu Thr Pro Asn Pro Lys Val Gly
                20                  25                  30

Phe Lys Asp Cys
            35
```

<210> SEQ ID NO 535
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 535

```
Glu Thr Lys Val Ala Tyr Ile Tyr Leu Lys Gln Gly Arg Thr Val Lys
1               5                   10                  15

Leu Asp Ser His Asp Phe Asp Trp Glu Thr Pro Asn Pro Lys Val Gly
                20                  25                  30

Phe Lys Asp Cys
            35
```

<210> SEQ ID NO 536
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 536

```
Glu Thr Lys Val Ala Tyr His Tyr Leu Lys Gln Gly Arg Thr Val Lys
1               5                   10                  15

Leu Asp Ser His Asp Phe Asp Trp Glu Thr Pro Asn Pro Lys Val Gly
```

```
                    20                  25                  30

Phe Lys Asp Cys
        35

<210> SEQ ID NO 537
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 537

Glu Thr Lys Val Val Tyr Gly Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
        35

<210> SEQ ID NO 538
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 538

Glu Thr Lys Val Val Tyr Ile Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
        35

<210> SEQ ID NO 539
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 539

Glu Thr Lys Val Val Tyr His Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
        35

<210> SEQ ID NO 540
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 540

Glu Thr Lys Val Ala Tyr Gly Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
```

```
<210> SEQ ID NO 541
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 541

Glu Thr Lys Val Ala Tyr Ile Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
        35

<210> SEQ ID NO 542
<211> LENGTH: 36
<212> TYPE: PRT
<213> ORGANISM: Artificial Sequence
<220> FEATURE:
<223> OTHER INFORMATION: Anaplasma antigenic peptide

<400> SEQUENCE: 542

Glu Thr Lys Val Ala Tyr His Tyr Leu Lys Gln Gly Arg Thr Val Lys
1               5                   10                  15

Leu Asp Ser His Asn Phe Asp Trp Glu Thr Pro Asn Pro Lys Val Gly
            20                  25                  30

Phe Lys Asp Cys
        35

<210> SEQ ID NO 543
<211> LENGTH: 35
<212> TYPE: PRT
<213> ORGANISM: Artificial Sequence
<220> FEATURE:
<223> OTHER INFORMATION: Anaplasma antigenic peptide
<220> FEATURE:
<221> NAME/KEY: MISC_FEATURE
<222> LOCATION: (5)..(5)
<223> OTHER INFORMATION: Xaa is Val or Ala
<220> FEATURE:
<221> NAME/KEY: MISC_FEATURE
<222> LOCATION: (7)..(7)
<223> OTHER INFORMATION: Xaa is Gly, Ile or His
<220> FEATURE:
<221> NAME/KEY: MISC_FEATURE
<222> LOCATION: (11)..(11)
<223> OTHER INFORMATION: Xaa is Glu, Asn or Gln
<220> FEATURE:
<221> NAME/KEY: MISC_FEATURE
<222> LOCATION: (18)..(18)
<223> OTHER INFORMATION: Xaa is Asp or Asn
<220> FEATURE:
<221> NAME/KEY: MISC_FEATURE
<222> LOCATION: (21)..(21)
<223> OTHER INFORMATION: Xaa is Arg, Asp or Asn
<220> FEATURE:
<221> NAME/KEY: MISC_FEATURE
<222> LOCATION: (25)..(25)
<223> OTHER INFORMATION: Xaa is Gln, Asp or Glu
<220> FEATURE:
<221> NAME/KEY: MISC_FEATURE
<222> LOCATION: (28)..(28)
<223> OTHER INFORMATION: Xaa is Glu or Asn
<220> FEATURE:
<221> NAME/KEY: MISC_FEATURE
<222> LOCATION: (31)..(31)
<223> OTHER INFORMATION: Xaa is Leu or Val
```

```
<400> SEQUENCE: 543

Glu Thr Lys Val Xaa Tyr Xaa Tyr Leu Lys Xaa Gly Arg Thr Val Lys
1               5                   10                  15

Leu Xaa Ser His Xaa Phe Asp Trp Xaa Thr Pro Xaa Pro Lys Xaa Gly
            20              25                  30

Phe Lys Asp
        35
```

PEPTIDES, DEVICES, AND METHODS FOR THE DETECTION OF *ANAPLASMA* ANTIBODIES

CROSS-REFERENCE TO RELATED APPLICATIONS

This application claims the benefit of U.S. Provisional Application No. 61/929,655, filed Jan. 21, 2014, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ABAX_041_01US_SeqList_ST25.txt, date recorded Jul. 23, 2014, file size 257 kilobytes).

BACKGROUND OF THE INVENTION

*Anaplasma* are a genus of gram-negative bacteria that are obligate intracellular pathogens capable of infecting granulocytes, platelets and erythrocytes in vertebrate hosts. *Anaplasma* bacteria are transmitted to hosts through arthropod vectors, particularly various species of ticks. *A. phagocytophilum* infects neutrophils and causes anaplasmosis in mammals, including humans. The incidence of human granulocytotropic (or granulocytic) anaplasmosis (HGA, formerly known as human granulocytotropic ehrlichiosis) has increased steadily, from 1.4 cases per million persons in 2000 to 6.1 cases per million persons in 2010. *A. phagocytophilum* is transmitted primarily by *Ixodes* spp. of ticks. Because these *Ixodes* species ticks also transmit *Borrelia burgdorferi* (the causative agent of Lyme disease), simultaneous infection with *A. phagocytophilum* and *B. burgdorferi* is common.

*A. platys* causes infectious cyclic thrombocytopenia by infecting platelets and is thought to be transmitted by *Rhipicephalus* and *Dermacentor* spp. ticks. Although dogs are the most common host for *A. platys* infection, infection in other mammals, including cats, impalas, and sheep, have been reported. Co-infection of *A. platys* and *E. canis* due to the common vector of transmission has been known to occur.

Indirect immunofluorescence assays (IFA) and enzyme-linked immunosorbent assays (ELISA) have typically been used to detect *Anaplasma* infection. These assays detect the binding of anti-*Anaplasma* antibodies from a subject's blood, plasma, or serum to infected cells, cell lysates, or partially purified whole *Anaplasma* proteins. However, these assays for detecting anti-*Anaplasma* antibodies are limited in usefulness because of sensitivity and specificity issues directly related to the nature of the *Anaplasma* antigens used in these tests. Although polymerase chain reaction (PCR)-based tests with improved specificity and sensitivity have been developed, there is a continued need in the art for additional sensitive and specific assays for detecting *Anaplasma* antigens and serodiagnosis of anaplasmosis.

SUMMARY OF THE INVENTION

The present invention is based, in part, on the discovery that certain sequence variants of fragments of the *Anaplasma* outer membrane proteins provide for robust detection of an antibody response against *Anaplasma* species. Accordingly, the invention provides compositions, devices, methods, and kits useful for the detection of antibodies that bind to *Anaplasma* antigens and the diagnosis of anaplasmosis.

In one embodiment, the present invention provides populations of peptides capable of binding to antibodies that recognize *Anaplasma* antigens. In certain embodiments, the population of isolated peptides comprises three or more different peptides, wherein each peptide in the population comprises a sequence of Abaxis ID 2, E-T-R-V-A-Y-P-Y-$X_9$-K-D-G-R-T-V-K-$X_{17}$-D-S-H-$X_{21}$-F-D-W-Q-T-P-$X_{28}$-P-K-$X_{31}$-G-F-K-D-C (SEQ ID NO: 1) or a fragment thereof, wherein $X_9$ is an amino acid selected from the group consisting of I, P or H, $X_{17}$ is an amino acid selected from the group consisting of I, W, or Y, $X_{21}$ is an amino acid selected from the group consisting of R, D, or N, $X_{28}$ is an amino acid selected from the group consisting of E or N, and $X_{31}$ is an amino acid selected from the group consisting of L or V. In other embodiments, each peptide in the population comprises a sequence of Abaxis ID 3, I-E-$X_3$-G-Y-E-$X_7$-F-K-T-$X_{11}$-G-I-R-$X_{15}$-S-G-T-K-E-C (SEQ ID NO: 2) or a fragment thereof, wherein $X_3$ is an amino acid selected from the group consisting of L, V or A, $X_7$ is an amino acid selected from the group consisting of K, N or Q, $X_{11}$ is an amino acid selected from the group consisting of R, D, or N, and $X_{15}$ is an amino acid selected from the group consisting of E, N or Q.

In another embodiment of the invention, each peptide in the population comprises a sequence of APL-ID1, E-T-K-V-$X_5$-Y-$X_7$-Y-L-K-$X_{11}$-G-R-T-V-K-L-$X_{18}$-S-H-$X_{21}$-F-D-W-$X_{25}$-T-P-$X_{28}$-P-K-$X_{31}$-G-F-K-D-G-G-G-G-G-K-D-G-T-$X_{45}$-V-E-$X_{48}$-K-A-$X_{51}$-K-F-$X_{54}$-W-N-$X_{57}$-P-D-$X_{60}$-R-I-$X_{63}$-F-K-$X_{66}$-C (SEQ ID NO: 3) or a fragment thereof, wherein $X_5$ is an amino acid selected from the group consisting of V or A, $X_7$ is an amino acid selected from the group consisting of G, I or H, $X_{11}$ is an amino acid selected from the group consisting of E, N, or Q, $X_{18}$ is an amino acid selected from the group consisting of D or N, $X_{21}$ is an amino acid selected from the group consisting of R, D, or N, $X_{25}$ is an amino acid selected from the group consisting of Q, D, or E, $X_{28}$ is an amino acid selected from the group consisting of E or N, $X_{31}$ is an amino acid selected from the group consisting of L or V, $X_{45}$ is an amino acid selected from the group consisting of K or Q, $X_{48}$ is an amino acid selected from the group consisting of F or V, $X_{51}$ is an amino acid selected from the group consisting of D or N, $X_{54}$ is an amino acid selected from the group consisting of E or Q, $X_{57}$ is an amino acid selected from the group consisting of S or Q, $X_{60}$ is an amino acid selected from the group consisting of F or W, $X_{63}$ is an amino acid selected from the group consisting of I or V, and $X_{66}$ is an amino acid selected from the group consisting of Q or D. In yet another embodiment, each peptide in the population comprises a sequence of APL-ID2, C-K-D-G-T-$X_6$-V-E-$X_9$-K-A-$X_{12}$-K-F-$X_{15}$-W-N-$X_{18}$-P-D-$X_{21}$-R-I-$X_{24}$-F-K-$X_{27}$ (SEQ ID NO: 4) or a fragment thereof, wherein $X_6$ is an amino acid selected from the group consisting of K or Q, $X_9$ is an amino acid selected from the group consisting of F or V, $X_{12}$ is an amino acid selected from the group consisting of D or N, $X_{15}$ is an amino acid selected from the group consisting of E or Q, $X_{18}$ is an amino acid selected from the group consisting of S or Q, $X_{21}$ is an amino acid selected from the group consisting of F or W, $X_{24}$ is an amino acid selected from the group consisting of I or V, and $X_{27}$ is an amino acid selected from the group consisting of Q or D. In another embodiment, each peptide in the population comprises a sequence of APL-ID3, C-$X_2$-G-G-K-S-P-A-R-$X_{10}$-T-E-E-R-V-A-G-D-L-D-H-K-$X_{23}$-V-D-S-D-K-K-H-D-A-E-K-T-E-E-K-R-H (SEQ ID NO: 5) or a fragment thereof, wherein $X_2$ is an amino acid selected from the group consisting of I or V, $X_{10}$ is an amino acid selected from the group consisting of S or Y, and $X_{23}$ is an amino acid selected from the group consisting of E or N. In certain embodiments, each peptide in the population comprises a sequence of APL-ID5.1, C-G-K-I-L-N-L-V-S-A-V-Q-E-K-K-P-P-E-A-P-A-A-D-E-A-A-G-P-A-T-H (SEQ ID NO: 6) or a fragment thereof.

In some embodiments of the invention, a population of isolated peptides comprises three or more different peptides, wherein each peptide in the population comprises a sequence of APL-ID6, C-K-D-G-$X_5$-R-V-E-$X_9$-K-A-E-$X_{13}$-F-N-$X_{16}$-Q-$X_{18}$-P-N-P-$X_{22}$-I-K-Y-R-$X_{27}$ (SEQ ID NO: 7) or a fragment thereof, wherein $X_5$ is an amino acid selected from the group consisting of S or Q, $X_9$ is an amino acid selected from the group consisting of F or Y, $X_{13}$ is an amino acid selected from the group consisting of R or H, $X_{16}$ is an amino acid selected from the group consisting of W or Y, $X_{18}$ is an amino acid selected from the group consisting of S or Q, $X_{22}$ is an amino acid selected from the group consisting of K or H, and $X_{27}$ is an amino acid selected from the group consisting of N or D. In another embodiment, each peptide in the population comprises a sequence of APL-ID7, C-G-K-I-L-N-L-V-S-$X_{10}$-$X_{11}$-N-E-K-K-P-P-E-A-P-A-A-D-E-A-A-G-P-A-T-H (SEQ ID NO: 8) or a fragment thereof, wherein $X_{10}$ is an amino acid selected from the group consisting of V, L or I, and $X_{11}$ is an amino acid selected from the group consisting of A or L. In still another embodiment, each peptide in the population comprises a sequence of APID 2-1, E-T-K-V-$X_5$-Y-$X_7$-Y-L-K-$X_{11}$-G-R-T-V-K-L-D-S-H-$X_{21}$-F-D-W-$X_{25}$-T-P-$X_{28}$-P-K-$X_{31}$-G-F-K-D-C (SEQ ID NO: 9) or a fragment thereof, wherein $X_5$ is an amino acid selected from the group consisting of V or A, $X_7$ is an amino acid selected from the group consisting of G, I or H, $X_{11}$ is an amino acid selected from the group consisting of E, N, or Q, $X_{21}$ is an amino acid selected from the group consisting of R, D, or N, $X_{25}$ is an amino acid selected from the group consisting of Q, D, or E, $X_{28}$ is an amino acid selected from the group consisting of E or N, and $X_{31}$ is an amino acid selected from the group consisting of L or V.

In certain embodiments, the populations of *Anaplasma* peptides may further comprise one or more antigenic peptides from another microbial species. In one embodiment, the population of *Anaplasma* peptides further comprises one or more antigenic peptides from an *Ehrlichia* species (e.g., *E. canis, E. chaffeensis, E. ewingii*, and *E. muris*), and/or a *Borrelia* species (e.g., *B. burgdorferi, B. afzelli*, or *B. garinii*).

Peptides of the invention may comprise at least 20, 30, 35, 40, 45, 50, or more amino acids. In some embodiments, peptides of the invention are isolated (e.g., synthetic and/or purified) peptides. In particular embodiments, peptides of the invention are conjugated to a ligand. For example, in certain embodiments, the peptides are biotinylated. In other embodiments, the peptides are conjugated to streptavidin, avidin, or neutravidin. In other embodiments, the peptides are conjugated to a carrier protein (e.g., serum albumin, keyhole limpet hemocyanin (KLH), or an immunoglobulin Fc domain). In still other embodiments, the peptides are conjugated to a dendrimer and/or are part of a multiple antigenic peptides system (MAPS). In certain embodiments, the peptides are conjugated to a detectable entity or label, such as an enzyme, a metallic nanomaterial, or a fluorophore. In certain embodiments, the peptides are conjugated to metallic nanoparticles, nanoshells, nanoplates, nanorings or nanorods.

In certain embodiments, peptides of the invention are attached to or immobilized on a solid support. In one embodiment, the peptides of the invention are attached to a solid support through a metallic nanolayer. In certain embodiments, the solid support is a bead or plurality of beads (e.g., a colloidal particle, metallic nanomaterial such as nanoparticle, nanoplate, or nanoshell, latex bead, etc.), a flow path in a lateral flow immunoassay device (e.g., a porous membrane), a blot (Western blot, a slot blot, or dot blot), a flow path in an analytical or centrifugal rotor, or a tube or well (e.g., in a plate suitable for an ELISA assay).

In one aspect, the present invention provides a composition comprising one or more populations of isolated peptides described herein.

In some embodiments, the composition comprises a population of isolated peptides, said population comprising three or more different peptides, wherein each peptide in the population comprises a sequence, or a fragment thereof, of SEQ ID NO: 1, 2, 3, 4, 5, 6, 7, 8, or 9.

In certain embodiments, the composition further comprises one or more antigenic peptides from an *Anaplasma* species, an *Ehrlichia* species, and/or a *Borrelia* species.

In some embodiments, the composition comprises at least two different populations of peptides described herein. In certain embodiments, at least one of the peptide populations is defined by SEQ ID NO: 3. For instance, in one embodiment, at least one of the peptide populations comprises three or more different peptides, wherein each peptide in the population comprises a sequence, or a fragment thereof, of SEQ ID NO: 3.

In certain embodiments, the composition further comprises a second population of isolated peptides. In some embodiments, the second peptide population is defined by SEQ ID NO: 7. In some other embodiments, each peptide in the second peptide population comprises the sequence, or a fragment thereof, of SEQ ID NO: 6.

In some embodiments, the composition further comprises a third population of isolated peptides that is different from the first and second peptide populations. In certain embodiments, each peptide in the third peptide population comprises the sequence, or a fragment thereof, of SEQ ID NO: 6.

In another aspect, the present invention also provides a method for detecting in a sample an antibody to an epitope of an *Anaplasma* antigen. In one embodiment, the method comprises contacting a sample with a peptide or population of peptides of the invention; and detecting formation of an antibody-peptide complex comprising the peptide or one or more peptides in the population, wherein formation of the complex is indicative of an antibody to an epitope of an *Anaplasma* antigen being present in the sample. The methods can be used to detect antibodies to antigens from *A. phagocytophilum, A. platys*, or *A. marginale* species.

In another embodiment, the present invention provides a method for diagnosing anaplasmosis or cyclic thrombocytopenia in a subject. In one embodiment, the method comprises contacting a sample from the subject with a peptide or population of peptides of the invention; and detecting formation of an antibody-peptide complex comprising the peptide or one or more peptides in the population, wherein formation of the complex is indicative of the subject having anaplasmosis or cyclic thrombocytopenia.

The present invention also includes a method for identifying the species of *Anaplasma* infecting a subject. In one embodiment, the method comprises contacting a sample from the subject with a first peptide or first population of peptides and a second peptide or second population of peptides, wherein the first peptide or first population of peptides specifically binds to antibodies against antigens from multiple *Anaplasma* species, and wherein the second peptide or second population of peptides specifically binds to antibodies against antigens from a single *Anaplasma* species; detecting formation of a first antibody-peptide complex comprising said first peptide or one or more peptides in the first population; and detecting formation of a second antibody-peptide complex comprising said second peptide or one or more peptides in the second population, wherein formation of both the first and second antibody-peptide complexes indicates that the subject is infected with the *Anaplasma* species that is specifically bound by the second population of isolated peptides.

In certain embodiments of the method, the first peptide or first population of peptides specifically binds to antibodies against antigens from *A. phagocytophilum*, *A. platys*, and *A. marginale*. In other embodiments, the first peptide or first population of peptides specifically binds to antibodies against antigens from *A. phagocytophilum* and *A. platys*. In some embodiments, the second peptide or second population of peptides specifically binds to antibodies against antigens from *A. platys*. In other embodiments, the second peptide or second population of peptides specifically binds to antibodies against antigens from *A. phagocytophilum*. In one embodiment of the method, the first peptide or first population of peptides is defined by SEQ ID NO: 3 and the second peptide or second population of peptides is defined by SEQ ID NO: 4, and the formation of both the first and second antibody-peptide complexes indicates that the subject is infected with *A. platys*. In another embodiment of the method, the first peptide or first population of peptides is defined by SEQ ID NO: 3 and the second peptide or second population of peptides is defined by SEQ ID NO: 4, and the formation of the first antibody-peptide complex, but not the second antibody-peptide complex indicates that the subject is infected with *A. phagocytophilum*.

In other embodiments, the method for identifying the species of *Anaplasma* infecting a subject comprises contacting a sample from the subject with a first population of peptides and a cell extract of a single *Anaplasma* species, wherein the first population of isolated peptides specifically binds to antibodies against antigens from multiple *Anaplasma* species; detecting formation of a first antibody-peptide complex comprising one or more peptides in the first population; and detecting formation of an antibody-cell extract complex comprising one or more components in the cell extract, wherein formation of both the first antibody-peptide complex and the antibody-cell extract complex indicates that the subject is infected with the *Anaplasma* species that produced the cell extract.

In any of the methods described above and herein, the peptide or population of peptides can, in some embodiments, be attached to or immobilized upon a solid support. In one such embodiment, the peptide or population of peptides is attached to the solid support through a metallic (e.g., gold) nanolayer. In certain embodiments, the solid support is a bead or plurality of beads (e.g., a colloidal particle, a metallic nanomaterial such as nanoparticle, nanoplate, nanoshell, nanorod, a latex bead, etc.), a flow path in a lateral flow immunoassay device (e.g., a porous membrane), a flow path in an analytical or centrifugal rotor, a blot (Western blot, a slot blot, or dot blot), or a tube or a well (e.g., in a plate suitable for an ELISA assay). In some embodiments, the solid support comprises metal, glass, a cellulose-based material (e.g., nitrocellulose), or a polymer (e.g., polystyrene, polyethylene, polypropylene, polyester, nylon, polysulfone, etc.). In other embodiments, the peptide or population of different peptides is attached to a dendrimer and/or incorporated into a multiple antigenic peptide system (MAPS) system. In certain other embodiments, the peptide or population of different peptides is attached to BSA, KLH, ovalbumin or a similar carrier.

In any of the methods described above and herein, the detecting step may comprise performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical or centrifugal rotor. In other embodiments, the detecting step comprises analyzing the sample using a Western blot, a slot blot, or a dot blot. In still other embodiments, the detecting step comprises analyzing the sample with an electrochemical sensor, an optical sensor, or an opto-electronic sensor. In certain embodiments, the detecting step comprises performing a wavelength shift assay. In certain embodiments, the detecting step comprises performing an Indirect Fluorescent Antibody test.

The sample from the subject used in any of the methods described above and herein, in some embodiments, is a bodily fluid, such as blood, serum, plasma, cerebrospinal fluid, urine, mucus, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

The present invention also includes kits comprising a peptide or population of peptides of the invention. In one embodiment, the kit comprises at least one population of peptides of the invention and a labeling reagent capable of binding to an antibody that recognizes an epitope of one or more peptides in the population. The labeling reagent may be an anti-human, anti-canine, or anti-feline IgG or IgM antibody conjugated to a detectable label. In other embodiments, the labeling reagent is protein A, protein G, and/or a protein A/G fusion protein conjugated to a detectable label. In related embodiments, the detectable label is an enzyme, a metallic nanomaterial, fluorophore, or colored latex particle. Examples of metallic nanomaterials include, but are not limited to, metallic nanoparticles, nanoshells, nanorings, nanorods, and nanoplates.

In certain embodiments, the peptides in the kit are attached to or immobilized on a solid support optionally through a metallic nanolayer. In certain embodiments, the solid support is a bead (e.g., a colloidal particle, a metallic nanomaterial such as nanoparticle, nanoplate, or nanoshell, a latex bead, etc.), a flow path in a lateral flow immunoassay device, a flow path in an analytical or centrifugal rotor, or a tube or a well (e.g., in a plate). In some embodiments, the peptide or peptides in the kit are attached to a dendrimer and/or incorporated into a MAPS system. In certain other embodiments, the peptide or mixture of different peptides is attached to BSA.

In some embodiments, the kits further comprise a population of beads or a plate (e.g., a plate suitable for an ELISA assay). In other embodiments, the kits further comprise a device, such as a lateral flow immunoassay device, an analytical or centrifugal rotor, a Western blot, a dot blot, a slot blot, an electrochemical sensor, an optical sensor, or an opto-electronic sensor. In certain embodiments, the population of beads, the plate, or the device is useful for performing an immunoassay. For example, in certain embodiments, the population of beads, the plate, or the device is useful for detecting formation of an antibody-peptide complex comprising an antibody from a sample and a peptide of the invention. In certain embodiments, a peptide or population of different peptides of the invention is attached to or immobilized on the beads, the plate, or the device.

The kits of the invention may further comprise a set of instructions indicating, for example, how to use a peptide or population of peptides of the invention to detect an antibody to an *Anaplasma* antigen or to diagnose anaplasmosis or cyclic thrombocytopenia in a subject. In certain embodiments, the kits comprise an instruction indicating how to use a population of beads, a plate, or a device (e.g., comprising a peptide or a population of different peptides of the invention) to detect an antibody to one or more *Anaplasma* antigens or to diagnose anaplasmosis or cyclic thrombocytopenia.

Additional aspects and embodiments of the invention will be apparent from the detailed description that follows.

DETAILED DESCRIPTION

Figure 1:
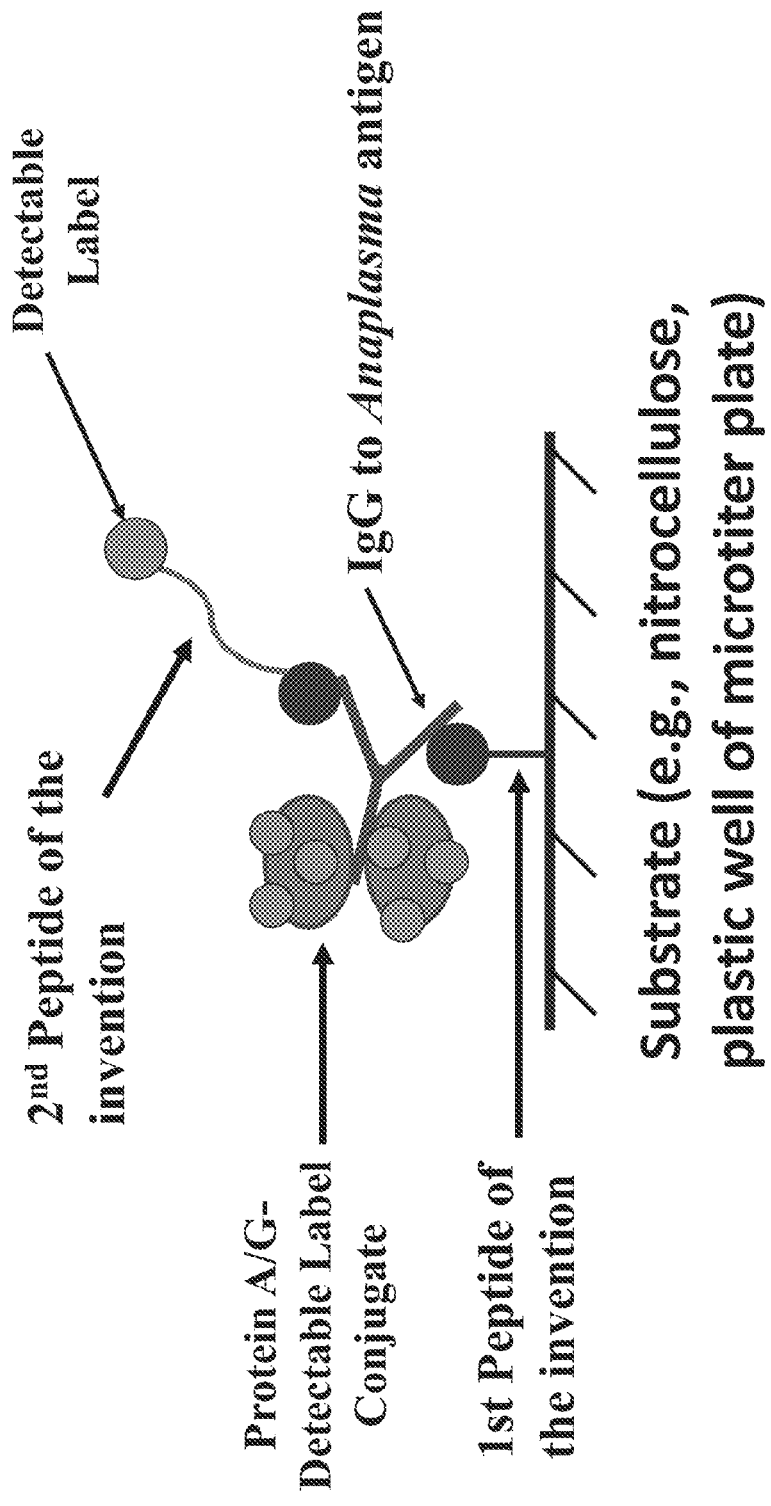
FIG. 1 is a diagram of a double antigen sandwich assay which can be used to detect antibodies to *Anaplasma* antigens. In this embodiment, peptides of the invention are immobilized to a suitable substrate (e.g., nitrocellulose membrane, well of an ELISA plate) at a test site. Antibodies to *Anaplasma* antigens in a test sample are bound by the immobilized peptides of the invention. Test sample antibodies to appropriate *Anaplasma* antigens will then bind to a second set of peptides of the invention that are conjugated to a detectable label (e.g., metallic nanomaterial such as nanoparticle, nanoplate, or nanoshell (e.g., colloidal gold), horse radish peroxidase (HRP), alkaline phosphatase (ALP), β-galactosidase (β-GAL), fluorophore, colored latex particle, quantum dot), which detects the presence of the antibodies bound to the first set of peptides immobilized at the test site. In certain embodiments, to amplify the detection signal, protein A and/or protein G molecules conjugated to a detectable label (e.g., metallic nanomaterial such as nanoparticle, nanoplate, or nanoshell (e.g., colloidal gold), HRP, ALP, β-GAL, fluorophore, colored latex particle, quantum dot) may be applied to the test site where they will bind to the Fc region of any antibodies to *Anaplasma* antigens captured by the immobilized peptides of the invention.

The present invention is based, in part, on the discovery that certain sequence variants of fragments of the *Anaplasma* outer membrane proteins provide for robust detection of an antibody response against *Anaplasma* species. Accordingly, the invention provides compositions, devices, methods, and kits useful for the detection of antibodies that bind to *Anaplasma* antigens and for the diagnosis of anaplasmosis.

The term "antigen," as used herein, refers to a molecule capable of being recognized by an antibody. An antigen can be, for example, a peptide or a modified form thereof. An antigen can comprise one or more epitopes.

The term "epitope," as used herein, is a portion of an antigen that is specifically recognized by an antibody. An epitope, for example, can comprise or consist of a portion of a peptide (e.g., a peptide of the invention). An epitope can be a linear epitope, sequential epitope, or a conformational epitope. In certain embodiments, epitopes may comprise non-contiguous regions.

The terms "nucleic acid," "oligonucleotide" and "polynucleotide" are used interchangeably herein and encompass DNA, RNA, cDNA, whether single stranded or double stranded, as well as chemical modifications thereof.

Single letter amino acid abbreviations used herein have their standard meaning in the art, and all peptide sequences described herein are written according to convention, with the N-terminal end to the left and the C-terminal end to the right.

Compositions and Devices

The present invention provides isolated peptides capable of binding to antibodies that recognize *Anaplasma* antigens and devices incorporating such peptides. In one embodiment, the present invention provides a population of isolated peptides comprising three or more different peptides, wherein each peptide in the population comprises a sequence of Abaxis ID 2 (SEQ ID NO: 1), Abaxis ID 3 (SEQ ID NO: 2), APL-ID1 (SEQ ID NO: 3), APL-ID2 (SEQ ID NO: 4), APL-ID3 (SEQ ID NO: 5), APL-ID5.1 (SEQ ID NO: 6), APL-ID6 (SEQ ID NO: 7), APL-ID7 (SEQ ID NO: 8), APID 2-1 (SEQ ID NO: 9), or fragments thereof. For instance, in one embodiment, the population of isolated peptides comprises three or more different peptides, wherein each peptide in the population comprises a sequence of E-T-R-V-A-Y-P-Y-$X_9$-K-D-G-R-T-V-K-$X_{17}$-D-S-H-$X_{21}$-F-D-W-Q-T-P-$X_{28}$-P-K-$X_{31}$-G-F-K-D-C (SEQ ID NO: 1), or a fragment thereof, wherein $X_9$ is an amino acid selected from the group consisting of I, P or H, $X_{17}$ is an amino acid selected from the group consisting of I, W, or Y, $X_{21}$ is an amino acid selected from the group consisting of R, D, or N, $X_{28}$ is an amino acid selected from the group consisting of E or N, and $X_{31}$ is an amino acid selected from the group consisting of L or V.

In some embodiments, peptides of the invention comprise a sequence of SEQ ID NO: 1, wherein $X_{28}$ is N and/or $X_{31}$ is V. In other embodiments, peptides of the invention comprise a sequence of SEQ ID NO: 1, wherein $X_9$ is P, $X_{17}$ is I, and/or $X_{21}$ is N. In certain embodiments, the population of isolated peptides comprises three or more peptides comprising or consisting of any one of the sequences in Table 1.

TABLE 1

Abaxis ID 2 Peptides

| Sequence | SEQ ID NO. |
|---|---|
| E-T-R-V-A-Y-P-Y-I-K-D-G-R-T-V-K-I-D-S-H-R-F-D-W-Q-T-P-E-P-K-L-G-F-K-D-C | 10 |
| E-T-R-V-A-Y-P-Y-P-K-D-G-R-T-V-K-I-D-S-H-R-F-D-W-Q-T-P-E-P-K-L-G-F-K-D-C | 11 |
| E-T-R-V-A-Y-P-Y-H-K-D-G-R-T-V-K-I-D-S-H-R-F-D-W-Q-T-P-E-P-K-L-G-F-K-D-C | 12 |
| E-T-R-V-A-Y-P-Y-I-K-D-G-R-T-V-K-W-D-S-H-R-F-D-W-Q-T-P-E-P-K-L-G-F-K-D-C | 13 |
| E-T-R-V-A-Y-P-Y-I-K-D-G-R-T-V-K-Y-D-S-H-R-F-D-W-Q-T-P-E-P-K-L-G-F-K-D-C | 14 |
| E-T-R-V-A-Y-P-Y-P-K-D-G-R-T-V-K-W-D-S-H-R-F-D-W-Q-T-P-E-P-K-L-G-F-K-D-C | 15 |
| E-T-R-V-A-Y-P-Y-P-K-D-G-R-T-V-K-Y-D-S-H-R-F-D-W-Q-T-P-E-P-K-L-G-F-K-D-C | 16 |
| E-T-R-V-A-Y-P-Y-H-K-D-G-R-T-V-K-W-D-S-H-R-F-D-W-Q-T-P-E-P-K-L-G-F-K-D-C | 17 |
| E-T-R-V-A-Y-P-Y-H-K-D-G-R-T-V-K-Y-D-S-H-R-F-D-W-Q-T-P-E-P-K-L-G-F-K-D-C | 18 |
| E-T-R-V-A-Y-P-Y-I-K-D-G-R-T-V-K-I-D-S-H-D-F-D-W-Q-T-P-E-P-K-L-G-F-K-D-C | 19 |
| E-T-R-V-A-Y-P-Y-I-K-D-G-R-T-V-K-W-D-S-H-D-F-D-W-Q-T-P-E-P-K-L-G-F-K-D-C | 20 |
| E-T-R-V-A-Y-P-Y-I-K-D-G-R-T-V-K-Y-D-S-H-D-F-D-W-Q-T-P-E-P-K-L-G-F-K-D-C | 21 |
| E-T-R-V-A-Y-P-Y-P-K-D-G-R-T-V-K-I-D-S-H-D-F-D-W-Q-T-P-E-P-K-L-G-F-K-D-C | 22 |
| E-T-R-V-A-Y-P-Y-P-K-D-G-R-T-V-K-W-D-S-H-D-F-D-W-Q-T-P-E-P-K-L-G-F-K-D-C | 23 |
| E-T-R-V-A-Y-P-Y-P-K-D-G-R-T-V-K-Y-D-S-H-D-F-D-W-Q-T-P-E-P-K-L-G-F-K-D-C | 24 |
| E-T-R-V-A-Y-P-Y-H-K-D-G-R-T-V-K-I-D-S-H-D-F-D-W-Q-T-P-E-P-K-L-G-F-K-D-C | 25 |
| E-T-R-V-A-Y-P-Y-H-K-D-G-R-T-V-K-W-D-S-H-D-F-D-W-Q-T-P-E-P-K-L-G-F-K-D-C | 26 |
| E-T-R-V-A-Y-P-Y-H-K-D-G-R-T-V-K-Y-D-S-H-D-F-D-W-a-T-P-E-P-K-L-G-F-K-D-C | 27 |
| E-T-R-V-A-Y-P-Y-I-K-D-G-R-T-V-K-I-D-S-H-N-F-D-W-Q-T-P-E-P-K-L-G-F-K-D-C | 28 |
| E-T-R-V-A-Y-P-Y-I-K-D-G-R-T-V-K-W-D-S-H-N-F-D-W-Q-T-P-E-P-K-L-G-F-K-D-C | 29 |
| E-T-R-V-A-Y-P-Y-I-K-D-G-R-T-V-K-Y-D-S-H-N-F-D-W-Q-T-P-E-P-K-L-G-F-K-D-C | 30 |
| E-T-R-V-A-Y-P-Y-P-K-D-G-R-T-V-K-I-D-S-H-N-F-D-W-Q-T-P-E-P-K-L-G-F-K-D-

TABLE 1-continued

Abaxis ID 2 Peptides

| Sequence | SEQ ID NO. |
|---|---|
| E-T-R-V-A-Y-P-Y-P-K-D-G-R-T-V-K-W-D-S-H-N-F-D-W-Q-T-P-E-P-K-L-G-F-K-D-C | 32 |
| E-T-R-V-A-Y-P-Y-P-K-D-G-R-T-V-K-Y-D-S-H-N-F-D-W-Q-T-P-E-P-K-L-G-F-K-D-C | 33 |
| E-T-R-V-A-Y-P-Y-H-K-D-G-R-T-V-K-I-D-S-H-N-F-D-W-Q-T-P-E-P-K-L-G-F-K-D-C | 34 |
| E-T-R-V-A-Y-P-Y-H-K-D-G-R-T-V-K-W-D-S-H-N-F-D-W-Q-T-P-E-P-K-L-G-F-K-D-C | 35 |
| E-T-R-V-A-Y-P-Y-H-K-D-G-R-T-V-K-Y-D-S-H-N-F-D-W-Q-T-P-E-P-K-L-G-F-K-D-C | 36 |
| E-T-R-V-A-Y-P-Y-I-K-D-G-R-T-V-K-I-D-S-H-R-F-D-W-Q-T-P-N-P-K-L-G-F-K-D-C | 37 |
| E-T-R-V-A-Y-P-Y-P-K-D-G-R-T-V-K-I-D-S-H-R-F-D-W-Q-T-P-N-P-K-L-G-F-K-D-C | 38 |
| E-T-R-V-A-Y-P-Y-H-K-D-G-R-T-V-K-I-D-S-H-R-F-D-W-Q-T-P-N-P-K-L-G-F-K-D-C | 39 |
| E-T-R-V-A-Y-P-Y-I-K-D-G-R-T-V-K-W-D-S-H-R-F-D-W-Q-T-P-N-P-K-L-G-F-K-D-C | 40 |
| E-T-R-V-A-Y-P-Y-I-K-D-G-R-T-V-K-Y-D-S-H-R-F-D-W-Q-T-P-N-P-K-L-G-F-K-D-C | 41 |
| E-T-R-V-A-Y-P-Y-P-K-D-G-R-T-V-K-W-D-S-H-R-F-D-W-Q-T-P-N-P-K-L-G-F-K-D-C | 42 |
| E-T-R-V-A-Y-P-Y-P-K-D-G-R-T-V-K-Y-D-S-H-R-F-D-W-Q-T-P-N-P-K-L-G-F-K-D-C | 43 |
| E-T-R-V-A-Y-P-Y-H-K-D-G-R-T-V-K-W-D-S-H-R-F-D-W-Q-T-P-N-P-K-L-G-F-K-D-C | 44 |
| E-T-R-V-A-Y-P-Y-H-K-D-G-R-T-V-K-Y-D-S-H-R-F-D-W-Q-T-P-N-P-K-L-G-F-K-D-C | 45 |
| E-T-R-V-A-Y-P-Y-I-K-D-G-R-T-V-K-I-D-S-H-D-F-D-W-Q-T-P-N-P-K-L-G-F-K-D-C | 46 |
| E-T-R-V-A-Y-P-Y-I-K-D-G-R-T-V-K-W-D-S-H-D-F-D-W-Q-T-P-N-P-K-L-G-F-K-D-C | 47 |
| E-T-R-V-A-Y-P-Y-I-K-D-G-R-T-V-K-Y-D-S-H-D-F-D-W-Q-T-P-N-P-K-L-G-F-K-D-C | 48 |
| E-T-R-V-A-Y-P-Y-P-K-D-G-R-T-V-K-I-D-S-H-D-F-D-W-Q-T-P-N-P-K-L-G-F-K-D-C | 49 |
| E-T-R-V-A-Y-P-Y-P-K-D-G-R-T-V-K-W-D-S-H-D-F-D-W-Q-T-P-N-P-K-L-G-F-K-D-C | 50 |
| E-T-R-V-A-Y-P-Y-P-K-D-G-R-T-V-K-Y-D-S-H-D-F-D-W-Q-T-P-N-P-K-L-G-F-K-D-C | 51 |
| E-T-R-V-A-Y-P-Y-H-K-D-G-R-T-V-K-I-D-S-H-D-F-D-W-Q-T-P-N-P-K-L-G-F-K-D-C | 52 |
| E-T-R-V-A-Y-P-Y-H-K-D-G-R-T-V-K-W-D-S-H-D-F-D-W-Q-T-P-N-P-K-L-G-F-K-D-C | 53 |
| E-T-R-V-A-Y-P-Y-H-K-D-G-R-T-V-K-Y-D-S-H-D-F-D-W-Q-T-P-N-P-K-L-G-F-K-D-C | 54 |
| E-T-R-V-A-Y-P-Y-I-K-D-G-R-T-V-K-I-D-S-H-N-F-D-W-Q-T-P-N-P-K-L-G-F-K-D-C | 55 |
| E-T-R-V-A-Y-P-Y-I-K-D-G-R-T-V-K-W-D-S-H-N-F-D-W-Q-T-P-N-P-K-L-G-F-K-D-C | 56 |
| E-T-R-V-A-Y-P-Y-I-K-D-G-R-T-V-K-Y-D-S-H-N-F-D-W-Q-T-P-N-P-K-L-G-F-K-D-C | 57 |
| E-T-R-V-A-Y-P-Y-P-K-D-G-R-T-V-K-I-D-S-H-N-F-D-W-Q-T-P-N-P-K-L-G-F-K-D-C | 58 |
| E-T-R-V-A-Y-P-Y-P-K-D-G-R-T-V-K-W-D-S-H-N-F-D-W-Q-T-P-N-P-K-L-G-F-K-D-C | 59 |
| E-T-R-V-A-Y-P-Y-P-K-D-G-R-T-V-K-Y-D-S-H-N-F-D-W-Q-T-P-N-P-K-L-G-F-K-D-C | 60 |
| E-T-R-V-A-Y-P-Y-H-K-D-G-R-T-V-K-I-D-S-H-N-F-D-W-Q-T-P-N-P-K-L-G-F-K-D-C | 61 |
| E-T-R-V-A-Y-P-Y-H-K-D-G-R-T-V-K-W-D-S-H-N-F-D-W-Q-T-P-N-P-K-L-G-F-K-D-C | 62 |
| E-T-R-V-A-Y-P-Y-H-K-D-G-R-T-V-K-Y-D-S-H-N-F-D-W-Q-T-P-N-P-K-L-G-F-K-D-C | 63 |
| E-T-R-V-A-Y-P-Y-I-K-D-G-R-T-V-K-I-D-S-H-R-F-D-W-Q-T-P-E-P-K-V-G-F-K-D-C | 64 |
| E-T-R-V-A-Y-P-Y-P-K-D-G-R-T-V-K-I-D-S-H-R-F-D-W-Q-T-P-E-P-K-V-G-F-K-D-C | 65 |
| E-T-R-V-A-Y-P-Y-H-K-D-G-R-T-V-K-I-D-S-H-R-F-D-W-Q-T-P-E-P-K-V-G-F-K-D-C | 66 |
| E-T-R-V-A-Y-P-Y-I-K-D-G-R-T-V-K-W-D-S-H-R-F-D-W-Q-T-P-E-P-K-V-G-F-K-D-C | 67 |
| E-T-R-V-A-Y-P-Y-I-K-D-G-R-T-V-K-Y-D-S-H-R-F-D-W-Q-T-P-E-P-K-V-G-F-K-D-C | 68 |
| E-T-R-V-A-Y-P-Y-P-K-D-G-R-T-V-K-W-D-S-H-R-F-D-W-Q-T-P-E-P-K-V-G-F-K-D-C | 69 |

TABLE 1-continued

Abaxis ID 2 Peptides

| Sequence | SEQ ID NO. |
|---|---|
| E-T-R-V-A-Y-P-Y-P-K-D-G-R-T-V-K-Y-D-S-H-R-F-D-W-Q-T-P-E-P-K-V-G-F-K-D-C | 70 |
| E-T-R-V-A-Y-P-Y-H-K-D-G-R-T-V-K-W-D-S-H-R-F-D-W-Q-T-P-E-P-K-V-G-F-K-D-C | 71 |
| E-T-R-V-A-Y-P-Y-H-K-D-G-R-T-V-K-Y-D-S-H-R-F-D-W-Q-T-P-E-P-K-V-G-F-K-D-C | 72 |
| E-T-R-V-A-Y-P-Y-I-K-D-G-R-T-V-K-I-D-S-H-D-F-D-W-Q-T-P-E-P-K-V-G-F-K-D-C | 73 |
| E-T-R-V-A-Y-P-Y-I-K-D-G-R-T-V-K-W-D-S-H-D-F-D-W-Q-T-P-E-P-K-V-G-F-K-D-C | 74 |
| E-T-R-V-A-Y-P-Y-I-K-D-G-R-T-V-K-Y-D-S-H-D-F-D-W-Q-T-P-E-P-K-V-G-F-K-D-C | 75 |
| E-T-R-V-A-Y-P-Y-P-K-D-G-R-T-V-K-I-D-S-H-D-F-D-W-Q-T-P-E-P-K-V-G-F-K-D-C | 76 |
| E-T-R-V-A-Y-P-Y-P-K-D-G-R-T-V-K-W-D-S-H-D-F-D-W-Q-T-P-E-P-K-V-G-F-K-D-C | 77 |
| E-T-R-V-A-Y-P-Y-P-K-D-G-R-T-V-K-Y-D-S-H-D-F-D-W-Q-T-P-E-P-K-V-G-F-K-D-C | 78 |
| E-T-R-V-A-Y-P-Y-H-K-D-G-R-T-V-K-I-D-S-H-D-F-D-W-Q-T-P-E-P-K-V-G-F-K-D-C | 79 |
| E-T-R-V-A-Y-P-Y-H-K-D-G-R-T-V-K-W-D-S-H-D-F-D-W-Q-T-P-E-P-K-V-G-F-K-D-C | 80 |
| E-T-R-V-A-Y-P-Y-H-K-D-G-R-T-V-K-Y-D-S-H-D-F-D-W-Q-T-P-E-P-K-V-G-F-K-D-C | 81 |
| E-T-R-V-A-Y-P-Y-I-K-D-G-R-T-V-K-I-D-S-H-N-F-D-W-Q-T-P-E-P-K-V-G-F-K-D-C | 82 |
| E-T-R-V-A-Y-P-Y-I-K-D-G-R-T-V-K-W-D-S-H-N-F-D-W-Q-T-P-E-P-K-V-G-F-K-D-C | 83 |
| E-T-R-V-A-Y-P-Y-I-K-D-G-R-T-V-K-Y-D-S-H-N-F-D-W-Q-T-P-E-P-K-V-G-F-K-D-C | 84 |
| E-T-R-V-A-Y-P-Y-P-K-D-G-R-T-V-K-I-D-S-H-N-F-D-W-Q-T-P-E-P-K-V-G-F-K-D-C | 85 |
| E-T-R-V-A-Y-P-Y-P-K-D-G-R-T-V-K-W-D-S-H-N-F-D-W-Q-T-P-E-P-K-V-G-F-K-D-C | 86 |
| E-T-R-V-A-Y-P-Y-P-K-D-G-R-T-V-K-Y-D-S-H-N-F-D-W-Q-T-P-E-P-K-V-G-F-K-D-C | 87 |
| E-T-R-V-A-Y-P-Y-H-K-D-G-R-T-V-K-I-D-S-H-N-F-D-W-Q-T-P-E-P-K-V-G-F-K-D-C | 88 |
| E-T-R-V-A-Y-P-Y-H-K-D-G-R-T-V-K-W-D-S-H-N-F-D-W-Q-T-P-E-P-K-V-G-F-K-D-C | 89 |
| E-T-R-V-A-Y-P-Y-H-K-D-G-R-T-V-K-Y-D-S-H-N-F-D-W-Q-T-P-E-P-K-V-G-F-K-D-C | 90 |
| E-T-R-V-A-Y-P-Y-I-K-D-G-R-T-V-K-I-D-S-H-R-F-D-W-Q-T-P-N-P-K-L-G-F-K-D-C | 91 |
| E-T-R-V-A-Y-P-Y-P-K-D-G-R-T-V-K-I-D-S-H-R-F-D-W-Q-T-P-N-P-K-L-G-F-K-D-C | 92 |
| E-T-R-V-A-Y-P-Y-H-K-D-G-R-T-V-K-I-D-S-H-R-F-D-W-Q-T-P-N-P-K-L-G-F-K-D-C | 93 |
| E-T-R-V-A-Y-P-Y-I-K-D-G-R-T-V-K-W-D-S-H-R-F-D-W-Q-T-P-N-P-K-L-G-F-K-D-C | 94 |
| E-T-R-V-A-Y-P-Y-I-K-D-G-R-T-V-K-Y-D-S-H-R-F-D-W-Q-T-P-N-P-K-L-G-F-K-D-C | 95 |
| E-T-R-V-A-Y-P-Y-P-K-D-G-R-T-V-K-W-D-S-H-R-F-D-W-Q-T-P-N-P-K-L-G-F-K-D-C | 96 |
| E-T-R-V-A-Y-P-Y-P-K-D-G-R-T-V-K-Y-D-S-H-R-F-D-W-Q-T-P-N-P-K-L-G-F-K-D-C | 97 |
| E-T-R-V-A-Y-P-Y-H-K-D-G-R-T-V-K-W-D-S-H-R-F-D-W-Q-T-P-N-P-K-L-G-F-K-D-C | 98 |
| E-T-R-V-A-Y-P-Y-H-K-D-G-R-T-V-K-Y-D-S-H-R-F-D-W-Q-T-P-N-P-K-L-G-F-K-D-C | 99 |
| E-T-R-V-A-Y-P-Y-I-K-D-G-R-T-V-K-I-D-S-H-D-F-D-W-Q-T-P-N-P-K-L-G-F-K-D-C | 100 |
| E-T-R-V-A-Y-P-Y-I-K-D-G-R-T-V-K-W-D-S-H-D-F-D-W-Q-T-P-N-P-K-L-G-F-K-D-C | 101 |
| E-T-R-V-A-Y-P-Y-I-K-D-G-R-T-V-K-Y-D-S-H-D-F-D-W-Q-T-P-N-P-K-L-G-F-K-D-C | 102 |
| E-T-R-V-A-Y-P-Y-P-K-D-G-R-T-V-K-I-D-S-H-D-F-D-W-Q-T-P-N-P-K-L-G-F-K-D-C | 103 |
| E-T-R-V-A-Y-P-Y-P-K-D-G-R-T-V-K-W-D-S-H-D-F-D-W-Q-T-P-N-P-K-L-G-F-K-D-C | 104 |
| E-T-R-V-A-Y-P-Y-P-K-D-G-R-T-V-K-Y-D-S-H-D-F-D-W-Q-T-P-N-P-K-L-G-F-K-D-C | 105 |
| E-T-R-V-A-Y-P-Y-H-K-D-G-R-T-V-K-I-D-S-H-D-F-D-W-Q-T-P-N-P-K-L-G-F-K-D-C | 106 |

TABLE 1-continued

Abaxis ID 2 Peptides

| Sequence | SEQ ID NO. |
|---|---|
| E-T-R-V-A-Y-P-Y-H-K-D-G-R-T-V-K-W-D-S-H-D-F-D-W-Q-T-P-N-P-K-L-G-F-K-D-C | 107 |
| E-T-R-V-A-Y-P-Y-H-K-D-G-R-T-V-K-Y-D-S-H-D-F-D-W-Q-T-P-N-P-K-L-G-F-K-D-C | 108 |
| E-T-R-V-A-Y-P-Y-I-K-D-G-R-T-V-K-I-D-S-H-N-F-D-W-Q-T-P-N-P-K-L-G-F-K-D-C | 109 |
| E-T-R-V-A-Y-P-Y-I-K-D-G-R-T-V-K-W-D-S-H-N-F-D-W-Q-T-P-N-P-K-L-G-F-K-D-C | 110 |
| E-T-R-V-A-Y-P-Y-I-K-D-G-R-T-V-K-Y-D-S-H-N-F-D-W-Q-T-P-N-P-K-L-G-F-K-D-C | 111 |
| E-T-R-V-A-Y-P-Y-P-K-D-G-R-T-V-K-I-D-S-H-N-F-D-W-Q-T-P-N-P-K-L-G-F-K-D-C | 112 |
| E-T-R-V-A-Y-P-Y-P-K-D-G-R-T-V-K-W-D-S-H-N-F-D-W-Q-T-P-N-P-K-L-G-F-K-D-C | 113 |
| E-T-R-V-A-Y-P-Y-P-K-D-G-R-T-V-K-Y-D-S-H-N-F-D-W-Q-T-P-N-P-K-L-G-F-K-D-C | 114 |
| E-T-R-V-A-Y-P-Y-H-K-D-G-R-T-V-K-I-D-S-H-N-F-D-W-Q-T-P-N-P-K-L-G-F-K-D-C | 115 |
| E-T-R-V-A-Y-P-Y-H-K-D-G-R-T-V-K-W-D-S-H-N-F-D-W-Q-T-P-N-P-K-L-G-F-K-D-C | 116 |
| E-T-R-V-A-Y-P-Y-H-K-D-G-R-T-V-K-Y-D-S-H-N-F-D-W-Q-T-P-N-P-K-L-G-F-K-D-C | 117 |

In another embodiment, the population of isolated peptides comprises three or more different peptides, wherein each peptide in the population comprises a sequence of I-E-$X_3$-G-Y-E-$X_7$-F-K-T-$X_{11}$-G-I-R-$X_{15}$-S-G-T-K-E-C (SEQ ID NO: 2), or a fragment thereof, wherein $X_3$ is an amino acid selected from the group consisting of L, V or A, $X_7$ is an amino acid selected from the group consisting of K, N or Q, $X_{11}$ is an amino acid selected from the group consisting of R, D, or N, and $X_{15}$ is an amino acid selected from the group consisting of E, N or Q. In some embodiments, peptides of the invention comprise a sequence of SEQ ID NO: 2, wherein $X_3$ is A, and/or $X_7$ is N. In other embodiments, peptides of the invention comprise a sequence of SEQ ID NO: 2, wherein $X_{11}$ is R, and/or $X_{15}$ is Q. In particular embodiments, the population of isolated peptides comprises three or more peptides comprising or consisting of any one of the sequences in Table 2.

TABLE 2

Abaxis ID 3 Peptides

| Sequence | SEQ ID NO. |
|---|---|
| I-E-I-G-Y-E-K-F-K-T-R-G-I-R-E-S-G-T-K-E-C | 118 |
| I-E-I-G-Y-E-N-F-K-T-R-G-I-R-E-S-G-T-K-E-C | 119 |
| I-E-I-G-Y-E-Q-F-K-T-R-G-I-R-E-S-G-T-K-E-C | 120 |
| I-E-V-G-Y-E-K-F-K-T-R-G-I-R-E-S-G-T-K-E-C | 121 |
| I-E-A-G-Y-E-K-F-K-T-R-G-I-R-E-S-G-T-K-E-C | 122 |
| I-E-V-G-Y-E-N-F-K-T-R-G-I-R-E-S-G-T-K-E-C | 123 |
| I-E-V-G-Y-E-Q-F-K-T-R-G-I-R-E-S-G-T-K-E-C | 124 |
| I-E-A-G-Y-E-N-F-K-T-R-G-I-R-E-S-G-T-K-E-C | 125 |
| I-E-A-G-Y-E-Q-F-K-T-R-G-I-R-E-S-G-T-K-E-C | 126 |
| I-E-I-G-Y-E-K-F-K-T-D-G-I-R-E-S-G-T-K-E-C | 127 |
| I-E-I-G-Y-E-N-F-K-T-D-G-I-R-E-S-G-T-K-E-C | 128 |
| I-E-I-G-Y-E-Q-F-K-T-D-G-I-R-E-S-G-T-K-E-C | 129 |

TABLE 2-continued

Abaxis ID 3 Peptides

| Sequence | SEQ ID NO. |
|---|---|
| I-E-V-G-Y-E-K-F-K-T-D-G-I-R-E-S-G-T-K-E-C | 130 |
| I-E-A-G-Y-E-K-F-K-T-D-G-I-R-E-S-G-T-K-E-C | 131 |
| I-E-V-G-Y-E-N-F-K-T-D-G-I-R-E-S-G-T-K-E-C | 132 |
| I-E-V-G-Y-E-Q-F-K-T-D-G-I-R-E-S-G-T-K-E-C | 133 |
| I-E-A-G-Y-E-N-F-K-T-D-G-I-R-E-S-G-T-K-E-C | 134 |
| I-E-A-G-Y-E-Q-F-K-T-D-G-I-R-E-S-G-T-K-E-C | 135 |
| I-E-I-G-Y-E-K-F-K-T-N-G-I-R-E-S-G-T-K-E-C | 136 |
| I-E-I-G-Y-E-N-F-K-T-N-G-I-R-E-S-G-T-K-E-C | 137 |
| I-E-I-G-Y-E-Q-F-K-T-N-G-I-R-E-S-G-T-K-E-C | 138 |
| I-E-V-G-Y-E-K-F-K-T-N-G-I-R-E-S-G-T-K-E-C | 139 |
| I-E-A-G-Y-E-K-F-K-T-N-G-I-R-E-S-G-T-K-E-C | 140 |
| I-E-V-G-Y-E-N-F-K-T-N-G-I-R-E-S-G-T-K-E-C | 141 |
| I-E-V-G-Y-E-Q-F-K-T-N-G-I-R-E-S-G-T-K-E-C | 142 |
| I-E-A-G-Y-E-N-F-K-T-N-G-I-R-E-S-G-T-K-E-C | 143 |
| I-E-A-G-Y-E-Q-F-K-T-N-G-I-R-E-S-G-T-K-E-C | 144 |
| I-E-I-G-Y-E-K-F-K-T-R-G-I-R-N-S-G-T-K-E-C | 145 |
| I-E-I-G-Y-E-N-F-K-T-R-G-I-R-N-S-G-T-K-E-C | 146 |
| I-E-I-G-Y-E-Q-F-K-T-R-G-I-R-N-S-G-T-K-E-C | 147 |
| I-E-V-G-Y-E-K-F-K-T-R-G-I-R-N-S-G-T-K-E-C | 148 |
| I-E-A-G-Y-E-K-F-K-T-R-G-I-R-N-S-G-T-K-E-C | 149 |
| I-E-V-G-Y-E-N-F-K-T-R-G-I-R-N-S-G-T-K-E-C | 150 |
| I-E-V-G-Y-E-Q-F-K-T-R-G-I-R-N-S-G-T-K-E-C | 151 |

TABLE 2-continued

Abaxis ID 3 Peptides

| Sequence | SEQ ID NO. |
|---|---|
| I-E-A-G-Y-E-N-F-K-T-R-G-I-R-N-S-G-T-K-E-C | 152 |
| I-E-A-G-Y-E-Q-F-K-T-R-G-I-R-N-S-G-T-K-E-C | 153 |
| I-E-I-G-Y-E-K-F-K-T-D-G-I-R-N-S-G-T-K-E-C | 154 |
| I-E-I-G-Y-E-N-F-K-T-D-G-I-R-N-S-G-T-K-E-C | 155 |
| I-E-I-G-Y-E-Q-F-K-T-D-G-I-R-N-S-G-T-K-E-C | 156 |
| I-E-V-G-Y-E-K-F-K-T-D-G-I-R-N-S-G-T-K-E-C | 157 |
| I-E-A-G-Y-E-K-F-K-T-D-G-I-R-N-S-G-T-K-E-C | 158 |
| I-E-V-G-Y-E-N-F-K-T-D-G-I-R-N-S-G-T-K-E-C | 159 |
| I-E-V-G-Y-E-Q-F-K-T-D-G-I-R-N-S-G-T-K-E-C | 160 |
| I-E-A-G-Y-E-N-F-K-T-D-G-I-R-N-S-G-T-K-E-C | 161 |
| I-E-A-G-Y-E-Q-F-K-T-D-G-I-R-N-S-G-T-K-E-C | 162 |
| I-E-I-G-Y-E-K-F-K-T-N-G-I-R-N-S-G-T-K-E-C | 163 |
| I-E-I-G-Y-E-N-F-K-T-N-G-I-R-N-S-G-T-K-E-C | 164 |
| I-E-I-G-Y-E-Q-F-K-T-N-G-I-R-N-S-G-T-K-E-C | 165 |
| I-E-V-G-Y-E-K-F-K-T-N-G-I-R-N-S-G-T-K-E-C | 166 |
| I-E-A-G-Y-E-K-F-K-T-N-G-I-R-N-S-G-T-K-E-C | 167 |
| I-E-V-G-Y-E-N-F-K-T-N-G-I-R-N-S-G-T-K-E-C | 168 |
| I-E-V-G-Y-E-Q-F-K-T-N-G-I-R-N-S-G-T-K-E-C | 169 |
| I-E-A-G-Y-E-N-F-K-T-N-G-I-R-N-S-G-T-K-E-C | 170 |
| I-E-A-G-Y-E-Q-F-K-T-N-G-I-R-N-S-G-T-K-E-C | 171 |
| I-E-I-G-Y-E-K-F-K-T-R-G-I-R-Q-S-G-T-K-E-C | 172 |
| I-E-I-G-Y-E-N-F-K-T-R-G-I-R-Q-S-G-T-K-E-C | 173 |
| I-E-I-G-Y-E-Q-F-K-T-R-G-I-R-Q-S-G-T-K-E-C | 174 |
| I-E-V-G-Y-E-K-F-K-T-R-G-I-R-Q-S-G-T-K-E-C | 175 |
| I-E-A-G-Y-E-K-F-K-T-R-G-I-R-Q-S-G-T-K-E-C | 176 |
| I-E-V-G-Y-E-N-F-K-T-R-G-I-R-Q-S-G-T-K-E-C | 177 |
| I-E-V-G-Y-E-Q-F-K-T-R-G-I-R-Q-S-G-T-K-E-C | 178 |
| I-E-A-G-Y-E-N-F-K-T-R-G-I-R-Q-S-G-T-K-E-C | 179 |
| I-E-A-G-Y-E-Q-F-K-T-R-G-I-R-Q-S-G-T-K-E-C | 180 |
| I-E-I-G-Y-E-K-F-K-T-D-G-I-R-Q-S-G-T-K-E-C | 181 |
| I-E-I-G-Y-E-N-F-K-T-D-G-I-R-Q-S-G-T-K-E-C | 182 |
| I-E-I-G-Y-E-Q-F-K-T-D-G-I-R-Q-S-G-T-K-E-C | 183 |
| I-E-V-G-Y-E-K-F-K-T-D-G-I-R-Q-S-G-T-K-E-C | 184 |
| I-E-A-G-Y-E-K-F-K-T-D-G-I-R-Q-S-G-T-K-E-C | 185 |
| I-E-V-G-Y-E-N-F-K-T-D-G-I-R-Q-S-G-T-K-E-C | 186 |
| I-E-V-G-Y-E-Q-F-K-T-D-G-I-R-Q-S-G-T-K-E-C | 187 |
| I-E-A-G-Y-E-N-F-K-T-D-G-I-R-Q-S-G-T-K-E-C | 188 |
| I-E-A-G-Y-E-Q-F-K-T-D-G-I-R-Q-S-G-T-K-E-C | 189 |
| I-E-I-G-Y-E-K-F-K-T-N-G-I-R-Q-S-G-T-K-E-C | 190 |
| I-E-I-G-Y-E-N-F-K-T-N-G-I-R-Q-S-G-T-K-E-C | 191 |
| I-E-I-G-Y-E-Q-F-K-T-N-G-I-R-Q-S-G-T-K-E-C | 102 |
| I-E-V-G-Y-E-K-F-K-T-N-G-I-R-Q-S-G-T-K-E-C | 193 |
| I-E-A-G-Y-E-K-F-K-T-N-G-I-R-Q-S-G-T-K-E-C | 194 |
| I-E-V-G-Y-E-N-F-K-T-N-G-I-R-Q-S-G-T-K-E-C | 195 |
| I-E-V-G-Y-E-Q-F-K-T-N-G-I-R-Q-S-G-T-K-E-C | 196 |
| I-E-A-G-Y-E-N-F-K-T-N-G-I-R-Q-S-G-T-K-E-C | 197 |
| I-E-A-G-Y-E-Q-F-K-T-N-G-I-R-Q-S-G-T-K-E-C | 198 |

In certain embodiments, the population of isolated peptides comprises three or more different peptides, wherein each peptide in the population comprises a sequence of E-T-K-V-$X_5$-Y-$X_7$-Y-L-K-$X_{11}$-G-R-T-V-K-L-$X_{18}$-S-H-$X_{21}$-F-D-W-$X_{25}$-T-P-$X_{28}$-P-K-$X_{31}$-G-F-K-D-G-G-G-G-G-K-D-G-T-$X_{45}$-V-E-$X_{48}$-K-A-$X_{51}$-K-F-$X_{54}$-W-N-$X_{57}$-P-D-$X_{60}$-R-I-$X_{63}$-F-K-$X_{66}$-C (SEQ ID NO: 3), or a fragment thereof, wherein $X_5$ is an amino acid selected from the group consisting of V or A, $X_7$ is an amino acid selected from the group consisting of G, I or H, $X_{11}$ is an amino acid selected from the group consisting of E, N, or Q, $X_{18}$ is an amino acid selected from the group consisting of D or N, $X_{21}$ is an amino acid selected from the group consisting of R, D, or N, $X_{25}$ is an amino acid selected from the group consisting of Q, D, or E, $X_{28}$ is an amino acid selected from the group consisting of E or N, $X_{31}$ is an amino acid selected from the group consisting of L or V, $X_{45}$ is an amino acid selected from the group consisting of K or Q, $X_{48}$ is an amino acid selected from the group consisting of F or V, $X_{51}$ is an amino acid selected from the group consisting of D or N, $X_{54}$ is an amino acid selected from the group consisting of E or Q, $X_{57}$ is an amino acid selected from the group consisting of S or Q, $X_{60}$ is an amino acid selected from the group consisting of F or W, $X_{63}$ is an amino acid selected from the group consisting of I or V, and $X_{66}$ is an amino acid selected from the group consisting of Q or D.

In related embodiments, peptides of the invention comprise a sequence of SEQ ID NO: 3, wherein $X_5$ is A, $X_{18}$ is D, and/or $X_{31}$ is V. In other embodiments, peptides of the invention comprise a sequence of SEQ ID NO: 3, wherein $X_{45}$ is Q, $X_{48}$ is F, and/or $X_{51}$ is N. In still other embodiments, peptides of the invention comprise a sequence of SEQ ID NO: 3, wherein $X_{54}$ is E, $X_{57}$ is S, and/or $X_{60}$ is W. In some embodiments, peptides of the invention comprise a sequence of SEQ ID NO: 3, wherein $X_{63}$ is I and/or $X_{66}$ is D. In particular embodiments, the population of isolated peptides comprises three or more peptides comprising or consisting of any one of the sequences in Table 3.

TABLE 3

| APL-ID1 Peptides | |
|---|---|
| Sequence | SEQ ID NO. |
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 199 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 200 |
| E-T-K-V-V-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 201 |
| E-T-K-V-A-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 202 |
| E-T-K-V-A-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 203 |
| E-T-K-V-A-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 204 |
| E-T-K-V-V-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 205 |
| E-T-K-V-V-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 206 |
| E-T-K-V-V-Y-H-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 207 |
| E-T-K-V-A-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 208 |
| E-T-K-V-A-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 209 |
| E-T-K-V-A-Y-H-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 210 |
| E-T-K-V-V-Y-G-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 211 |
| E-T-K-V-V-Y-I-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 212 |
| E-T-K-V-V-Y-H-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 213 |
| E-T-K-V-A-Y-G-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 214 |
| E-T-K-V-A-Y-I-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 215 |
| E-T-K-V-A-Y-H-Y-L-K-Q-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 216 |
| E-T-K-V-V-Y-G-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 217 |
| E-T-K-V-V-Y-I-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 218 |
| E-T-K-V-V-Y-H-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 219 |
| E-T-K-V-A-Y-G-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 220 |
| E-T-K-V-A-Y-I-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 221 |
| E-T-K-V-A-Y-H-Y-L-K-E-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 222 |
| E-T-K-V-V-Y-G-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 223 |

TABLE 3-continued

APL-ID1 Peptides

| Sequence | SEQ ID NO. |
|---|---|
| E-T-K-V-V-Y-I-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 224 |
| E-T-K-V-V-Y-H-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 225 |
| E-T-K-V-A-Y-G-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 226 |
| E-T-K-V-A-Y-I-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 227 |
| E-T-K-V-A-Y-H-Y-L-K-N-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 228 |
| E-T-K-V-V-Y-G-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 229 |
| E-T-K-V-V-Y-I-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 230 |
| E-T-K-V-V-Y-H-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 231 |
| E-T-K-V-A-Y-G-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 232 |
| E-T-K-V-A-Y-I-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 233 |
| E-T-K-V-A-Y-H-Y-L-K-Q-G-R-T-V-K-L-N-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 234 |
| E-T-K-V-V-Y-G-Y-L-K-E-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 235 |
| E-T-K-V-V-Y-I-Y-L-K-E-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 236 |
| E-T-K-V-V-Y-H-Y-L-K-E-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 237 |
| E-T-K-V-A-Y-G-Y-L-K-E-G-R-T-V-K-L-D-S-H-D-F-D-W-a-T-P-E-P-K-L-G-F-K-D-G-G-G-G-G-K-D-G-T-K-V-E-F-K-A-D-K-F-E-W-N-S-P-D-F-R-I-I-F-K-Q-C | 238 |
| E-T-K-V-A-Y-I-Y-L-K-E-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 239 |
| E-T-K-V-A-Y-H-Y-L-K-E-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 240 |
| E-T-K-V-V-Y-G-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 241 |
| E-T-K-V-V-Y-I-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 242 |
| E-T-K-V-V-Y-H-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 243 |
| E-T-K-V-A-Y-G-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 244 |
| E-T-K-V-A-Y-I-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 245 |
| E-T-K-V-A-Y-H-Y-L-K-N-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 246 |
| E-T-K-V-V-Y-G-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 247 |
| E-T-K-V-V-Y-I-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 248 |

TABLE 3-continued

APL-ID1 Peptides

| Sequence | SEQ ID NO. |
|---|---|
| E-T-K-V-V-Y-H-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 249 |
| E-T-K-V-A-Y-G-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 250 |
| E-T-K-V-A-Y-I-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 251 |
| E-T-K-V-A-Y-H-Y-L-K-Q-G-R-T-V-K-L-D-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 252 |
| E-T-K-V-V-Y-G-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 253 |
| E-T-K-V-V-Y-I-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 254 |
| E-T-K-V-V-Y-H-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 255 |
| E-T-K-V-A-Y-G-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 256 |
| E-T-K-V-A-Y-I-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 257 |
| E-T-K-V-A-Y-H-Y-L-K-E-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 258 |
| E-T-K-V-V-Y-G-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 259 |
| E-T-K-V-V-Y-I-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 260 |
| E-T-K-V-V-Y-H-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 261 |
| E-T-K-V-A-Y-G-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 262 |
| E-T-K-V-A-Y-I-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 263 |
| E-T-K-V-A-Y-H-Y-L-K-N-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 264 |
| E-T-K-V-V-Y-G-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 265 |
| E-T-K-V-V-Y-I-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 266 |
| E-T-K-V-V-Y-H-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 267 |
| E-T-K-V-A-Y-G-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 268 |
| E-T-K-V-A-Y-I-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 269 |
| E-T-K-V-A-Y-H-Y-L-K-Q-G-R-T-V-K-L-N-S-H-D-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 270 |
| E-T-K-V-V-Y-G-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 271 |
| E-T-K-V-V-Y-I-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 272 |
| E-T-K-V-V-Y-H-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 273 |

TABLE 3-continued

APL-ID1 Peptides

| Sequence | SEQ ID NO. |
|---|---|
| E-T-K-V-A-Y-G-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 274 |
| E-T-K-V-A-Y-I-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 275 |
| E-T-K-V-A-Y-H-Y-L-K-E-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 276 |
| E-T-K-V-V-Y-G-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 277 |
| E-T-K-V-V-Y-I-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 278 |
| E-T-K-V-V-Y-H-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 279 |
| E-T-K-V-A-Y-G-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 280 |
| E-T-K-V-A-Y-I-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 281 |
| E-T-K-V-A-Y-H-Y-L-K-N-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 282 |
| E-T-K-V-V-Y-G-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 283 |
| E-T-K-V-V-Y-I-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 284 |
| E-T-K-V-V-Y-H-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 285 |
| E-T-K-V-A-Y-G-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 286 |
| E-T-K-V-A-Y-I-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 287 |
| E-T-K-V-A-Y-H-Y-L-K-Q-G-R-T-V-K-L-D-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 288 |
| E-T-K-V-V-Y-G-Y-L-K-E-G-R-T-V-K-L-N-S-H-N-F-D-W-Q-T-P-E-P-K-I-G-F-K-D-G-G-G-G-G-K-D-G-T-K-V-E-F-K-A-D-K-F-E-W-N-S-P-D-F-R-I-I-F-K-Q-C | 289 |
| E-T-K-V-V-Y-I-Y-L-K-E-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 290 |
| E-T-K-V-V-Y-H-Y-L-K-E-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 291 |
| E-T-K-V-A-Y-G-Y-L-K-E-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 292 |
| E-T-K-V-A-Y-I-Y-L-K-E-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 293 |
| E-T-K-V-A-Y-H-Y-L-K-E-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 294 |
| E-T-K-V-V-Y-G-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 295 |
| E-T-K-V-V-Y-I-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 296 |
| E-T-K-V-V-Y-H-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 297 |
| E-T-K-V-A-Y-G-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 298 |

TABLE 3-continued

APL-ID1 Peptides

| Sequence | SEQ ID NO. |
|---|---|
| E-T-K-V-A-Y-I-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 299 |
| E-T-K-V-A-Y-H-Y-L-K-N-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 300 |
| E-T-K-V-V-Y-G-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 301 |
| E-T-K-V-V-Y-I-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 302 |
| E-T-K-V-V-Y-H-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 303 |
| E-T-K-V-A-Y-G-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 304 |
| E-T-K-V-A-Y-I-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 305 |
| E-T-K-V-A-Y-H-Y-L-K-Q-G-R-T-V-K-L-N-S-H-N-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-Q-C | 306 |
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 307 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 308 |
| E-T-K-V-V-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 309 |
| E-T-K-V-A-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 310 |
| E-T-K-V-A-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 311 |
| E-T-K-V-A-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 312 |
| E-T-K-V-V-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 313 |
| E-T-K-V-V-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 314 |
| E-T-K-V-V-Y-H-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 315 |
| E-T-K-V-A-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-I-F-K-D-C | 316 |
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 317 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 318 |
| E-T-K-V-V-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 319 |
| E-T-K-V-A-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 320 |
| E-T-K-V-A-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 321 |
| E-T-K-V-A-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 322 |
| E-T-K-V-V-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 323 |

TABLE 3-continued

APL-ID1 Peptides

| Sequence | SEQ ID NO. |
|---|---|
| E-T-K-V-V-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 324 |
| E-T-K-V-V-Y-H-Y-L-K-N-G-R-T-V-K-L-D-S-H-R-F-D-W-a-T-P-E-P-K-L-G-F-K-D-G-G-G-G-G-K-D-G-T-K-V-E-F-K-A-D-K-F-E-W-N-S-P-D-F-R-I-V-F-K-D-C | 325 |
| E-T-K-V-A-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-F-R-I-V-F-K-D-C | 326 |
| E-T-K-V-V-Y-G-Y-L-K-E-G-R-T-V-K-L-D-S-H-R-F-D-W-a-T-P-E-P-K-L-G-F-K-D-G-G-G-G-G-K-D-G-T-K-V-E-F-K-A-D-K-F-E-W-N-S-P-D-W-R-I-V-F-K-D-C | 327 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 328 |
| E-T-K-V-V-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 329 |
| E-T-K-V-A-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 330 |
| E-T-K-V-A-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 331 |
| E-T-K-V-A-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 332 |
| E-T-K-V-V-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 333 |
| E-T-K-V-V-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 334 |
| E-T-K-V-V-Y-H-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 335 |
| E-T-K-V-A-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-S-P-D-W-R-I-V-F-K-D-C | 336 |
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 337 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 338 |
| E-T-K-V-V-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 339 |
| E-T-K-V-A-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 340 |
| E-T-K-V-A-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 341 |
| E-T-K-V-A-Y-H-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 342 |
| E-T-K-V-V-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 343 |
| E-T-K-V-V-Y-I-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 344 |
| E-T-K-V-V-Y-H-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 345 |
| E-T-K-V-A-Y-G-Y-L-K-N-G-R-T-V-K-L-D-S-H-R-F-D-W-Q-T-P-E-P-K-L-G-F-K-D-G-G-G-G-G-K-D-G-T-K-V-E-F-K-A-D-K-F-E-W-N-Q-P-D-W-R-I-V-F-K-D-C | 346 |
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-Q-W-N-Q-P-D-W-R-I-V-F-K-D-C | 347 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-D-K-F-Q-W-N-Q-P-D-W-R-I-V-F-K-D-C | 348 |

TABLE 3-continued

APL-ID1 Peptides

| Sequence | SEQ ID NO. |
|---|---|
| E-T-K-V-V-Y-G-Y-L-K-E-G-R-T-V-K-L-D-S-H-R-F-D-W-Q-T-P-E-P-K-L-G-F-K-D-G-G-G-G-G-K-D-G-T-K-V-E-F-K-A-N-K-F-Q-W-N-Q-P-D-W-R-I-V-F-K-D-C | 349 |
| E-T-K-V-V-Y-I-Y-L-K-E-G-R-T-V-K-L-D-S-H-R-F-D-W-Q-T-P-E-P-K-L-G-F-K-D-G-G-G-G-G-K-D-G-T-K-V-E-F-K-A-N-K-F-Q-W-N-Q-P-D-W-R-I-V-F-K-D-C | 350 |

In some embodiments, the population of isolated peptides comprises three or more different peptides, wherein each peptide in the population comprises a sequence of C-K-D-G-T-$X_6$-V-E-$X_9$-K-A-$X_{12}$-K-F-$X_{15}$-W-N-$X_{18}$-P-D-$X_{21}$-R-I-$X_{24}$-F-K-$X_{27}$ (SEQ ID NO: 4), or a fragment thereof, wherein $X_6$ is an amino acid selected from the group consisting of K or Q, $X_9$ is an amino acid selected from the group consisting of F or V, $X_{12}$ is an amino acid selected from the group consisting of D or N, $X_{15}$ is an amino acid selected from the group consisting of E or Q, $X_{18}$ is an amino acid selected from the group consisting of S or Q, $X_{21}$ is an amino acid selected from the group consisting of F or W, $X_{24}$ is an amino acid selected from the group consisting of I or V, and $X_{27}$ is an amino acid selected from the group consisting of Q or D. In related embodiments, peptides of the invention comprise a sequence of SEQ ID NO: 4, wherein $X_6$ is Q, $X_9$ is F, and/or $X_{12}$ is N. In other embodiments, peptides of the invention comprise a sequence of SEQ ID NO: 4, wherein $X_{15}$ is E, $X_{18}$ is S, and/or $X_{21}$ is W. In still other embodiments, peptides of the invention comprise a sequence of SEQ ID NO: 4, wherein $X_{24}$ is I and/or $X_{27}$ is D. In particular embodiments, the population of isolated peptides comprises three or more peptides comprising or consisting of any one of the sequences in Table 4.

TABLE 4

APL-ID2 Peptides

| Sequence | SEQ ID NO. |
|---|---|
| C-K-D-G-T-K-V-E-F-K-A-D-K-F-E-W-N-S-P-D-F-R-I-I-F-K-Q | 351 |
| C-K-D-G-T-K-V-E-V-K-A-D-K-F-E-W-N-S-P-D-F-R-I-I-F-K-Q | 352 |
| C-K-D-G-T-Q-V-E-F-K-A-D-K-F-E-W-N-S-P-D-F-R-I-I-F-K-Q | 353 |
| C-K-D-G-T-Q-V-E-V-K-A-D-K-F-E-W-N-S-P-D-F-R-I-I-F-K-Q | 354 |
| C-K-D-G-T-K-V-E-F-K-A-N-K-F-E-W-N-S-P-D-F-R-I-I-F-K-Q | 355 |
| C-K-D-G-T-K-V-E-V-K-A-N-K-F-E-W-N-S-P-D-F-R-I-I-F-K-Q | 356 |
| C-K-D-G-T-Q-V-E-F-K-A-N-K-F-E-W-N-S-P-D-F-R-I-I-F-K-Q | 357 |
| C-K-D-G-T-Q-V-E-V-K-A-N-K-F-E-W-N-S-P-D-F-R-I-I-F-K-Q | 358 |
| C-K-D-G-T-K-V-E-F-K-A-D-K-F-Q-W-N-S-P-D-F-R-I-I-F-K-Q | 359 |
| C-K-D-G-T-K-V-E-V-K-A-D-K-F-Q-W-N-S-P-D-F-R-I-I-F-K-Q | 360 |
| C-K-D-G-T-Q-V-E-F-K-A-D-K-F-Q-W-N-S-P-D-F-R-I-I-F-K-Q | 361 |
| C-K-D-G-T-Q-V-E-V-K-A-D-K-F-Q-W-N-S-P-D-F-R-I-I-F-K-Q | 362 |
| C-K-D-G-T-K-V-E-F-K-A-N-K-F-Q-W-N-S-P-D-F-R-I-I-F-K-Q | 363 |
| C-K-D-G-T-K-V-E-V-K-A-N-K-F-Q-W-N-S-P-D-F-R-I-I-F-K-Q | 364 |
| C-K-D-G-T-Q-V-E-F-K-A-N-K-F-Q-W-N-S-P-D-F-R-I-I-F-K-Q | 365 |
| C-K-D-G-T-Q-V-E-V-K-A-N-K-F-Q-W-N-S-P-D-F-R-I-I-F-K-Q | 366 |
| C-K-D-G-T-K-V-E-F-K-A-D-K-F-Q-W-N-Q-P-D-F-R-I-I-F-K-Q | 367 |
| C-K-D-G-T-K-V-E-V-K-A-D-K-F-Q-W-N-Q-P-D-F-R-I-I-F-K-Q | 368 |
| C-K-D-G-T-Q-V-E-F-K-A-D-K-F-Q-W-N-Q-P-D-F-R-I-I-F-K-Q | 369 |
| C-K-D-G-T-Q-V-E-V-K-A-D-K-F-Q-W-N-Q-P-D-F-R-I-I-F-K-Q | 370 |
| C-K-D-G-T-K-V-E-F-K-A-N-K-F-Q-W-N-Q-P-D-F-R-I-I-F-K-Q | 371 |
| C-K-D-G-T-K-V-E-V-K-A-N-K-F-Q-W-N-Q-P-D-F-R-I-I-F-K-Q | 372 |

TABLE 4-continued

APL-ID2 Peptides

| Sequence | SEQ ID NO. |
|---|---|
| C-K-D-G-T-Q-V-E-F-K-A-N-K-F-Q-W-N-Q-P-D-F-R-I-I-F-K-Q | 373 |
| C-K-D-G-T-Q-V-E-V-K-A-N-K-F-Q-W-N-Q-P-D-F-R-I-I-F-K-Q | 374 |
| C-K-D-G-T-K-V-E-F-K-A-D-K-F-Q-W-N-Q-P-D-W-R-I-I-F-K-Q | 375 |
| C-K-D-G-T-K-V-E-V-K-A-D-K-F-Q-W-N-Q-P-D-W-R-I-I-F-K-Q | 376 |
| C-K-D-G-T-Q-V-E-F-K-A-D-K-F-Q-W-N-Q-P-D-W-R-I-I-F-K-Q | 377 |
| C-K-D-G-T-Q-V-E-V-K-A-D-K-F-Q-W-N-Q-P-D-W-R-I-I-F-K-Q | 378 |
| C-K-D-G-T-K-V-E-F-K-A-N-K-F-Q-W-N-Q-P-D-W-R-I-I-F-K-Q | 379 |
| C-K-D-G-T-K-V-E-V-K-A-N-K-F-Q-W-N-Q-P-D-W-R-I-I-F-K-Q | 380 |
| C-K-D-G-T-Q-V-E-F-K-A-N-K-F-Q-W-N-Q-P-D-W-R-I-I-F-K-Q | 381 |
| C-K-D-G-T-Q-V-E-V-K-A-N-K-F-Q-W-N-Q-P-D-W-R-I-I-F-K-Q | 382 |
| C-K-D-G-T-K-V-E-F-K-A-D-K-F-Q-W-N-Q-P-D-W-R-I-V-F-K-Q | 383 |
| C-K-D-G-T-K-V-E-V-K-A-D-K-F-Q-W-N-Q-P-D-W-R-I-V-F-K-Q | 384 |
| C-K-D-G-T-Q-V-E-F-K-A-D-K-F-Q-W-N-Q-P-D-W-R-I-V-F-K-Q | 385 |
| C-K-D-G-T-Q-V-E-V-K-A-D-K-F-Q-W-N-Q-P-D-W-R-I-V-F-K-Q | 386 |
| C-K-D-G-T-K-V-E-F-K-A-N-K-F-Q-W-N-Q-P-D-W-R-I-V-F-K-Q | 387 |
| C-K-D-G-T-K-V-E-V-K-A-N-K-F-Q-W-N-Q-P-D-W-R-I-V-F-K-Q | 388 |
| C-K-D-G-T-Q-V-E-F-K-A-N-K-F-Q-W-N-Q-P-D-W-R-I-V-F-K-Q | 389 |
| C-K-D-G-T-Q-V-E-V-K-A-N-K-F-Q-W-N-Q-P-D-W-R-I-V-F-K-Q | 390 |

In another embodiment of the invention, the population of isolated peptides comprises three or more different peptides, wherein each peptide in the population comprises a sequence of C-$X_2$-G-G-K-S-P-A-R-$X_{10}$-T-E-E-R-V-A-G-D-L-D-H-K-$X_{23}$-V-D-S-D-K-K-H-D-A-E-K-T-E-E-K-R-H (SEQ ID NO: 5), or a fragment thereof, wherein $X_2$ is an amino acid selected from the group consisting of I or V, $X_{10}$ is an amino acid selected from the group consisting of S or Y, and $X_{23}$ is an amino acid selected from the group consisting of E or N. In related embodiments, peptides of the invention comprise a sequence of SEQ ID NO: 5, wherein $X_2$ is V. In other embodiments, peptides of the invention comprise a sequence of SEQ ID NO: 5, wherein $X_{10}$ is Y. In still other embodiments, peptides of the invention comprise a sequence of SEQ ID NO: 5, wherein $X_{23}$ is E. In some embodiments, the population of isolated peptides comprises three or more peptides comprising or consisting of any one of the sequences in Table 5.

TABLE 5

APL-ID3 Peptides

| Sequence | SEQ ID NO. |
|---|---|
| C-I-G-G-K-S-P-A-R-S-T-E-E-R-V-A-G-D-L-D-H-K-E-V-D-S-D-K-K-H-D-A-E-K-T-E-E-K-R-H | 399 |
| C-I-G-G-K-S-P-A-R-Y-T-E-E-R-V-A-G-D-L-D-H-K-E-V-D-S-D-K-K-H-D-A-E-K-T-E-E-K-R-H | 400 |
| C-V-G-G-K-S-P-A-R-S-T-E-E-R-V-A-G-D-L-D-H-K-E-V-D-S-D-K-K-H-D-A-E-K-T-E-E-K-R-H | 401 |
| C-V-G-G-K-S-P-A-R-Y-T-E-E-R-V-A-G-D-L-D-H-K-E-V-D-S-D-K-K-H-D-A-E-K-T-E-E-K-R-H | 402 |
| C-I-G-G-K-S-P-A-R-S-T-E-E-R-V-A-G-D-L-D-H-K-N-V-D-S-D-K-K-H-D-A-E-K-T-E-E-K-R-H | 403 |
| C-I-G-G-K-S-P-A-R-Y-T-E-E-R-V-A-G-D-L-D-H-K-N-V-D-S-D-K-K-H-D-A-E-K-T-E-E-K-R-H | 404 |
| C-V-G-G-K-S-P-A-R-S-T-E-E-R-V-A-G-D-L-D-H-K-N-V-D-S-D-K-K-H-D-A-E-K-T-E-E-K-R-H | 405 |
| C-V-G-G-K-S-P-A-R-Y-T-E-E-R-V-A-G-D-L-D-H-K-N-V-D-S-D-K-K-H-D-A-E-K-T-E-E-K-R-H | 406 |

In one embodiment, the peptides of the invention comprise a sequence of C-G-K-I-L-N-L-V-S-A-V-Q-E-K-K-P-P-E-A-P-A-A-D-E-A-A-G-P-A-T-H (SEQ ID NO: 6), or a fragment thereof. The population of isolated peptides may comprise three or more peptides, each peptide comprising a sequence of SEQ ID NO: 6 or fragments of this sequence. In some embodiments, peptides comprising the sequence of SEQ ID NO: 6 may be included in other peptide populations of the invention described herein.

In another embodiment of the invention, the population of isolated peptides comprises three or more different peptides, wherein each peptide in the population comprises a sequence of C-K-D-G-$X_5$-R-V-E-$X_9$-K-A-E-$X_{13}$-F-N-$X_{16}$-Q-$X_{18}$-P-N-P-$X_{22}$-I-K-Y-R-$X_{27}$ (SEQ ID NO: 7), or a fragment thereof, wherein $X_5$ is an amino acid selected from the group consisting of S or Q, $X_9$ is an amino acid selected from the group consisting of F or Y, $X_{13}$ is an amino acid selected from the group consisting of R or H, $X_{16}$ is an amino acid selected from the group consisting of W or Y, $X_{18}$ is an amino acid selected from the group consisting of S or Q, $X_{22}$ is an amino acid selected from the group consisting of K or H, and $X_{27}$ is an amino acid selected from the group consisting of N or D.

In related embodiments, peptides of the invention comprise a sequence of SEQ ID NO: 7, wherein $X_5$ is Q, $X_9$ is Y, and/or $X_{13}$ is H. In other embodiments, peptides of the invention comprise a sequence of SEQ ID NO: 7, wherein $X_{16}$ is W and/or $X_{22}$ is K. In still other embodiments, peptides of the invention comprise a sequence of SEQ ID NO: 7, wherein $X_{18}$ is S and/or $X_{27}$ is D. In some embodiments, the population of isolated peptides comprises three or more peptides comprising or consisting of any one of the sequences in Table 6.

TABLE 6

APL-ID6 Peptides

| Sequence | SEQ ID NO. |
|---|---|
| C-K-D-G-S-R-V-E-F-K-A-E-R-F-N-W-Q-S-P-N-P-K-I-K-Y-R-N | 407 |
| C-K-D-G-S-R-V-E-Y-K-A-E-R-F-N-W-Q-S-P-N-P-K-I-K-Y-R-N | 408 |
| C-K-D-G-Q-R-V-E-F-K-A-E-R-F-N-W-Q-S-P-N-P-K-I-K-Y-R-N | 409 |
| C-K-D-G-Q-R-V-E-Y-K-A-E-R-F-N-W-Q-S-P-N-P-K-I-K-Y-R-N | 410 |
| C-K-D-G-S-R-V-E-F-K-A-E-H-F-N-W-Q-S-P-N-P-K-I-K-Y-R-N | 411 |
| C-K-D-G-S-R-V-E-Y-K-A-E-H-F-N-W-Q-S-P-N-P-K-I-K-Y-R-N | 412 |
| C-K-D-G-Q-R-V-E-F-K-A-E-H-F-N-W-Q-S-P-N-P-K-I-K-Y-R-N | 413 |
| C-K-D-G-Q-R-V-E-Y-K-A-E-H-F-N-W-Q-S-P-N-P-K-I-K-Y-R-N | 414 |
| C-K-D-G-S-R-V-E-F-K-A-E-R-F-N-Y-Q-S-P-N-P-K-I-K-Y-R-N | 415 |
| C-K-D-G-S-R-V-E-Y-K-A-E-R-F-N-Y-Q-S-P-N-P-K-I-K-Y-R-N | 416 |
| C-K-D-G-Q-R-V-E-F-K-A-E-R-F-N-Y-Q-S-P-N-P-K-I-K-Y-R-N | 417 |
| C-K-D-G-Q-R-V-E-Y-K-A-E-R-F-N-Y-Q-S-P-N-P-K-I-K-Y-R-N | 418 |
| C-K-D-G-S-R-V-E-F-K-A-E-H-F-N-Y-Q-S-P-N-P-K-I-K-Y-R-N | 419 |
| C-K-D-G-S-R-V-E-Y-K-A-E-H-F-N-Y-Q-S-P-N-P-K-I-K-Y-R-N | 420 |
| C-K-D-G-Q-R-V-E-F-K-A-E-H-F-N-Y-Q-S-P-N-P-K-I-K-Y-R-N | 421 |
| C-K-D-G-Q-R-V-E-Y-K-A-E-H-F-N-Y-Q-S-P-N-P-K-I-K-Y-R-N | 422 |
| C-K-D-G-S-R-V-E-F-K-A-E-R-F-N-W-Q-Q-P-N-P-K-I-K-Y-R-N | 423 |
| C-K-D-G-S-R-V-E-Y-K-A-E-R-F-N-W-Q-Q-P-N-P-K-I-K-Y-R-N | 424 |
| C-K-D-G-Q-R-V-E-F-K-A-E-R-F-N-W-Q-Q-P-N-P-K-I-K-Y-R-N | 425 |
| C-K-D-G-Q-R-V-E-Y-K-A-E-R-F-N-W-Q-Q-P-N-P-K-I-K-Y-R-N | 426 |
| C-K-D-G-S-R-V-E-F-K-A-E-H-F-N-W-Q-Q-P-N-P-K-I-K-Y-R-N | 427 |
| C-K-D-G-S-R-V-E-Y-K-A-E-H-F-N-W-Q-Q-P-N-P-K-I-K-Y-R-N | 428 |
| C-K-D-G-Q-R-V-E-F-K-A-E-H-F-N-W-Q-Q-P-N-P-K-I-K-Y-R-N | 429 |
| C-K-D-G-Q-R-V-E-Y-K-A-E-H-F-N-W-Q-Q-P-N-P-K-I-K-Y-R-N | 430 |
| C-K-D-G-S-R-V-E-F-K-A-E-R-F-N-Y-Q-Q-P-N-P-K-I-K-Y-R-N | 431 |
| C-K-D-G-S-R-V-E-Y-K-A-E-R-F-N-Y-Q-Q-P-N-P-K-I-K-Y-R-N | 432 |
| C-K-D-G-Q-R-V-E-F-K-A-E-R-F-N-Y-Q-Q-P-N-P-K-I-K-Y-R-N | 433 |
| C-K-D-G-Q-R-V-E-Y-K-A-E-R-F-N-Y-Q-Q-P-N-P-K-I-K-Y-R-N | 434 |
| C-K-D-G-S-R-V-E-F-K-A-E-H-F-N-Y-Q-Q-P-N-P-K-I-K-Y-R-N | 435 |
| C-K-D-G-S-R-V-E-Y-K-A-E-H-F-N-Y-Q-Q-P-N-P-K-I-K-Y-R-N | 436 |
| C-K-D-G-Q-R-V-E-F-K-A-E-H-F-N-Y-Q-Q-P-N-P-K-I-K-Y-R-N | 437 |
| C-K-D-G-Q-R-V-E-Y-K-A-E-H-F-N-Y-Q-Q-P-N-P-K-I-K-Y-R-N | 438 |
| C-K-D-G-Q-R-V-E-F-K-A-E-H-F-N-W-Q-Q-P-N-P-H-I-K-Y-R-N | 439 |
| C-K-D-G-Q-R-V-E-Y-K-A-E-H-F-N-W-Q-Q-P-N-P-H-I-K-Y-R-N | 440 |
| C-K-D-G-S-R-V-E-F-K-A-E-R-F-N-Y-Q-Q-P-N-P-H-I-K-Y-R-N | 441 |
| C-K-D-G-S-R-V-E-Y-K-A-E-R-F-N-Y-Q-Q-P-N-P-H-I-K-Y-R-N | 442 |
| C-K-D-G-Q-R-V-E-F-K-A-E-R-F-N-Y-Q-Q-P-N-P-H-I-K-Y-R-N | 443 |
| C-K-D-G-Q-R-V-E-Y-K-A-E-R-F-N-Y-Q-Q-P-N-P-H-I-K-Y-R-N | 444 |

TABLE 6-continued

APL-ID6 Peptides

| Sequence | SEQ ID NO. |
|---|---|
| C-K-D-G-S-R-V-E-F-K-A-E-H-F-N-Y-Q-Q-P-N-P-H-I-K-Y-R-N | 445 |
| C-K-D-G-S-R-V-E-Y-K-A-E-H-F-N-Y-Q-Q-P-N-P-H-I-K-Y-R-N | 446 |
| C-K-D-G-Q-R-V-E-F-K-A-E-H-F-N-Y-Q-Q-P-N-P-H-I-K-Y-R-N | 447 |
| C-K-D-G-Q-R-V-E-Y-K-A-E-H-F-N-Y-Q-Q-P-N-P-H-I-K-Y-R-N | 448 |
| C-K-D-G-Q-R-V-E-F-K-A-E-H-F-N-W-Q-Q-P-N-P-H-I-K-Y-R-D | 449 |

In some embodiments of the invention, the population of isolated peptides comprises three or more different peptides, wherein each peptide in the population comprises a sequence of C-G-K-I-L-N-L-V-S-$X_{10}$-$X_{11}$-N-E-K-K-P-P-E-A-P-A-A-D-E-A-A-G-P-A-T-H (SEQ ID NO: 8), or a fragment thereof, wherein $X_{10}$ is an amino acid selected from the group consisting of V, L or I, and $X_{11}$ is an amino acid selected from the group consisting of A or L. In such embodiments, peptides of the invention comprise a sequence of SEQ ID NO: 8, wherein $X_{11}$ is A. In other embodiments, peptides of the invention comprise a sequence of SEQ ID NO: 8, wherein $X_{10}$ is I. In still other embodiments, the population of isolated peptides comprises three or more peptides comprising or consisting of any one of the sequences in Table 7.

TABLE 7

APL-ID7 Peptides

| Sequence | SEQ ID NO. |
|---|---|
| C-G-K-I-L-N-L-V-S-V-A-N-E-K-K-P-P-E-A-P-A-A-D-E-A-A-G-P-A-T-H | 459 |
| C-G-K-I-L-N-L-V-S-V-L-N-E-K-K-P-P-E-A-P-A-A-D-E-A-A-G-P-A-T-H | 460 |
| C-G-K-I-L-N-L-V-S-L-A-N-E-K-K-P-P-E-A-P-A-A-D-E-A-A-G-P-A-T-H | 461 |
| C-G-K-I-L-N-L-V-S-L-L-N-E-K-K-P-P-E-A-P-A-A-D-E-A-A-G-P-A-T-H | 462 |
| C-G-K-I-L-N-L-V-S-I-A-N-E-K-K-P-P-E-A-P-A-A-D-E-A-A-G-P-A-T-H | 463 |
| C-G-K-I-L-N-L-V-S-I-L-N-E-K-K-P-P-E-A-P-A-A-D-E-A-A-G-P-A-T-H | 464 |

TABLE 6-continued

APL-ID6 Peptides

| Sequence | SEQ ID NO. |
|---|---|
| C-K-D-G-Q-R-V-E-Y-K-A-E-H-F-N-W-Q-Q-P-N-P-H-I-K-Y-R-D | 450 |
| C-K-D-G-S-R-V-E-F-K-A-E-R-F-N-Y-Q-Q-P-N-P-H-I-K-Y-R-D | 451 |
| C-K-D-G-S-R-V-E-Y-K-A-E-R-F-N-Y-Q-Q-P-N-P-H-I-K-Y-R-D | 452 |
| C-K-D-G-Q-R-V-E-F-K-A-E-R-F-N-Y-Q-Q-P-N-P-H-I-K-Y-R-D | 453 |
| C-K-D-G-Q-R-V-E-Y-K-A-E-R-F-N-Y-Q-Q-P-N-P-H-I-K-Y-R-D | 454 |
| C-K-D-G-S-R-V-E-F-K-A-E-H-F-N-Y-Q-Q-P-N-P-H-I-K-Y-R-D | 455 |
| C-K-D-G-S-R-V-E-Y-K-A-E-H-F-N-Y-Q-Q-P-N-P-H-I-K-Y-R-D | 456 |
| C-K-D-G-Q-R-V-E-F-K-A-E-H-F-N-Y-Q-Q-P-N-P-H-I-K-Y-R-D | 457 |
| C-K-D-G-Q-R-V-E-Y-K-A-E-H-F-N-Y-Q-Q-P-N-P-H-I-K-Y-R-D | 458 |

In other embodiments of the invention, the population of isolated peptides comprises three or more different peptides, wherein each peptide in the population comprises a sequence of E-T-K-V-$X_5$-Y-$X_7$-Y-L-K-$X_{11}$-G-R-T-V-K-L-D-S-H-$X_{21}$-F-D-W-$X_{25}$-T-P-$X_{28}$-P-K-$X_{31}$-G-F-K-D-C (SEQ ID NO: 9), or a fragment thereof, wherein $X_5$ is an amino acid selected from the group consisting of V or A, $X_7$ is an amino acid selected from the group consisting of G, I or H, $X_{11}$ is an amino acid selected from the group consisting of E, N, or Q, $X_{21}$ is an amino acid selected from the group consisting of R, D, or N, $X_{25}$ is an amino acid selected from the group consisting of Q, D, or E, $X_{28}$ is an amino acid selected from the group consisting of E or N, and $X_{31}$ is an amino acid selected from the group consisting of L or V.

In related embodiments, peptides of the invention comprise a sequence of SEQ ID NO: 9, wherein $X_5$ is V, $X_7$ is G, and/or $X_{11}$ is N. In other embodiments, peptides of the invention comprise a sequence of SEQ ID NO: 9, wherein $X_{21}$ is R and/or $X_{25}$ is E. In still other embodiments, peptides of the invention comprise a sequence of SEQ ID NO: 9, wherein $X_{28}$ is N and/or $X_{31}$ is L. In some embodiments, the population of isolated peptides comprises three or more peptides comprising or consisting of any one of the sequences in Table 8.

TABLE 8

APID 2-1 Peptides

| Sequence | SEQ ID NO. |
|---|---|
| E-T-K-V-V-Y-G-Y-L-K-E-G-R-T-V-K-L-D-S-H-R-F-D-W-Q-T-P-E-P-K-L-G-F-K-D-C | 465 |
| E-T-K-V-V-Y-I-Y-L-K-E-G-R-T-V-K-L-D-S-H-R-F-D-W-Q-T-P-E-P-K-L-G-F-K-D-C | 466 |
| E-T-K-V-V-Y-H-Y-L-K-E-G-R-T-V-K-L-D-S-H-R-F-D-W-Q-T-P-E-P-K-L-G-F-K-D-C | 467 |
| E-T-K-V-A-Y-G-Y-L-K-E-G-R-T-V-K-L-D-S-H-R-F-D-W-Q-T-P-E-P-K-L-G-F-K-D-C | 468 |
| E-T-K-V-A-Y-I-Y-L-K-E-G-R-T-V-K-L-D-S-H-R-F-D-W-Q-T-P-E-P-K-L-G-F-K-D-C | 469 |
| E-T-K-V-A-Y-H-Y-L-K-E-G-R-T-V-K-L-D-S-H-R-F-D-W-Q-T-P-E-P-K-L-G-F-K-D-C | 470 |
| E-T-K-V-V-Y-G-Y-L-K-N-G-R-T-V-K-L-D-S-H-R-F-D-W-Q-T-P-E-P-K-L-G-F-K-D-C | 471 |
| E-T-K-V-V-Y-I-Y-L-K-N-G-R-T-V-K-L-D-S-H-R-F-D-W-Q-T-P-E-P-K-L-G-F-K-D-C | 472 |
| E-T-K-V-V-Y-H-Y-L-K-N-G-R-T-V-K-L-D-S-H-R-F-D-W-Q-T-P-E-P-K-L-G-F-K-D-C | 473 |
| E-T-K-V-A-Y-G-Y-L-K-N-G-R-T-V-K-L-D-S-H-R-F-D-W-Q-T-P-E-P-K-L-G-F-K-D-C | 474 |
| E-T-K-V-A-Y-I-Y-L-K-N-G-R-T-V-K-L-D-S-H-R-F-D-W-Q-T-P-E-P-K-L-G-F-K-D-C | 475 |
| E-T-K-V-A-Y-H-Y-L-K-N-G-R-T-V-K-L-D-S-H-R-F-D-W-Q-T-P-E-P-K-L-G-F-K-D-C | 476 |
| E-T-K-V-V-Y-G-Y-L-K-Q-G-R-T-V-K-L-D-S-H-R-F-D-W-Q-T-P-E-P-K-L-G-F-K-D-C | 477 |
| E-T-K-V-V-Y-I-Y-L-K-Q-G-R-T-V-K-L-D-S-H-R-F-D-W-Q-T-P-E-P-K-L-G-F-K-D-C | 478 |
| E-T-K-V-V-Y-H-Y-L-K-Q-G-R-T-V-K-L-D-S-H-R-F-D-W-Q-T-P-E-P-K-L-G-F-K-D-C | 479 |
| E-T-K-V-A-Y-G-Y-L-K-Q-G-R-T-V-K-L-D-S-H-R-F-D-W-Q-T-P-E-P-K-L-G-F-K-D-C | 480 |
| E-T-K-V-A-Y-I-Y-L-K-Q-G-R-T-V-K-L-D-S-H-R-F-D-W-Q-T-P-E-P-K-L-G-F-K-D-C | 481 |
| E-T-K-V-A-Y-H-Y-L-K-Q-G-R-T-V-K-L-D-S-H-R-F-D-W-Q-T-P-E-P-K-L-G-F-K-D-C | 482 |
| E-T-K-V-V-Y-G-Y-L-K-Q-G-R-T-V-K-L-D-S-H-D-F-D-W-Q-T-P-E-P-K-L-G-F-K-D-C | 483 |
| E-T-K-V-V-Y-I-Y-L-K-Q-G-R-T-V-K-L-D-S-H-D-F-D-W-Q-T-P-E-P-K-L-G-F-K-D-C | 484 |
| E-T-K-V-V-Y-H-Y-L-K-Q-G-R-T-V-K-L-D-S-H-D-F-D-W-Q-T-P-E-P-K-L-G-F-K-D-C | 485 |
| E-T-K-V-A-Y-G-Y-L-K-Q-G-R-T-V-K-L-D-S-H-D-F-D-W-Q-T-P-E-P-K-L-G-F-K-D-C | 486 |
| E-T-K-V-A-Y-I-Y-L-K-Q-G-R-T-V-K-L-D-S-H-D-F-D-W-Q-T-P-E-P-K-L-G-F-K-D-C | 487 |
| E-T-K-V-A-Y-H-Y-L-K-Q-G-R-T-V-K-L-D-S-H-D-F-D-W-Q-T-P-E-P-K-L-G-F-K-D-C | 488 |
| E-T-K-V-V-Y-G-Y-L-K-Q-G-R-T-V-K-L-D-S-H-N-F-D-W-Q-T-P-E-P-K-L-G-F-K-D-C | 489 |
| E-T-K-V-V-Y-I-Y-L-K-Q-G-R-T-V-K-L-D-S-H-N-F-D-W-Q-T-P-E-P-K-L-G-F-K-D-C | 490 |
| E-T-K-V-V-Y-H-Y-L-K-Q-G-R-T-V-K-L-D-S-H-N-F-D-W-Q-T-P-E-P-K-L-G-F-K-D-C | 491 |
| E-T-K-V-A-Y-G-Y-L-K-Q-G-R-T-V-K-L-D-S-H-N-F-D-W-Q-T-P-E-P-K-L-G-F-K-D-C | 492 |
| E-T-K-V-A-Y-I-Y-L-K-Q-G-R-T-V-K-L-D-S-H-N-F-D-W-Q-T-P-E-P-K-L-G-F-K-D-C | 493 |
| E-T-K-V-A-Y-H-Y-L-K-Q-G-R-T-V-K-L-D-S-H-N-F-D-W-Q-T-P-E-P-K-L-G-F-K-D-C | 494 |
| E-T-K-V-V-Y-G-Y-L-K-Q-G-R-T-V-K-L-D-S-H-D-F-D-W-D-T-P-E-P-K-L-G-F-K-D-C | 495 |
| E-T-K-V-V-Y-I-Y-L-K-Q-G-R-T-V-K-L-D-S-H-D-F-D-W-D-T-P-E-P-K-L-G-F-K-D-C | 496 |
| E-T-K-V-V-Y-H-Y-L-K-Q-G-R-T-V-K-L-D-S-H-D-F-D-W-D-T-P-E-P-K-L-G-F-K-D-C | 497 |
| E-T-K-V-A-Y-G-Y-L-K-Q-G-R-T-V-K-L-D-S-H-D-F-D-W-D-T-P-E-P-K-L-G-F-K-D-C | 498 |
| E-T-K-V-A-Y-I-Y-L-K-Q-G-R-T-V-K-L-D-S-H-D-F-D-W-D-T-P-E-P-K-L-G-F-K-D-C | 499 |
| E-T-K-V-A-Y-H-Y-L-K-Q-G-R-T-V-K-L-D-S-H-D-F-D-W-D-T-P-E-P-K-L-G-F-K-D-C | 500 |
| E-T-K-V-V-Y-G-Y-L-K-Q-G-R-T-V-K-L-D-S-H-N-F-D-W-D-T-P-E-P-K-L-G-F-K-D-C | 501 |
| E-T-K-V-V-Y-I-Y-L-K-Q-G-R-T-V-K-L-D-S-H-N-F-D-W-D-T-P-E-P-K-L-G-F-K-D-C | 502 |

TABLE 8-continued

APID 2-1 Peptides

| Sequence | SEQ ID NO. |
|---|---|
| E-T-K-V-V-Y-H-Y-L-K-Q-G-R-T-V-K-L-D-S-H-N-F-D-W-D-T-P-E-P-K-L-G-F-K-D-C | 503 |
| E-T-K-V-A-Y-G-Y-L-K-Q-G-R-T-V-K-L-D-S-H-N-F-D-W-D-T-P-E-P-K-L-G-F-K-D-C | 504 |
| E-T-K-V-A-Y-I-Y-L-K-Q-G-R-T-V-K-L-D-S-H-N-F-D-W-D-T-P-E-P-K-L-G-F-K-D-C | 505 |
| E-T-K-V-A-Y-H-Y-L-K-Q-G-R-T-V-K-L-D-S-H-N-F-D-W-D-T-P-E-P-K-L-G-F-K-D-C | 506 |
| E-T-K-V-V-Y-G-Y-L-K-Q-G-R-T-V-K-L-D-S-H-D-F-D-W-E-T-P-E-P-K-L-G-F-K-D-C | 507 |
| E-T-K-V-V-Y-I-Y-L-K-Q-G-R-T-V-K-L-D-S-H-D-F-D-W-E-T-P-E-P-K-L-G-F-K-D-C | 508 |
| E-T-K-V-V-Y-H-Y-L-K-Q-G-R-T-V-K-L-D-S-H-D-F-D-W-E-T-P-E-P-K-L-G-F-K-D-C | 509 |
| E-T-K-V-A-Y-G-Y-L-K-Q-G-R-T-V-K-L-D-S-H-D-F-D-W-E-T-P-E-P-K-L-G-F-K-D-C | 510 |
| E-T-K-V-A-Y-I-Y-L-K-Q-G-R-T-V-K-L-D-S-H-D-F-D-W-E-T-P-E-P-K-L-G-F-K-D-C | 511 |
| E-T-K-V-A-Y-H-Y-L-K-Q-G-R-T-V-K-L-D-S-H-D-F-D-W-E-T-P-E-P-K-L-G-F-K-D-C | 512 |
| E-T-K-V-V-Y-G-Y-L-K-Q-G-R-T-V-K-L-D-S-H-N-F-D-W-E-T-P-E-P-K-L-G-F-K-D-C | 513 |
| E-T-K-V-V-Y-I-Y-L-K-Q-G-R-T-V-K-L-D-S-H-N-F-D-W-E-T-P-E-P-K-L-G-F-K-D-C | 514 |
| E-T-K-V-V-Y-H-Y-L-K-Q-G-R-T-V-K-L-D-S-H-N-F-D-W-E-T-P-E-P-K-L-G-F-K-D-C | 515 |
| E-T-K-V-A-Y-G-Y-L-K-Q-G-R-T-V-K-L-D-S-H-N-F-D-W-E-T-P-E-P-K-L-G-F-K-D-C | 516 |
| E-T-K-V-A-Y-I-Y-L-K-Q-G-R-T-V-K-L-D-S-H-N-F-D-W-E-T-P-E-P-K-L-G-F-K-D-C | 517 |
| E-T-K-V-A-Y-H-Y-L-K-Q-G-R-T-V-K-L-D-S-H-N-F-D-W-E-T-P-E-P-K-L-G-F-K-D-C | 518 |
| E-T-K-V-V-Y-G-Y-L-K-Q-G-R-T-V-K-L-D-S-H-D-F-D-W-E-T-P-N-P-K-L-G-F-K-D-C | 519 |
| E-T-K-V-V-Y-I-Y-L-K-Q-G-R-T-V-K-L-D-S-H-D-F-D-W-E-T-P-N-P-K-L-G-F-K-D-C | 520 |
| E-T-K-V-V-Y-H-Y-L-K-Q-G-R-T-V-K-L-D-S-H-D-F-D-W-E-T-P-N-P-K-L-G-F-K-D-C | 521 |
| E-T-K-V-A-Y-G-Y-L-K-Q-G-R-T-V-K-L-D-S-H-D-F-D-W-E-T-P-N-P-K-L-G-F-K-D-C | 522 |
| E-T-K-V-A-Y-I-Y-L-K-Q-G-R-T-V-K-L-D-S-H-D-F-D-W-E-T-P-N-P-K-L-G-F-K-D-C | 523 |
| E-T-K-V-A-Y-H-Y-L-K-Q-G-R-T-V-K-L-D-S-H-D-F-D-W-E-T-P-N-P-K-L-G-F-K-D-C | 524 |
| E-T-K-V-V-Y-G-Y-L-K-Q-G-R-T-V-K-L-D-S-H-N-F-D-W-E-T-P-N-P-K-L-G-F-K-D-C | 525 |
| E-T-K-V-V-Y-I-Y-L-K-Q-G-R-T-V-K-L-D-S-H-N-F-D-W-E-T-P-N-P-K-L-G-F-K-D-C | 526 |
| E-T-K-V-V-Y-H-Y-L-K-Q-G-R-T-V-K-L-D-S-H-N-F-D-W-E-T-P-N-P-K-L-G-F-K-D-C | 527 |
| E-T-K-V-A-Y-G-Y-L-K-Q-G-R-T-V-K-L-D-S-H-N-F-D-W-E-T-P-N-P-K-L-G-F-K-D-C | 528 |
| E-T-K-V-A-Y-I-Y-L-K-Q-G-R-T-V-K-L-D-S-H-N-F-D-W-E-T-P-N-P-K-L-G-F-K-D-C | 529 |
| E-T-K-V-A-Y-H-Y-L-K-Q-G-R-T-V-K-L-D-S-H-N-F-D-W-E-T-P-N-P-K-L-G-F-K-D-C | 530 |
| E-T-K-V-V-Y-G-Y-L-K-Q-G-R-T-V-K-L-D-S-H-D-F-D-W-E-T-P-N-P-K-V-G-F-K-D-C | 531 |
| E-T-K-V-V-Y-I-Y-L-K-Q-G-R-T-V-K-L-D-S-H-D-F-D-W-E-T-P-N-P-K-V-G-F-K-D-C | 532 |
| E-T-K-V-V-Y-H-Y-L-K-Q-G-R-T-V-K-L-D-S-H-D-F-D-W-E-T-P-N-P-K-V-G-F-K-D-C | 533 |
| E-T-K-V-A-Y-G-Y-L-K-Q-G-R-T-V-K-L-D-S-H-D-F-D-W-E-T-P-N-P-K-V-G-F-K-D-C | 534 |
| E-T-K-V-A-Y-I-Y-L-K-Q-G-R-T-V-K-L-D-S-H-D-F-D-W-E-T-P-N-P-K-V-G-F-K-D-C | 535 |
| E-T-K-V-A-Y-H-Y-L-K-Q-G-R-T-V-K-L-D-S-H-D-F-D-W-E-T-P-N-P-K-V-G-F-K-D-C | 536 |
| E-T-K-V-V-Y-G-Y-L-K-Q-G-R-T-V-K-L-D-S-H-N-F-D-W-E-T-P-N-P-K-V-G-F-K-D-C | 537 |
| E-T-K-V-V-Y-I-Y-L-K-Q-G-R-T-V-K-L-D-S-H-N-F-D-W-E-T-P-N-P-K-V-G-F-K-D-C | 538 |
| E-T-K-V-V-Y-H-Y-L-K-Q-G-R-T-V-K-L-D-S-H-N-F-D-W-E-T-P-N-P-K-V-G-F-K-D-C | 539 |

TABLE 8-continued

APID 2-1 Peptides

| Sequence | SEQ ID NO. |
|---|---|
| E-T-K-V-A-Y-G-Y-L-K-Q-G-R-T-V-K-L-D-S-H-N-F-D-W-E-T-P-N-P-K-V-G-F-K-D-C | 540 |
| E-T-K-V-A-Y-I-Y-L-K-Q-G-R-T-V-K-L-D-S-H-N-F-D-W-E-T-P-N-P-K-V-G-F-K-D-C | 541 |
| E-T-K-V-A-Y-H-Y-L-K-Q-G-R-T-V-K-L-D-S-H-N-F-D-W-E-T-P-N-P-K-V-G-F-K-D-C | 542 |

In certain embodiments, peptides of the invention comprise a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and an additional N-terminal peptide sequence (e.g., an N-terminal extension). The additional N-terminal peptide sequence can comprise 1, 2, 3, 4, 5, 6, 7, 8, 9, 10, 11, 12, 13, 14, 15, 20, 25, or more amino acids. In certain embodiments, the N-terminal peptide sequence has a length of about 5 to about 10, about 10 to about 15, about 15 to about 20, about 20 to about 25, about 25 to about 30, about 30 to about 40, or about 40 to about 50 amino acids. In one embodiment, the N-terminal peptide sequence can be one or more linking residues (e.g. one or more glycine, cysteine, or serine residues). For instance, in certain embodiments, the carboxyl-terminal cysteine residue in any of the sequences described herein can be located at the amino terminus instead. In a similar manner, the amino-terminal cysteine residue in any of the sequences described herein can be located at the carboxyl terminus instead.

The additional N-terminal peptide sequence can be a native sequence. As used herein, a "native" sequence is a peptide sequence from a naturally-occurring *Anaplasma* major surface protein 2 (MSP2)/p44 or OMP/p44 sequence, or a variant thereof. In certain embodiments, the peptide sequence is a fragment of a naturally-occurring *Anaplasma* MSP 2/p44 or OMP/p44 sequence. The peptide sequence can be, e.g., from a conserved or non-conserved region of MSP 2/p44 or OMP/p44. The peptide sequence can comprise, e.g., an epitope, such as an immunodominant epitope or any other epitope recognizable by a host (e.g., human, dog, etc.) immune system. *Anaplasma* MSP 2/p44 or OMP/p44 proteins and peptides thereof have been described, e.g., in Genebank Accession Nos. AA030097.1, ACV85580.1, ACV85559.1, AEH96270.1, ADU56850.1, AEH96270.1, and AAQ91849.1 as well as in U.S. Pat. Nos. 7,507,789, 8,303,959, 8,158,370, and U.S. Patent Publication No. 2013/0064842, the contents of each of which are incorporated herein by reference in their entireties.

Variant polypeptides are at least about 80, 85, 90, 95, 98, or 99% identical to a peptide shown in SEQ ID NOs: 1-543 and are also polypeptides of the invention. Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants of the peptide sequences can be readily selected by one of skill in the art, based in part on known properties of the sequence. For example, a variant peptide can include amino acid substitutions (e.g., conservative amino acid substitutions) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted amino acids can be contiguous or non-contiguous. Conservative amino acid substitutions are those that take place within a family of amino acids that are related in their side chains and chemical properties. These include, e.g., (1) acidic amino acids: aspartate, glutamate; (2) basic amino acids: lysine, arginine, histidine; (3) nonpolar amino acids: alanine, valine, leucine, isoleucine, proline, phenylalanine, methionine, tryptophan; (4) uncharged polar amino acids: glycine, asparagine, glutamine, cysteine, serine, threonine, tyrosine; (5) aliphatic amino acids: glycine, alanine, valine, leucine, isoleucine, serine, threonine, with serine and threonine optionally grouped separately as aliphatic-hydroxyl; (6) aromatic amino acids: phenylalanine, tyrosine, tryptophan; (7) amide amino acids: asparagine, glutamine; and (9) sulfur-containing amino acids: cysteine and methionine. See, e.g., Biochemistry, 2nd ed., Ed. by L. Stryer, W H Freeman and Co.: 1981. Methods for confirming that variant peptides are suitable are conventional and routine.

Variants of the peptide sequences encompass variations on previously defined peptide sequences. For example, a previously described peptide sequence comprising a known epitope may be lengthened or shortened, at one or both ends (e.g., by about 1-3 amino acids), and/or one, two, three, four or more amino acids may be substituted by conservative amino acids, etc. Furthermore, if a region of a protein has been identified as containing an epitope of interest, an investigator can "shift" the region of interest (e.g., by about 5 amino acids in either direction) from the endpoints of the original rough region to optimize the activity.

In certain embodiments, the additional N-terminal peptide sequence can comprise or consist of another peptide having a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. Thus, in some embodiments, a peptide of the invention can be a multimer of sequences having a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In other embodiments, the N-terminal peptide sequence is a native MSP 2/p44 or OMP/p44 peptide sequence that is naturally adjacent to the N-terminal end of a sequence of any one of SEQ ID NOs: 1 to 9. In other embodiments, the peptide can comprise a fusion of sequences of any one of SEQ ID NOs: 1 to 9 optionally through one or more linking amino acids. For example, in one embodiment, the peptide can comprise a sequence of SEQ ID NO: 1 or SEQ ID NO: 2 linked to SEQ ID NO: 4 optionally through one or more linking amino acids (e.g. glycine, serine, or cysteine residues). In another embodiment, the peptide can comprise a sequence of SEQ ID NO: 5 linked to SEQ ID NO: 4 or SEQ ID NO: 6 optionally through one or more linking amino acids (e.g. glycine, serine, or cysteine residues). In another embodiment, the peptide can comprise a sequence of SEQ ID NO: 9 linked to SEQ ID NO: 4, SEQ ID NO: 7, or SEQ ID NO: 8 optionally through one or more linking amino acids (e.g. glycine, serine, or cysteine residues).

In certain embodiments, the additional N-terminal peptide sequence is a non-native sequence. As used herein, a "non-native" sequence is any protein sequence, whether from an *Anaplasma* protein or otherwise, other than a native MSP 2/p44 or OMP/p44 peptide sequence. In certain embodiments, the additional N-terminal peptide sequence comprises an epitope of an *Anaplasma* surface antigen. Other *Anaplasma* antigens include, but are not limited to MSP5, HSP60, Asp14 (Kahlon et al., Infect Immun., Vol. 81(1): 65-79, 2013), and the antigens described in Zhi et al., J. Clin. Microbiol., Vol. 35(10): 2606-2611, 1997. Polypeptides or peptides derived from other microorganisms can also be used, including *Ehrlichia* antigens and *Borrelia* antigens. Protein and peptide sequences corresponding to *Ehrlichia* antigens have been described. See, e.g., U.S. application Ser. No. 14/052, 296, U.S. Pat. Nos. 6,306,402, 6,355,777, 7,204,992, 7,407, 770, 8,828,675, and WO2006/138509, the contents of each of which are incorporated herein by reference in their entireties. Protein and peptide sequences corresponding to *Borrelia* antigens have been described. See, e.g., U.S. Pat. Nos. 6,716, 574, 5,618,533, 5,643,733, 5,643,751, 5,932,220, 6,617,441, 7,887,815, 8,568,989, and 8,758,772, the contents of each of which are incorporated herein by reference in their entireties.

In certain embodiments, the additional N-terminal peptide sequence is a combination of sequences. For example, the additional N-terminal peptide sequence can comprise a native sequence, a non-native sequence, or any combination of such sequences (e.g., two or more native sequences, two or more non-native sequences, or one or more native sequences in combination with one or more non-native sequences).

In certain embodiments, peptides of the invention comprise a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and an additional C-terminal sequence (e.g., a C-terminal extension). The additional C-terminal peptide sequence can comprise 1, 2, 3, 4, 5, 6, 7, 8, 9, 10, 11, 12, 13, 14, 15, 20, 25, or more amino acids. In certain embodiments, the additional C-terminal sequence has a length of about 5 to about 10, about 10 to about 15, about 15 to about 20, about 20 to about 25, about 25 to about 30, about 30 to about 40, or about 40 to about 50 amino acids. The additional C-terminal peptide sequence can be a native MSP 2/p44 or OMP/p44 sequence. In certain embodiments, the C-terminal peptide sequence is a fragment of a naturally-occurring *Anaplasma* MSP 2/p44 or OMP/p44 sequence. The peptide sequence can be, e.g., from a conserved or non-conserved region of MSP 2/p44 or OMP/p44. The peptide sequence can comprise, e.g., an epitope, such as an immunodominant epitope or any other epitope recognizable by a host (e.g., human, dog, etc.) immune system.

In certain embodiments, the additional C-terminal peptide sequence can comprise or consist of another peptide having a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. For example, in certain embodiments, a peptide of the invention can be a multimer of sequences each having a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In other embodiments, the native sequence is a sequence (e.g., a MSP 2/p44 or OMP/p44 sequence) that is naturally adjacent to the C-terminal end of a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9.

In certain embodiments, the additional C-terminal peptide sequence is a non-native sequence. In some embodiments, the additional C-terminal peptide sequence comprises an epitope of an *Anaplasma* surface antigen other than MSP 2/p44 or OMP/p44. Polypeptides or peptides derived from other microorganisms can also be used. For instance, in some embodiments, the *Anaplasma* peptide sequence can further comprise an epitope from an *Ehrlichia* or *Borrelia* antigen.

In certain embodiments, the additional C-terminal peptide sequence is a combination of sequences. For example, the additional C-terminal peptide sequence can comprise a native, a non-native sequence, or any combination of such sequences (e.g., two or more native sequences, two or more non-native sequences, or one or more native sequences in combination with one or more non-native sequences).

In certain embodiments, peptides of the invention comprise a sequence defined by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and further comprise an additional N-terminal peptide sequence and an additional C-terminal peptide sequence. The additional N-terminal and C-terminal peptide sequences can be as described above. Peptides of the invention generally do not consist of a full-length MSP 2/p44 or OMP/p44 protein. However, in certain embodiments, peptides of the invention can comprise a full-length MSP 2/p44 or OMP/p44 protein. In other embodiments, peptides of the invention do not comprise a full-length MSP 2/p44 or OMP/p44 protein.

A peptide of the invention comprising an additional N-terminal and/or C-terminal peptide sequence can be designed for diagnosing *Anaplasma* infections (e.g. anaplasmosis) early after infection (e.g., within one to two weeks after the onset of infection). For example, in certain embodiments, the additional N-terminal and/or C-terminal peptide sequence comprises an antigen or epitope associated with early stages of *Anaplasma* infection.

In addition to the sequences described above, the additional N-terminal and C-terminal sequences can comprise or consist of a flexible sequence, designed to better present the peptides of the invention for detection in an immunoassay (e.g., ELISA assay, lateral flow immunoassay, agglutination assay, etc.). Such flexible sequences can be readily identified by persons skilled in the art.

In certain embodiments, peptides of the invention comprise or consist of 20 or more (e.g., 21, 22, 23, 24, 25, 26, 27, 28, 29, or more) amino acid residues. In certain embodiments, peptides of the invention comprise or consist of 30 or more (e.g., 31, 32, 33, 34, or more) amino acid residues. In certain embodiments, peptides of the invention comprise or consist of 35 or more (e.g., 36, 37, 38, 39, or more) amino acid residues. In certain embodiments, peptides of the invention comprise or consist of 40 or more (e.g., 41, 42, 43, 44, or more) amino acid residues. In certain embodiments, peptides of the invention comprise or consist of 45 or more (e.g., 46, 47, 48, 49, or more) amino acid residues. In certain embodiments, peptides of the invention comprise or consist of 50 or more (e.g., 51, 52, 53, 54, or more) amino acid residues. In certain embodiments, peptides of the invention comprise or consist of 55, 60, 65, 70, 75, 80, 85, 90, 95, 100, or more amino acid residues. In some embodiments, peptides of the invention comprise or consist of about 20 to about 75 amino acids, about 25 to about 65 amino acids, or about 30 to about 55 amino acids.

In certain embodiments, peptides of the invention comprise an epitope of a peptide sequence described herein. For example, in certain embodiments, peptides of the invention comprise an epitope of a sequence selected from the group consisting of SEQ ID NOs: 1-543.

In some embodiments, peptides of the invention comprise a fragment of a peptide sequence described herein. For example, in certain embodiments, peptides of the invention comprise a fragment of a sequence selected from the group consisting of SEQ ID NOs: 1-543. The fragment can be, e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids in length. The fragment can also be at least 45, 46, 47, 48, 49, 50, 51, 52, 53, 54, 55, 56, 57, 58, 59, 60, 61, 62, 63, 64, 65, or 66 amino acids long. In some embodiments, the fragment is no longer than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 amino acids long. The fragment can be contiguous or can include one or more deletions (e.g., a deletion of 1, 2, 3, 4, 5, 6, 7, 8, 9, 10, or more amino acid residues). For instance, in one embodiment, peptides of the invention comprise a fragment of SEQ ID NO: 3. Such fragments may comprise at least 10, 15, 20, 25, 30, or 35 contiguous amino acids from SEQ ID NO: 3. In some embodiments, the fragments comprise amino acids 1 to 35 of SEQ ID NO: 3. Thus, in one embodiment, a peptide of the invention comprises or consists of a sequence of E-T-K-V-$X_5$-Y-$X_7$-Y-L-K-$X_{11}$-G-R-T-V-K-L-$X_{18}$-S-H-$X_{21}$-F-D-W-$X_{25}$-T-P-$X_{28}$-P-K-$X_{31}$-G-F-K-D (SEQ ID NO: 543), wherein $X_5$ is an amino acid selected from the group consisting of V or A, $X_7$ is an amino acid selected from the group consisting of G, I or H, $X_{11}$ is an amino acid selected from the group consisting of E, N, or Q, $X_{18}$ is an amino acid selected from the group consisting of D or N, $X_{21}$ is an amino acid selected from the group consisting of R, D, or N, $X_{25}$ is an amino acid selected from the group consisting of Q, D, or E, $X_{28}$ is an amino acid selected from the group consisting of E or N, and $X_{31}$ is an amino acid selected from the group consisting of L or V.

Peptides of the invention that comprise a fragment of a peptide sequence described herein can further comprise an additional N-terminal peptide sequence, an additional C-terminal peptide sequence, or a combination thereof. The additional N-terminal and C-terminal peptide sequences can be as described above.

Peptides of the invention comprising an additional N-terminal or C-terminal peptide sequence can further comprise a linker connecting the peptide (e.g., a peptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, or a fragment thereof) with the additional N-terminal or C-terminal peptide sequence. The linker can be, e.g., a peptide spacer. Such spacer can consist of, for example, between about one and five (e.g., about three) amino acid residues, preferably uncharged amino acids, e.g., aliphatic residues such as glycine or alanine In one embodiment, the spacer is a triplet glycine spacer. In another embodiment, the spacer is a triplet alanine spacer. In another embodiment, the spacer consists of five glycine amino acids. In yet another embodiment, the spacer comprises both glycine and alanine residues. Alternatively, the linker can be a chemical (i.e., non-peptide) linker.

In certain embodiments, peptides of the invention are produced by synthetic chemistry (i.e., a "synthetic peptide"). In other embodiments, peptides of the invention are produced biologically (i.e., by cellular machinery, such as a ribosome, in cell expression systems or in vitro translation systems). In certain embodiments, peptides of the invention are isolated. As used herein, an "isolated" peptide is a peptide that has been produced either synthetically or biologically and then purified, at least partially, from the chemicals and/or cellular machinery used to produce the peptide. In certain embodiments, an isolated peptide of the invention is substantially purified. The term "substantially purified," as used herein, refers to a molecule, such as a peptide, that is substantially free of cellular material (proteins, lipids, carbohydrates, nucleic acids, etc.), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest. An isolated peptide of the invention can be in water, a buffer, or in a dry form awaiting reconstitution, e.g., as part of a kit. An isolated peptide of the present invention can be in the form of a pharmaceutically acceptable salt. Suitable acids and bases that are capable of forming salts with the peptides of the present invention are well known to those of skill in the art, and include inorganic and organic acids and bases.

In certain embodiments, peptides of the invention are affinity purified. For example, in certain embodiments, the peptides of the invention are purified by means of their ability to bind to anti-*Anaplasma* antibodies (e.g., antibodies to MSP 2/p44 or OMP/p44 proteins and, optionally, other *Anaplasma* antigens) by contacting such antibodies with the peptides of the invention such that peptide-antibody complexes are able to form, washing the peptide-antibody complexes to remove impurities, and then eluting the peptides from the antibodies. The antibodies can be, e.g., attached to a solid support. Methods of affinity purification are well-known and routine to those skilled in the art.

In certain embodiments, peptides of the invention are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

Peptides of the invention can be conjugated to a ligand, such as biotin (e.g., via a cysteine or lysine residue), a lipid molecule (e.g., via a cysteine residue), or a carrier protein (e.g., serum albumin, immunoglobulin Fc domain, keyhole limpet hemocyanin (KLH) via e.g., a cysteine or lysine residue). Attachment to ligands, such as biotin, can be useful for associating the peptide with ligand receptors, such as avidin, streptavidin, polymeric streptavidin (see, e.g., US 2010/0081125 and US 2010/0267166, both of which are herein incorporated by reference), or neutravidin. Avidin, streptavidin, polymeric streptavidin, or neutravidin, in turn, can be linked to a signaling moiety (e.g., an enzyme, such as horse radish peroxidase (HRP) or alkaline phosphatase (ALP) or β-galactosidase (β-GAL) or other moiety that can be visualized, such as a metallic nanomaterial such as nanoparticle, nanoplate, or nanoshell (e.g., colloidal gold), a fluorescent moiety, or a quantum dot) or a solid substrate (e.g., an IMMO-BILON™ or nitrocellulose membrane or POREX® membrane). Alternatively, the peptides of the invention can be fused or linked to a ligand receptor, such as avidin, streptavidin, polymeric streptavidin, or neutravidin, thereby facilitating the association of the peptides with the corresponding ligand, such as biotin and any moiety (e.g., signaling moiety) or solid substrate attached thereto. Examples of other ligand-receptor pairs are well-known in the art and can similarly be used.

Peptides of the invention can be fused to a fusion partner (e.g., a peptide or other moiety) that can be used to improve purification, to enhance expression of the peptide in a host cell, to aid in detection, to stabilize the peptide, etc. Examples of suitable compounds for fusion partners include carrier proteins (e.g., serum albumin, immunoglobulin Fc domain, KLH), enzymes (e.g., horse radish peroxidase (HRP), beta-galactosidase, glutathione-S-transferase, alkaline phosphatase), maltose-binding protein (MBP) or a histidine tag, etc. The fusion can be achieved by means of, e.g., a peptide bond. For example, peptides of the invention and fusion partners can be fusion proteins and can be directly fused in-frame or can comprise a peptide linker, as discussed above in the context of additional N-terminal and C-terminal peptide sequences. In certain embodiments, a population of peptides of the invention can be linked by a dendrimer, e.g., as in a MAPS structure.

In addition, peptides of the invention may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included. Peptides of the invention that consist of any of the sequences discussed herein may be modified by any of the discussed modifications. Such peptides still "consist of" the amino acids.

Modifications as set forth above are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins-Structure and Molecular Properties, 2nd ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

In certain embodiments, peptides of the invention are attached to or immobilized on a substrate, such as a solid or semi-solid support. The attachment can be covalent or non-covalent, and can be facilitated by a moiety associated with the peptide that enables covalent or non-covalent binding, such as a moiety that has a high affinity to a component attached to the carrier, support or surface. For example, the peptide can be associated with a ligand, such as biotin, and the component associated with the surface can be a corresponding ligand receptor, such as avidin. In some embodiments, the peptide can be associated with a fusion partner, e.g., bovine serum albumin (BSA), which facilitates the attachment of the peptide to a substrate. In other embodiments, the peptides of the invention are attached to or immobilized on a substrate via a metallic nanolayer. In one embodiment, the metallic nanolayer is comprised of cadmium, zinc, mercury, or a noble metal, such as gold, silver, copper, and platinum. The peptide or population of peptides can be attached to or immobilized on the substrate either prior to or after the addition of a sample containing antibody during an immunoassay.

In certain embodiments, the substrate is a bead or plurality of beads, such as a colloidal particle (e.g., a colloidal nanoparticle made from gold, silver, platinum, copper, cadmium, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, PVDF, or PMMA). Such particles can comprise a label (e.g., a colorimetric, chemiluminescent, quantum dot or fluorescent label) and can be useful for visualizing the location of the peptides during immunoassays. In certain embodiments, a terminal cysteine of a peptide of the invention is used to bind the peptide directly to a metallic nanomaterial or nanostructure.

The metallic nanomaterials or nanostructures used in some embodiments of the invention can be made from gold, silver, platinum, palladium, copper, cadmium, metal composites, or other soft metals. In some embodiments, the metallic nanomaterials or nanostructures, including the composite nanostructures, have a geometry selected from spherical nanoparticles, pyramidal nanoparticles, hexagonal nanoparticles, nanoshells, nanoplates, nanotubes, nanowires, and combinations thereof. Examples of metallic nanoshells include gold hollow spheres, gold-coated silica nanoshells, and silica-coated gold shells. Nanoplates have lateral dimensions (e.g. edge lengths) that are greater than their thickness. Nanoplates include nanodisks, nanopolygons, nanohexagons, nanocubes, nanorings, nanostars, and nanoprisms. In some embodiments, the metallic nanostructures have other shapes or irregular shapes. In certain embodiments, the size and shape of the metallic nanostructures are not uniform—i.e. the metallic nanostructures are a heterogeneous mixture of different shapes and sizes of nanostructures.

For spherical nanoparticles, suitable diameter ranges include from about 5 nm to about 200 nm, from about 10 nm to about 100 nm, and from about 20 nm to about 60 nm. For nanoplates, edge lengths may be from about 10 nm to about 800 nm, from about 20 nm to about 500 nm, from about to 50 nm to about 200 nm, from about 30 nm to about 100 nm, or from about 10 nm to about 300 nm. The thickness of the nanoplates can range from about 1 to about 100 nm, from about 5 nm to about 80 nm, from about 10 nm to about 50 nm, or from about 5 nm to about 20 nm.

In some embodiments, the nanoplates have an aspect ratio greater than 2. The aspect ratio is the ratio of the edge length to the thickness. Preferably, the nanoplates have an aspect ratio from about 2 to about 25, from about 3 to about 20, from about 5 to about 10, from about 2 to about 15, or from about 10 to about 30.

In certain embodiments, the substrate is a dot blot or a flow path in a lateral flow immunoassay device. For example, the peptides can be attached or immobilized on a porous membrane, such as a PVDF membrane (e.g., an IMMOBILON™ membrane), a nitrocellulose membrane, polyethylene membrane, nylon membrane, or a similar type of membrane.

In certain embodiments, the substrate is a flow path in an analytical or centrifugal rotor. In other embodiments, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene, for example, 0.2-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Accordingly, in another aspect, the invention provides devices. In certain embodiments, the devices are useful for performing an immunoassay. For example, in certain embodiments, the device is a lateral flow immunoassay device. An exemplary lateral flow immunoassay device comprising peptides of the invention is described in Example 2. In certain embodiments, the lateral flow immunoassay device comprises a population of peptides, wherein each peptide in the population comprises a sequence of SEQ ID NO: 3, SEQ ID NO: 4, SEQ ID NO: 6, SEQ ID NO: 7, or SEQ ID NO: 9. In some embodiments, the device is a slide comprised of a plurality of beads to which a peptide or population of peptides is attached. An example of such a device comprising peptides of the invention suitable for use, for example, in an indirect fluorescent antibody assay is described in Example 3. In other embodiments, the device is an analytical or centrifugal rotor. In other embodiments, the device is a dot blot, slot blot, or Western blot. In other embodiments, the device is a tube or a well, e.g., in a plate suitable for an ELISA assay. An exemplary device comprising peptides of the invention for use in an ELISA assay is described in Example 1. In still other embodiments, the device is an electrochemical sensor, an optical sensor, or an opto-electronic sensor.

In certain embodiments, the device comprises a peptide or population of peptides of the invention. In other embodiments, the device comprises a mixture of different peptides of the invention. For example, in certain embodiments, the device comprises two, three, four, or more different peptides of the invention. In certain embodiments, the peptide or each peptide in the population comprises a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 or a fragment thereof. In other embodiments, the peptide or each peptide in the population comprises a sequence of SEQ ID NO: 3, SEQ ID NO: 4, or a fragment thereof. In certain embodiments, the population of peptides are attached to or immobilized upon the device optionally through a metallic nanolayer. The devices may be used to detect the presence of antibodies to *Anaplasma* antigens from multiple species (e.g., *A. phagocytophilum*, *A. platys*, and *A. marginale*) in a sample simultaneously. In one embodiment, the device comprises a population of isolated peptides comprising three or more different peptides, wherein each peptide in the population comprises a sequence of SEQ ID NO: 3. In another embodiment, the device comprises a population of isolated peptides comprising three or more different peptides, wherein each peptide in the population comprises a sequence of SEQ ID NO: 4. In another embodiment, the device comprises a population of isolated peptides comprising three or more different peptides, wherein each peptide in the population comprises a sequence of SEQ ID NO: 1. In still another embodiment, the device comprises a population of isolated peptides comprising three or more different peptides, wherein each peptide in the population comprises a sequence of SEQ ID NO: 8. In other embodiments, the device comprises a population of isolated peptides comprising three or more different peptides, wherein each peptide in the population comprises a sequence of SEQ ID NO: 2, SEQ ID NO: 5, SEQ ID NO: 6, SEQ ID NO: 7, or SEQ ID NO: 9.

In another aspect, the invention provides compositions comprising one or more peptides of the invention. For example, in certain embodiments, the invention provides a composition comprising a peptide comprising a sequence of SEQ ID NO: 3, or populations thereof. In certain embodiments, the composition comprises a population of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 3). Thus, the present invention provides a population of isolated peptides comprising three or more different peptides, wherein each peptide in the population comprises a sequence of SEQ ID NO: 3. In certain embodiments, the peptides in the population or mixture comprise an N-terminal and/or C-terminal addition, and/or are modified (e.g., by association with one or more further moieties), as described herein. In certain embodiments, the peptides comprise the same N-terminal and/or C-terminal additions. In other embodiments, the peptides comprise different N-terminal and/or C-terminal additions.

In some embodiments, the invention provides a composition comprising a peptide comprising a sequence of SEQ ID NO: 4, or populations thereof. In certain embodiments, the composition comprises a population of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 4). Thus, the present invention provides a population of isolated peptides comprising three or more different peptides, wherein each peptide in the population comprises a sequence of SEQ ID NO: 4. In certain embodiments, the peptides in the population or mixture comprise an N-terminal and/or C-terminal addition, and/or are modified (e.g., by association with one or more further moieties), as described herein. In certain embodiments, the peptides comprise the same N-terminal and/or C-terminal additions. In other embodiments, the peptides comprise different N-terminal and/or C-terminal additions.

In still other embodiments, the invention provides a composition comprising a peptide comprising a sequence of SEQ ID NO: 1, SEQ ID NO: 2, SEQ ID NO: 5, SEQ ID NO: 6, SEQ ID NO: 7, SEQ ID NO: 8, SEQ ID NO: 9, SEQ ID NO: 543, or populations thereof. In certain embodiments, the composition comprises a population of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 1, SEQ ID NO: 2, SEQ ID NO: 5, SEQ ID NO: 7, SEQ ID NO: 8, SEQ ID NO: 9, SEQ ID NO: 543). Thus, the invention provides a population of isolated peptides comprising three or more different peptides, wherein each peptide in the population comprises a sequence of SEQ ID NO: 1. In another embodiment, the invention provides a population of isolated peptides comprising three or more different peptides, wherein each peptide in the population comprises a sequence of SEQ ID NO: 2. In other embodiments, the invention provides a population of isolated peptides comprising three or more different peptides, wherein each peptide in the population comprises a sequence of SEQ ID NO: 5, SEQ ID NO: 7, SEQ ID NO: 8, SEQ ID NO: 9, or SEQ ID NO: 543. The peptides in the population or mixture may comprise an N-terminal and/or C-terminal addition, and/or be modified (e.g., by association with one or more further moieties), as described herein.

In some embodiments, the composition comprises a population of isolated peptides, said population comprising three or more different peptides, wherein each peptide in the population comprises a sequence, or a fragment thereof, of SEQ ID NO: 1, 2, 3, 4, 5, 6, 7, 8, or 9.

In some embodiments, the composition comprises at least two different populations of peptides described herein. In certain embodiments, at least one of the peptide populations is defined by SEQ ID NO: 3 (i.e., comprising three or more different peptides, wherein each peptide in the population comprises a sequence, or a fragment thereof, of SEQ ID NO: 3).

In certain embodiments, the composition further comprises a second population of isolated peptides. In some embodiments, the second peptide population is defined by SEQ ID NO: 7. In some other embodiments, each peptide in the second peptide population comprises the sequence, or a fragment thereof, of SEQ ID NO: 6.

In some embodiments, the composition further comprises a third population of isolated peptides that is different from the first and second peptide populations. In certain embodiments, each peptide in the third peptide population comprises the sequence, or a fragment thereof, of SEQ ID NO: 6.

In a particular embodiment, the composition comprises three different populations of peptides, a first peptide populations which is defined by SEQ ID NO: 3, a second peptide population which is defined by SEQ ID NO: 7, and a third peptide population in which each peptide comprises the sequence, or a fragment thereof, of SEQ ID NO: 6.

In certain embodiments, the compositions comprise one or more peptides (or one or more populations of peptides) of the invention and one or more additional peptides, such as an *Anaplasma* peptide or antigen, a peptide or antigen from one or more *Ehrlichia* species, and/or a peptide or antigen from one or more *Borrelia* species. The *Anaplasma* peptide or antigen can be any *Anaplasma* surface peptide or antigen, or any peptide or antigen described herein. For instance, in certain embodiments, the compositions comprise a mixture of peptides, wherein each peptide has a sequence of SEQ ID NO: 3, SEQ ID NO: 6, or SEQ ID NO: 7. In other embodiments, the compositions comprise a mixture of peptides, wherein each peptide has a sequence of SEQ ID NO: 3, SEQ ID NO: 4, or SEQ ID NO: 6.

Suitable *Ehrlichia* peptides that can be mixed with the *Anaplasma* peptides of the invention include any *Ehrlichia* surface peptide or antigen including, but not limited to, OMP-1, p38, p43, p120, p140, p153, p156, p200, gp19, gp36, gp47, gp200, or HGE-3 protein, or any fragment or epitope thereof. Other suitable *Ehrlichia* peptides include peptides described in U.S. application Ser. No. 14/052,296 and U.S. Pat. No. 8,828,675, the contents of each of which are hereby incorporated by reference in their entireties. Suitable *Borrelia* peptides that can be mixed with the *Anaplasma* peptides of the invention include any *Borrelia* surface peptide or antigen including, but not limited to, OspA, OspB, DbpA, flagella-associated proteins FlaA (p37) and FlaB (p41), OspC (25 kd), BBK32, BmpA (p39), p21, p39, p66 or p83 protein, or any fragment or epitope thereof. Other suitable *Borrelia* peptides include peptides described in U.S. Pat. Nos. 8,568,989 and 8,758,772, the contents of each of which are hereby incorporated by reference in their entireties. The combination may comprise a cocktail (a simple mixture) of individual peptides or polypeptides, it may be in the form of a fusion peptide or polypeptide (e.g., a multimeric peptide), or the peptides may be linked by a dendrimer (e.g., as in a MAPS structure) optionally through a linking residue (e.g. lysine or cysteine residue). For instance, in certain embodiments, a composition comprises one or more peptides of the invention (e.g., a peptide having a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 543) and one or more antigenic *Ehrlichia* peptides and/or one or more antigenic *Borrelia* peptides.

When a composition comprises multiple peptides or peptide populations, the ratio among the various peptides or peptide populations can be varied in order to tailor the composition's performance, e.g., in terms of sensitivity and selectivity. For example, in a composition comprising two peptide populations, the molar ratio of the two peptide populations can vary anywhere between 20:1 to 1:20, e.g., 20:1, 10:1, 5:1, 3:1, 2:1, 1:1, 1:2, 1:3, 1:5, 1:10, or 1:20. Or, the percentage of weight ratio can vary between 95:5 to 5:95, e.g., 95:5, 90:10, 80:20, 70:30, 60:40, 50:50, 40:60, 30:70, 20:80, 10:90, or 5:95. In a composition comprising three or more peptide populations, the percentage of moles or weight of each peptide population can vary from 1% to 98% of the total moles or weight of all three peptide populations, e.g., 1%, 2%, 5%, 10%, 15%, 20%, 25%, 30%, 33%, 40%, 50%, 60%, 70%, 80%, 90%, 95%, 98%, etc. In a certain embodiment, the composition comprises three peptide populations, APL-ID1 (defined by SEQ ID NO: 3), APL-ID5.1 (each peptide comprising SEQ ID NO: 6), and APL-ID6 (defined by SEQ ID NO: 7) in a weight ratio of 50:25:25. In another embodiment, the composition comprises three peptide populations, APL-ID1 (defined by SEQ ID NO: 3), APL-ID5.1 (each peptide comprising SEQ ID NO: 6), and APL-ID6 (defined by SEQ ID NO: 7), wherein each peptide population constitutes a third of the composition by weight.

A peptide of the invention may be fused at its N-terminus or C-terminus to another suitable peptide. Two or more copies of a peptide of the invention may be joined to one another, alone or in combination with one or more additional peptides. Combinations of fused and unfused peptides or polypeptides can be used. In one embodiment, the additional peptide(s) contain B-cell and/or T-cell epitopes from an *Anaplasma* peptide or antigen, a peptide or antigen from an infectious *Anaplasma* species, or a peptide or antigen from a causative agent of anaplasmosis.

In another aspect, the invention provides nucleic acids comprising a sequence encoding a peptide of the invention. Nucleic acids of the invention contain less than an entire microbial genome and can be single- or double-stranded. A nucleic acid can be RNA, DNA, cDNA, genomic DNA, chemically synthesized RNA or DNA or combinations thereof. The nucleic acids can be purified free of other components, such as proteins, lipids and other polynucleotides. For example, the nucleic acids can be 50%, 75%, 90%, 95%, 96%, 97%, 98%, 99%, or 100% purified. The nucleic acids of the invention encode the peptides described herein. In certain embodiments, the nucleic acids encode a peptide having the sequence of SEQ ID NOs: 1-543, or combinations thereof. Nucleic acids of the invention can comprise other nucleotide sequences, such as sequences coding for linkers, signal sequences, TMR stop transfer sequences, transmembrane domains, or ligands useful in protein purification such as glutathione-S-transferase, histidine tag, MBP tag and staphylococcal protein A.

Nucleic acids of the invention can be isolated. An "isolated" nucleic acid is one that is not immediately contiguous with one or both of the 5' and 3' flanking genomic sequences with which it is naturally associated. An isolated nucleic acid can be, e.g., a recombinant DNA molecule of any length, provided that the nucleic acid sequences naturally found immediately flanking the recombinant DNA molecule in a naturally-occurring genome is removed or absent. Isolated nucleic acids also include non-naturally occurring nucleic acid molecules. Nucleic acids of the invention can also comprise fragments that encode immunogenic peptides. Nucleic acids of the invention can encode full-length polypeptides, peptide fragments, and variant or fusion peptides.

Nucleic acids of the invention can be isolated, at least in part, from nucleic acid sequences present in, for example, a biological sample, such as blood, serum, saliva, or tissue from an infected individual. Nucleic acids can also be synthesized in the laboratory, for example, using an automatic synthesizer. An amplification method such as PCR can be used to amplify nucleic acids, at least in part, from either genomic DNA or cDNA encoding the polypeptides.

Nucleic acids of the invention can comprise coding sequences for naturally occurring polypeptides or can encode altered sequences that do not occur in nature. If desired, nucleic acids can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A nucleic acid of the invention is operably linked when it is positioned adjacent to or close to one or more expression control elements, which direct transcription and/or translation of the polynucleotide.

Thus, for example, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably linked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al., Molecular Cloning, A Laboratory Manual, current edition, Cold Spring Harbor Laboratory, New York; Miller et al., Genetic Engineering, 8:277-298 (Plenum Press, current edition), Wu et al., Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausubel et al., Eds.,) John Wiley & Sons, NY (current edition), and references cited therein.

Accordingly, the invention also provides vectors comprising nucleic acids of the invention, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

Suitable host cells or cell lines for expression of the recombinant nucleic acids or vectors of the invention include bacterial cells. For example, various strains of *E. coli* (e.g., HB101, MC1061) are well-known as host cells in the field of biotechnology. Various strains of *B. subtilis, Pseudomonas, Streptomyces*, and other bacilli and the like can also be employed to express the nucleic acids or vectors of the invention. Alternatively, a peptide of the invention can be expressed in yeast, insect, mammalian, or other cell types, using conventional procedures. Cell-free in vitro synthesis and/or enzyme-mediated synthetic machineries may also be used.

The present invention also provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g., a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like, affinity chromatography, such as with inorganic ligands or monoclonal antibodies, size exclusion chromatography, immobilized metal chelate chromatography, gel electrophoresis, and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g., SDS-PAGE), capillary electrophoresis, column chromatography (e.g., high performance liquid chromatography (HPLC)), amino-terminal amino acid analysis, and quantitative amino acid analysis.

Methods

In another aspect, the invention provides methods of detecting in a sample an antibody to an epitope of an *Anaplasma* antigen. In one embodiment, the method comprises contacting a sample with a peptide of the invention, and detecting formation of an antibody-peptide complex comprising said peptide, wherein formation of said complex is indicative of the presence of an antibody to an epitope of an *Anaplasma* antigen in said sample. In some embodiments, the *Anaplasma* antigen is from an infectious *Anaplasma* species, such as *Anaplasma phagocytophilum, Anaplasma platys*, or *Anaplasma marginale*. Other species of *Anaplasma* which have been implicated in anaplasmosis can also be detected using the methods of the invention, provided they induce antibodies which can react specifically with a peptide of the invention. Thus, it is to be understood that the term "pathogenic *Anaplasma*," as used herein, refers to any such *Anaplasma* species that causes anaplasmosis in a human or an animal. In particular embodiments, the methods provide detection of antibodies to *Anaplasma* antigens from multiple species in a sample simultaneously.

In certain embodiments, the method of detecting in a sample an antibody to an epitope of an *Anaplasma* antigen comprises contacting the sample with a population of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention, and detecting formation of an antibody-peptide complex comprising said one or more peptides in the population, wherein formation of said complex is indicative of an antibody to an epitope of an *Anaplasma* antigen being present in said sample. For instance, in one particular embodiment, the method comprises contacting the sample with a population of two or more different isolated peptides, wherein each isolated peptide comprises a sequence of SEQ ID NO: 3. In another particular embodiment, the method comprises contacting the sample with a population of two or more different isolated peptides, wherein each isolated peptide comprises a sequence of SEQ ID NO: 4. In still another embodiment, the method comprises contacting the sample with a population of two or more different isolated peptides, wherein each isolated peptide comprises a sequence of SEQ ID NO: 1. In some embodiments, the method comprises contacting the sample with a population of two or more different isolated peptides, wherein each isolated peptide comprises a sequence of SEQ ID NO: 2, SEQ ID NO: 5, SEQ ID NO: 6, SEQ ID NO: 7, SEQ ID NO: 8, SEQ ID NO: 9, or SEQ ID NO: 543. In certain embodiments, the method comprises contacting the sample with a mixture of one or more peptides of the invention and one or more other peptides (e.g., an *Ehrlichia* peptide, or antigenic fragment or epitope thereof and/or a *Borrelia* peptide or antigenic fragment or epitope thereof).

In certain embodiments, the peptide or each peptide in the population is an isolated (e.g., synthetic and/or purified) peptide. In some embodiments, the peptide or population of peptides is attached to or immobilized upon a solid support. In such embodiments, the solid support is a bead or plurality of beads (e.g., a metallic nanomaterial such as nanoparticle, nanoplate, or nanoshell, a nanoparticle, a latex bead, etc.), a flow path in a lateral flow immunoassay device (e.g., a porous membrane), a flow path in an analytical or centrifugal rotor, a blot (Western blot, dot blot, or slot blot), a tube or a well (e.g., in a plate suitable for an ELISA assay), or a sensor (e.g., an electrochemical, optical, or opto-electronic sensor). In some embodiments, the peptide or population of peptides is attached to or immobilized upon a solid support through a metallic nanolayer that, in some embodiments, may be comprised of cadmium, zinc, mercury, or a noble metal (e.g., gold, silver, copper, and platinum). In some embodiments, the peptides or populations of peptides of the invention are immobilized on a composite nanolayer (for example comprising silver and gold) or gold-coated silver nanolayers.

There are a number of different conventional assays for detecting formation of an antibody-peptide complex comprising a peptide of the invention. For example, in some embodiments, the detecting step comprises performing an ELISA or immunofluorescence assay. In other embodiments, the detecting step comprises performing a lateral flow immunoassay. In other embodiments, the detecting step comprises performing an agglutination assay (e.g., a hemagglutination or particle/bead agglutination assay). In still other embodiments, the detecting step comprises spinning the sample in an analytical or centrifugal rotor. In some embodiments, the detecting step comprises performing a Western blot, slot blot, or dot blot. In certain embodiments, the detecting step comprises performing a wavelength shift assay. Such wavelength shift assays may entail measuring or determining a change in the surface plasmon resonance or localized surface plasmon resonance wavelength resulting from binding of antibodies to peptides attached to metallic nanolayers or metallic nanoparticles/nanoshells/nanoplates. In other embodiments, the detecting step comprises performing an Indirect Fluorescent Antibody test. In some embodiments, the Indirect Fluorescent Antibody test comprises reacting samples suspected of containing antibodies against *Anaplasma* antigens with beads (e.g. latex beads) coated with the peptides of the invention, which are further immobilized on a glass slide, and subsequently reacting the slide with fluorescently labeled anti-dog IgG or IgM antibodies to detect bound anti-*Anaplasma* antibodies. An example of an Indirect Fluorescent Antibody test is described in Example 3. In still other embodiments, the detecting step comprises analyzing the sample with an electrochemical, optical, or opto-electronic sensor. These different assays are described herein and/or are well-known to those skilled in the art.

In one embodiment, the method involves detecting the presence of naturally occurring antibodies against one or more *Anaplasma* antigens (e.g., the antigen of a pathogenic *Anaplasma*, such as *A. phagocytophilum, A. platys*, or *A. marginale*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

Suitable immunoassay methods typically include: receiving or obtaining (e.g., from a patient) a sample of body fluid or tissue likely to contain antibodies; contacting (e.g., incubating or reacting) a sample to be assayed with a peptide or population of peptides of the invention, under conditions effective for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected with an infectious *Anaplasma* species. A peptide, including a modified form thereof, which "binds specifically" to (e.g., "is specific for" or binds "preferentially" to) an antibody against an *Anaplasma* antigen interacts with the antibody, or forms or undergoes a physical association with it, in an amount and for a sufficient time to allow detection of the antibody. By "specifically" or "preferentially," it is meant that the peptide has a higher affinity (e.g., a higher degree of selectivity) for such an antibody than for other antibodies in a sample. For example, the peptide can have an affinity for the antibody of at least about 1.5-fold, 2-fold, 2.5-fold, 3-fold, or higher than for other antibodies in the sample. Such affinity or degree of specificity can be determined by a variety of routine procedures, including, e.g., competitive binding studies. In an ELISA assay, a positive response is defined as a value 2 or 3 standard deviations greater than the mean value of a group of healthy controls. In some embodiments, a second tier assay is required to provide an unequivocal serodiagnosis of anaplasmosis.

Phrases such as "sample containing an antibody" or "detecting an antibody in a sample" are not meant to exclude samples or determinations (e.g., detection attempts) where no antibody is contained or detected. In a general sense, this invention involves assays to determine whether an antibody produced in response to infection with an infectious *Anaplasma* species is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc).

The methods of the invention comprise receiving or obtaining a sample of body fluid or tissue likely to contain antibodies from a subject. The antibodies can be, e.g., of IgG, IgE, IgD, IgM, or IgA type. Generally, IgM and/or IgA antibodies are detected, e.g., for detection at early stages of infection. IgG antibodies can be detected when some of the additional peptides discussed above are used in the method (e.g., peptides for the detection of flagellum proteins). The sample is preferably easy to obtain and may be whole blood, plasma, or serum derived from a venous blood sample or even from a finger prick. Tissue from other body parts or other bodily fluids, such as cerebro-spinal fluid (CSF), saliva, gastric secretions, mucus, urine, etc., are known to contain antibodies and may be used as a source of the sample. The sample may also be a tissue extract or a cell lysate.

Once the peptide or population of peptides of the invention and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

Figure 2:
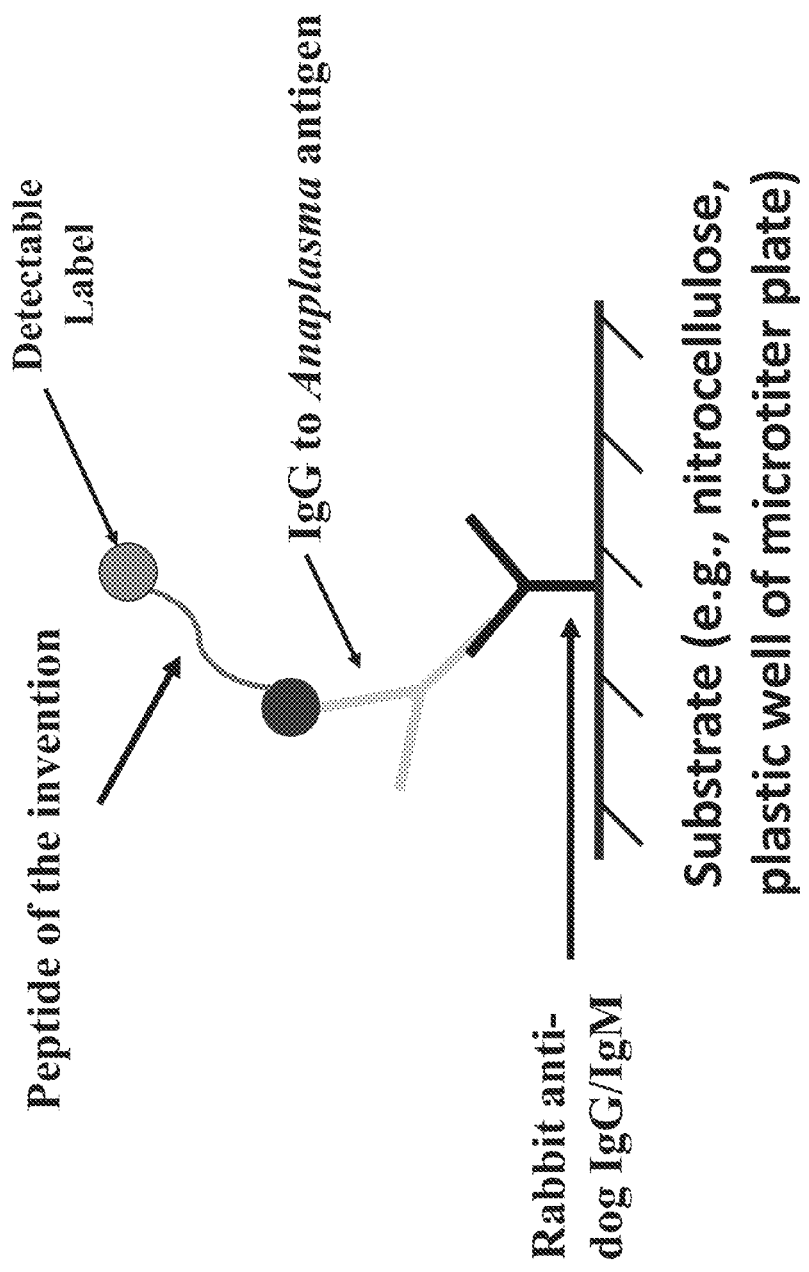
FIG. 2 is a diagram of one type of indirect sandwich assay which can be used to detect antibodies to *Anaplasma* antigens. In this embodiment, anti-human IgG/IgM, anti-dog IgG/IgM, or anti-cat IgG/IgM antibodies are immobilized to a suitable substrate (e.g., nitrocellulose membrane, well of an ELISA plate) at a test site. Antibodies to *Anaplasma* antigens in a test sample are bound by the immobilized antibodies. Test sample antibodies to appropriate *Anaplasma* antigens will then bind to peptides of the invention that are conjugated to a detectable label (e.g., metallic nanomaterial such as nanoparticle, nanoplate, or nanoshell (e.g., colloidal gold), HRP, ALP, β-GAL, fluorophore, colored latex particle, or quantum dot).
Figure 3:
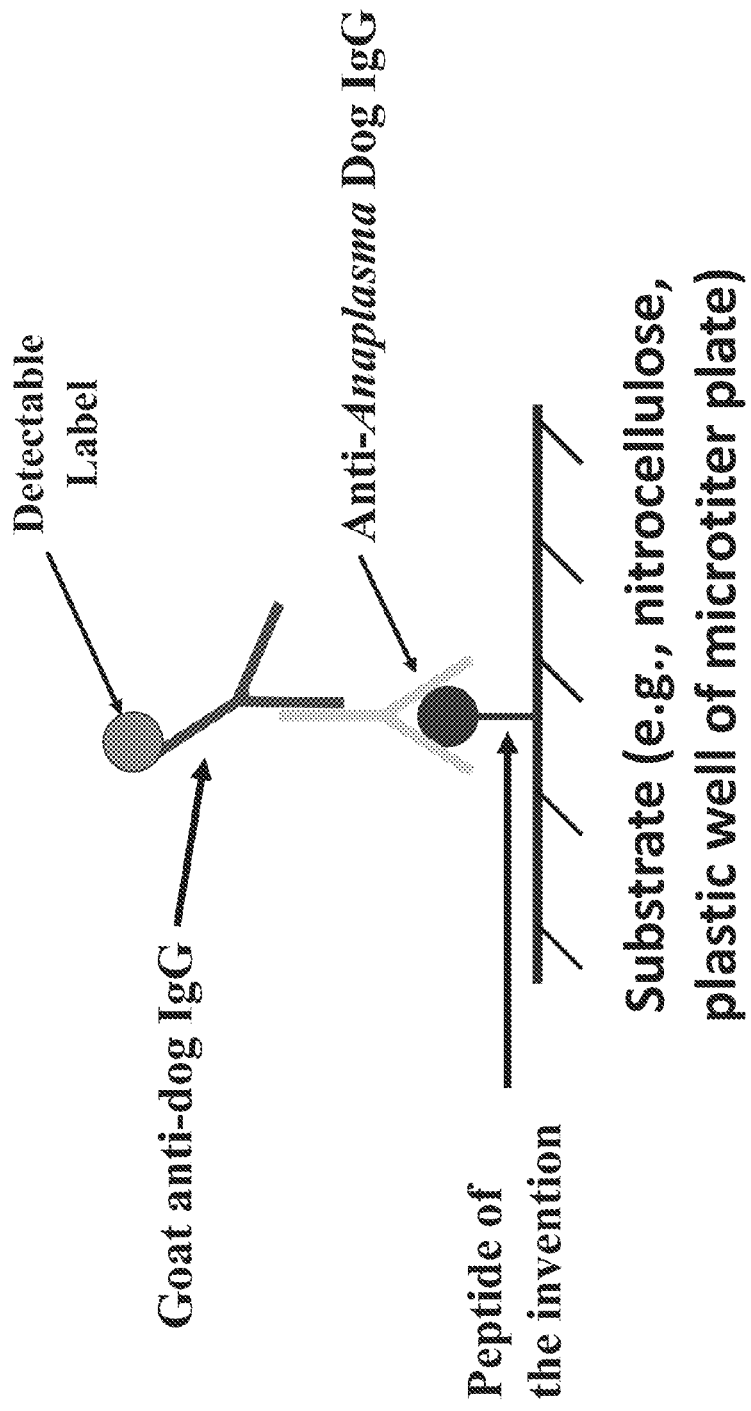
FIG. 3 is a diagram of another type of indirect sandwich assay which can be used to detect antibodies to *Anaplasma* antigens. In this embodiment, peptides of the invention can be immobilized to a substrate (e.g., nitrocellulose membrane, well of an ELISA plate) to capture anti-*Anaplasma* antibodies in a test sample. Anti-human IgG/IgM, anti-dog IgG/IgM, or anti-cat IgG/IgM antibodies conjugated to a detectable label (e.g., metallic nanomaterial such as nanoparticle, nanoplate, or nanoshell (e.g., colloidal gold), HRP, ALP, β-GAL, fluorophore, colored latex particle, quantum dot) can be used to detect the presence of the antibodies bound to the immobilized peptides at the test site.
Figure 4:
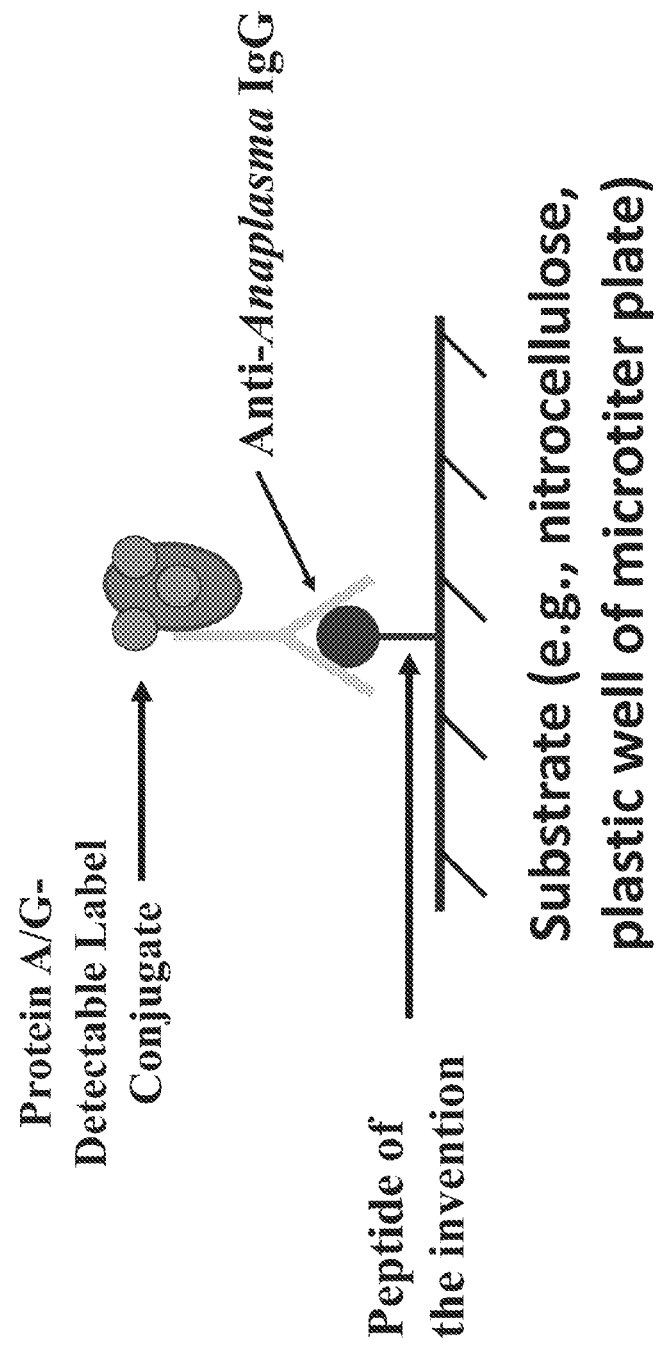
FIG. 4 is a diagram of an immunoassay device which can be used to detect antibodies to *Anaplasma* antigens. In this embodiment of an immunoassay device, peptides of the invention are immobilized to a suitable substrate (e.g., nitrocellulose membrane, well of an ELISA plate) at a test site. Anti-*Anaplasma* antibodies in a test sample are bound by the immobilized peptides of the invention. Protein A, Protein G, or a Protein A/G fusion protein conjugated to a detectable label (e.g., metallic nanomaterial such as nanoparticle, nanoplate, or nanoshell (e.g., colloidal gold), HRP, ALP, β-GAL, fluorophore, colored latex particle, quantum dot) is added to the system and binds to the Fc portion of the captured anti-*Anaplasma* antibody, thereby producing a positive signal. In this embodiment, the device can further comprise a control site at which binding partners that recognize the detectable label-conjugated protein A, detectable label-conjugated protein G, and/or detectable label-conjugated protein A/G fusion are immobilized. Such binding partners may include, but are not limited to, anti-protein A, anti-protein G, mouse IgG, and/or other similar IgG molecules.

In certain embodiments of the invention, the assay comprises: immobilizing the antibody(s) in the sample; adding a peptide or population of peptides of the invention; and detecting the degree of antibody bound to the peptide or peptides, e.g., by the peptide being labeled or by adding a labeled substance, such as a labeled binding partner (e.g., streptavidin-HRP or streptavidin-colloidal gold complex) or a labeled antibody which specifically recognizes the peptide or peptides. See, e.g., FIG. 2. In other embodiments, the assay comprises: immobilizing a peptide or population of peptides of the invention; adding the sample containing antibodies; and detecting the amount of antibody bound to the peptide or peptides, e.g., by adding another peptide or population of peptides of the invention conjugated, directly or indirectly, to a label (e.g., metallic nanomaterial such as nanoparticle, nanoplate, or nanoshell, fluorescent label, enzyme (e.g., horseradish peroxidase or alkaline phosphatase)) or by adding a labeled substance, such as a binding partner or a labeled antibody which specifically recognizes the sample antibodies (e.g., anti-human IgG antibodies, anti-human IgM antibodies, anti-dog IgG antibodies, anti-dog IgM antibodies, anti-cat IgG antibodies, anti-cat IgM antibodies, protein A, protein G, protein A/G fusion proteins, protein L, or combinations thereof, etc.). See, e.g., FIGS. 1, 3, and 4.

In other embodiments, the assay comprises: immobilizing a peptide or population of peptides of the invention; adding the sample containing antibodies; and detecting the amount of antibody bound to the peptide or peptides, e.g., by adding a first binding partner which specifically recognizes the sample antibodies (e.g., anti-human IgG antibodies, anti-human IgM antibodies, anti-dog IgG antibodies, anti-dog IgM antibodies, anti-cat IgG antibodies, anti-cat IgM antibodies, protein A, protein G, protein A/G fusion proteins, protein L, etc.), and further adding a second binding partner (e.g., protein A, protein G, protein A/G fusion proteins, protein L, etc.), wherein the second binding partner is labeled and recognizes said first binding partner. In still other embodiments, the assay comprises: reacting the peptide or population of peptides and the sample containing antibodies without any of the reactants being immobilized, and then detecting the amount of complexes of antibody and peptide or peptides, e.g., by the peptide being labeled or by adding a labeled substance, such as a labeled binding partner (e.g., streptavidin-HRP or streptavidin-colloidal gold complex) or a labeled antibody which specifically recognizes the peptide.

Immobilization of a peptide or population of peptides of the invention can be either covalent or non-covalent, and the non-covalent immobilization can be non-specific (e.g., non-specific binding to a polystyrene surface in, e.g., a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin, neutravidin, or an analogue thereof. An alternative is a situation in which the moiety is a histidine tag (e.g. six consecutive histidine amino acids) and the carrier comprises a Nitrilotriacetic Acid (NTA) derivative charged with Ni++ or Co++ ions. In certain embodiments, the moiety is a fusion partner, e.g., BSA. In exemplary embodiments, peptides of the invention may be conjugated to BSA via N-terminal and/or C-terminal residues of the peptides. In one embodiment, one, two, three, four, five, 10, 15, 20, 25, 30 or more peptides of the invention may be substituted into, e.g., conjugated with BSA. As would be understood by one skilled in the art, substitution levels may impact the sensitivity of the assay. Lower concentrations of highly substituted BSA are needed to achieve sensitivity offered by high concentrations of BSA-peptide containing fewer molecules of peptide. In certain other embodiments, the fusion partner may be MAPS. In certain exemplary embodiments, MAPS may consist of 4, 8, or more asymmetric branches.

Suitable carriers, supports, and surfaces include, but are not limited to, metallic nanolayers, beads (e.g., magnetic beads, colloidal particles or metallic nanomaterials, such as metallic nanoparticles, nanoplates, or nanoshells, such as colloidal gold, or particles or nanoparticles comprising silica, latex, polystyrene, polycarbonate, or PDVF), latex or co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In certain embodiments, a peptide or population of peptides of the invention is immobilized on a solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices (e.g., lateral flow immunoassay devices), dipsticks, and immunocapillary or immunochromatographic immunoassay devices.

In embodiments of the invention, the solid or semi-solid surface or carrier is the floor or wall in a microtiter well, a filter surface or membrane (e.g., a nitrocellulose membrane or a PVDF (polyvinylidene fluoride) membrane, such as an IMMOBILON™ membrane), polyethylene membrane such as POREX® membrane, a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, the peptide is provided with (e.g. conjugated to) a suitable label which enables detection. Conventional labels may be used which are capable, alone or in concert with other compositions or compounds, of providing a detectable signal. Suitable labels include, but are not limited to, enzymes (e.g., HRP, beta-galactosidase, alkaline phosphatase, etc.), fluorescent labels, quantum dots, radioactive labels, colored latex particles, and metal-conjugated labels (e.g., metallic nanolayers, metallic nanomaterial-conjugated labels). Suitable metallic nanomaterials include, but are not limited to, metallic nanoparticles, metallic nanoplates, and metallic nanoshells. Suitable metallic nanomaterial labels include, but are not limited to, gold particles or nanoplates, silver particles or nanoplates, copper particles or nanoplates, platinum particles or nanoplates, palladium particles or nanoplates, cadmium particles or nanoplates, composite particles or nanoplates, gold hollow spheres, gold-coated silica nanoshells, and silica-coated gold shells. Metallic nanolayers suitable for detectable layers include nanolayers comprised of cadmium, zinc, mercury, and noble metals, such as gold, silver, copper, and platinum. In some embodiments, the metallic nanolayers comprise composite gold-silver or silver nanolayers coated with gold.

Suitable detection methods include, e.g., detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, or the like. In one embodiment, a radioactive element (e.g., a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L or combinations thereof) which binds to the first antibody. This secondary antibody or other binding agent can be labeled, e.g., with a radioactive, enzymatic, fluorescent, quantum dot, luminescent, metallic nanomaterial such as metallic nanoparticle, metallic nanoplate, or metallic nanoshell (e.g. colloidal gold), or other detectable label, such as an avidin/biotin system. In another embodiment, the binding partner is a peptide or population of peptides of the invention, which can be conjugated directly or indirectly (e.g. via biotin/avidin interaction) to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In some embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

A particularly useful assay format is a lateral flow immunoassay format. Antibodies to human or animal (e.g., dog, mouse, deer, etc.) immunoglobulins, or staph A, G, or L proteins, can be labeled with a signal generator or reporter (e.g., colloidal gold) that is dried and placed on a glass fiber pad (sample application pad or conjugate pad). The diagnostic peptide or population of peptides of the invention is immobilized on membrane, such as nitrocellulose or a PVDF (polyvinylidene fluoride) membrane (e.g., an IMMOBILON™ membrane). When a solution of sample (blood, serum, etc.) is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide or population of peptides are present in the sample, they bind to the diagnostic peptide or population of peptides striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the peptides or compositions of the invention being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal (e.g., dog, mouse, deer) IgG/IgM antibodies or other peptides of the invention are immobilized on a membrane, such as nitrocellulose or PVDF, or POREX® membrane at a test site (e.g., a test line). When sample is added to the sample application pad, antibodies in the sample react with the labeled peptide complexes such that antibodies that bind to peptides of the invention become indirectly labeled. The antibodies in the sample are then transported into the next membrane (PVDF, POREX® membrane, or nitrocellulose containing the diagnostic peptide) by capillary action and bind to the immobilized anti-human IgG/IgM or anti-animal IgG/IgM antibodies (or protein A, protein G, protein A/G fusion proteins, protein L, or combinations thereof) or immobilized peptides of the invention. If any of the sample antibodies are bound to the labeled peptides of the invention, the label associated with the peptides can be seen or visualized at the test site. Another embodiment of this type of lateral flow device in which the peptides of the invention are used both as the immobilized capture agent at a test site and as a soluble labeled complex to react with antibodies in a sample is shown in FIG. 1. In such embodiments, to amplify the detection signal, protein A, protein G, and/or protein A/G fusion proteins conjugated to a detectable label (e.g., metallic nanomaterial such as nanoparticle, nanoplate, or nanoshell, HRP, β-GAL, ALP, fluorophore, colored latex particle or quantum dots) may be applied to the test site where they will bind to the Fc region of any antibodies to *Anaplasma* antigens captured by the immobilized peptides of the invention. Suitable controls for this assay can include, e.g., a chicken IgY-colloidal gold conjugate located at the sample application pad or conjugate pad, and an anti-chicken IgY antibody immobilized at a control site located proximal to the test site. Chicken anti-Protein A may also be used as the procedural control line.

Another assay for the screening of blood products or other physiological or biological fluids is an enzyme linked immunosorbent assay, i.e., an ELISA. Typically in an ELISA, isolated peptides or mixtures or populations of peptides of the invention are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO blocking buffer (a buffered solution of nonfat dry milk which also contains a preservative, salts, and an antifoaming agent, available from Thermo Scientific as BLOCKER™ BLOTTO). The well is then incubated with a biological sample suspected of containing specific anti-*Anaplasma* (e.g., anti-*A. phagocytophilum* or anti-*A. platys*) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) or another peptide or population of peptides of the invention that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), glucose oxidase, β-GAL, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where anaplasmosis is not endemic, or by other such conventional definitions. In the case of a very specific assay, OD+2 SD can be used as a cutoff value.

In one embodiment of an ELISA, a peptide or population of peptides of the invention is immobilized on a surface, such as a ninety-six-well ELISA plate or equivalent solid phase that is coated with streptavidin or an equivalent biotin-binding compound, such as avidin or neutravidin, at an optimal concentration in an alkaline coating buffer and incubated at 4° C. overnight. After a suitable number of washes with standard washing buffers, an optimal concentration of a biotinylated form of a peptide or composition of the invention, dissolved in a conventional blocking buffer, is applied to each well. A sample is then added, and the assay proceeds as above. Conditions for performing ELISA assays are well-known in the art.

In another embodiment of an ELISA, a peptide or population of peptides of the invention is immobilized on a surface, such as a ninety-six-well ELISA plate or equivalent solid phase via a fusion partner, e.g., BSA or MAPS. A sample is then added and the assay proceeds as above.

An alternative format for the ELISA assay features the peptide(s) of the invention being attached (e.g., fused) to an appropriate enzyme, such as HRP. Steps for carrying out such an ELISA include: coating the wells of a plate with anti-dog, anti-cat, or anti-human IgG/IgM; incubating samples suspected of containing antibodies to the peptides of the invention with the immobilized anti-species IgG/IgM; removing unreacted sample and washing the wells with a suitable wash buffer; applying enzyme-coupled (e.g., HRP-coupled) peptide or population of peptides of the invention and allowing it to react with any captured anti-*Anaplasma* antibodies; and visualizing the enzyme-coupled peptide by applying an appropriate enzyme substrate (e.g., TMB).

In another embodiment, the methods comprise an agglutination assay. For example, in certain embodiments, metallic nanoparticles, metallic nanoplates, or metallic nanoshells (e.g., colloidal gold, etc.) or latex beads are conjugated to peptides or compositions of the invention. Subsequently, the biological fluid is incubated with the bead/peptide conjugate, thereby forming a reaction mixture. The reaction mixture is then analyzed to determine the presence of the antibodies. In certain embodiments, the agglutination assays comprise the use of a second population of particles, such as metallic nanoparticles, metallic nanoplates, or metallic nanoshells (e.g., colloidal gold, etc.) or latex beads, conjugated to (1) antibodies specific to the peptides or compositions of the invention, in the case of a competition assay, or (2) antibodies capable of detecting sample antibodies (e.g., anti-human IgG or IgM antibodies, anti-dog IgG or IgM antibodies, anti-cat IgG or IgM antibodies, etc.), in the case of a sandwich assay. Suitable agglutination methods can comprise centrifugation as a means of assessing the extent of agglutination.

In still other embodiments, peptide or compositions of the invention are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using metallic nanomaterial such as nanoparticles, nanoplates, or nanoshells coupled to secondary antibodies or other antibody binding agents, such as protein A, protein G, protein A/G fusion proteins, protein L, or combinations thereof.

It should be understood by one of skill in the art that any number of conventional protein assay formats, particularly immunoassay formats, may be designed to utilize the isolated peptides or populations of peptides of this invention for the detection of *Anaplasma* antibodies and infection by pathogenic *Anaplasma* (e.g., *A. phagocytophilum, A. platys*, or *A. marginale*) in a subject. This invention is thus not limited by the selection of the particular assay format, and is believed to encompass assay formats that are known to those of skill in the art.

In certain embodiments, the sample used in the methods is a bodily fluid, such as blood, plasma, serum, cerebrospinal fluid, urine, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

Much of the preceding discussion is directed to the detection of antibodies against pathogenic *Anaplasma*. However, it is to be understood that the discussion also applies to the detection of primed T-cells, either in vitro or in vivo.

It is expected that a cell-mediated immune response (e.g., a T-helper response) is generated, since IgG is produced. It is therefore expected that it will be possible to determine the immunological reactivity between primed T-cells and a peptide of the invention. In vitro this can be done by incubating T-cells isolated from the subject with a peptide or population of peptides of the invention and measuring the immunoreactivity, e.g., by measuring subsequent T-cell proliferation or by measuring release of cytokines from the T-cells, such as IFN-γ. These methods are well-known in the art.

When a method of the invention is carried out in vivo, any of a variety of conventional assays can be used. For example, one can perform an assay in the form of a skin test, e.g., by intradermally injecting, in the subject, a peptide or population of peptides of the invention. A positive skin reaction at the location of injection indicates that the subject has been exposed to and infected with a pathogenic *Anaplasma* species capable of causing anaplasmosis, and a negative skin response at the location of injection indicates that the subject has not been so exposed/infected. This or other in vivo tests rely on the detection of a T-cell response in the subject.

The present invention also provides a method for diagnosing anaplasmosis in a subject. Anaplasmosis in humans was previously known as human granulocytic ehrlichiosis and has more recently been termed human granulocytic anaplasmosis. Some strains of *Anaplamsa* (e.g., *A. platys*) cause cyclic thrombocytopenia in animals (e.g. in dogs, the disease is termed Infectious Canine Cyclic Thrombocytopenia (ICCT)). Thus, the present invention also provides a method for diagnosing cyclic thrombocytopenia or ICCT in a subject. The subject can be a subject suspected of having antibody against a causative agent of anaplasmosis or cyclic thrombocytopenia. The diagnostic method is useful for diagnosing subjects exhibiting the clinical symptoms of anaplasmosis or cyclic thrombocytopenia. Clinical symptoms of human anaplasmosis (i.e., human granulocytic anaplasmosis) include, but are not limited to, fever, headache, malaise, chills, myalgia, abdominal pain, cough, confusion, thrombocytopenia, leukopenia, and elevated serum transaminase levels. Clinical symptoms of anaplasmosis or cyclic thrombocytopenia in animals (e.g. canines) include, but are not limited to, profound anemia, tachycardia, dyspnea, diarrhea, anorexia, weight loss, ataxia, leukopenia, lethargy, lymphadenomegaly, pale mucous membranes, fever, mucopurulent nasal discharge, inappetance, weak or painful limbs, and lameness.

In some embodiments, the methods comprise contacting a sample from the subject with a peptide of the invention, and detecting formation of an antibody-peptide complex comprising said peptide, wherein formation of said complex is indicative of the subject having anaplasmosis or cyclic thrombocytopenia. In certain embodiments, the methods comprise contacting the sample with a population of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention and detecting formation of an antibody-peptide complex comprising said one or more peptides in the population, wherein formation of the complex is indicative of the subject having anaplasmosis or cyclic thrombocytopenia. For instance, in one particular embodiment, the methods comprise contacting the sample with a population of two or more different isolated peptides, wherein each isolated peptide comprises a sequence of SEQ ID NO: 1. In another particular embodiment, the methods comprise contacting the sample with a population of two or more different isolated peptides, wherein each isolated peptide comprises a sequence of SEQ ID NO: 3. In still another embodiment, the methods comprise contacting the sample with a population of two or more different isolated peptides, wherein each isolated peptide comprises a sequence of SEQ ID NO: 4. In some embodiments, the methods comprise contacting the sample with a population of two or more different isolated peptides, wherein each isolated peptide comprises a sequence of SEQ ID NO: 2, SEQ ID NO: 5, SEQ ID NO: 6, SEQ ID NO: 7, SEQ ID NO: 8, SEQ ID NO: 9, or SEQ ID NO: 543.

In certain embodiments, the methods comprise contacting the sample with a mixture of one or more peptides of the invention and one or more other peptides (e.g., an *Ehrlichia* peptide, or antigenic fragment or epitope thereof, or a *Borrelia* peptide, or antigenic fragment or epitope thereof.) Co-infections with *Anaplasma* and *Ehrlichia* or *Borrelia* species are common. Thus, diagnostic methods of the invention that employ populations of peptides comprising the *Anaplasma* peptides described herein and one or more peptides from an *Ehrlichia* or *Borrelia* species are useful for detecting such co-infections. Exemplary *Ehrlichia* antigenic peptides that may be used with the *Anaplasma* peptides of the invention are described in U.S. application Ser. No. 14/052,296 and U.S. Pat. No. 8,828,675, both of which are incorporated by reference herein in their entireties. Exemplary *Borrelia* antigenic peptides that may be used with the *Anaplasma* peptides of the invention are described in U.S. Pat. Nos. 8,568,989 and 8,758,772, both of which are incorporated by reference herein in their entireties. Other *Ehrlichia* and *Borrelia* antigens are known in the art and may be used in combination with the *Anaplasma* peptides of the invention to detect co-infections in a subject.

In certain embodiments, the peptide or each peptide in the population is an isolated (e.g., synthetic and/or purified) peptide. In some embodiments, the peptide or population of different peptides is attached to or immobilized upon a substrate (e.g., a solid or semi-solid support). For example, in certain embodiments, the substrate is a bead or plurality of beads (e.g., a colloidal or other type of particle or metallic nanomaterial such as nanoparticle, nanoplate, or nanoshell), a flow path in a lateral flow immunoassay device (e.g., a porous membrane), a flow path in an analytical or centrifugal rotor, a blot (e.g., a Western blot, dot blot, or slot blot), a tube or a well (e.g., in a plate suitable for an ELISA assay), or a sensor (e.g., an electrochemical, optical, or opto-electronic sensor). In some embodiments, the peptide or population of peptides is attached to or immobilized upon a solid support through a metallic nanolayer that, in some embodiments, may be comprised of cadmium, zinc, mercury, or a noble metal (e.g., gold, silver, copper, and platinum).

There are a number of different conventional assays for detecting formation of an antibody-peptide complex comprising a peptide of the invention. For example, the detecting step can comprise performing an ELISA assay, performing a lateral flow immunoassay, performing an agglutination assay, performing a wavelength shift assay, analyzing the sample using a Western blot, a slot blot, or a dot blot, performing an Indirect Fluorescent Antibody test, analyzing the sample in an analytical or centrifugal rotor, or analyzing the sample with an electrochemical, optical, or opto-electronic sensor. These different assays are described above and/or are well-known to those skilled in the art.

In certain embodiments, the sample used in the diagnostic methods of the invention is a bodily fluid, such as blood, plasma, serum, cerebrospinal fluid, urine, or saliva. In other embodiments, the sample is a tissue (e.g., a tissue homogenate) or a cell lysate. In certain embodiments, the subject is a wild animal (e.g., a deer or rodent, such as a mouse, chipmunk, squirrel, etc.). In other embodiments, the subject is a lab animal (e.g., a mouse, rat, guinea pig, rabbit, monkey, primate, etc.). In other embodiments, the subject is a domesticated or feral animal (e.g., a dog, a cat, a horse). In still other embodiments, the subject is a human.

The present invention also includes a method for identifying the species of *Anaplasma* infecting a subject. Such methods aid in the treatment of the infection in the subject because treatment regimens may differ depending on the particular *Anaplasma* species causing the infection. The species identification methods are also useful in the epidemiology of *Anaplasma* infections and anaplasmosis. In certain embodiments, the method distinguishes between infections caused by *A. phagocytophilum* and infections caused by *A. platys*. In one embodiment, the method comprises contacting a sample from the subject with a first peptide or population of isolated peptides and a second peptide or population of isolated peptides, wherein the first peptide or population of isolated peptides specifically binds to antibodies against antigens from multiple *Anaplasma* species, and wherein the second peptide or population of isolated peptides specifically binds to antibodies against antigens from a single *Anaplasma* species. Formation of a first antibody-peptide complex comprising said first peptide or one or more peptides in the first population and formation of a second antibody-peptide complex comprising said second peptide or one or more peptides in the second population are detected, wherein formation of both the first and second antibody-peptide complexes indicates that the subject is infected with the *Anaplasma* species that is specifically bound by the second peptide or population of isolated peptides.

In some embodiments, the first peptide or first population of peptides specifically binds to antibodies against antigens from *A. phagocytophilum, A. platys*, and *A. marginale*. In certain embodiments, the first peptide or first population of peptides specifically binds to antibodies against antigens from both *A. phagocytophilum* and *A. platys*. For example, in one embodiment, the first peptide comprises a sequence of SEQ ID NO: 3. In another embodiment, the first population of peptides comprises three or more different peptides, wherein each peptide in the population comprises a sequence of SEQ ID NO: 3 or a fragment thereof. In such embodiments, the first population of peptides may comprise three or more peptides listed in Table 3 (i.e., three or more peptides comprising or consisting of sequences of SEQ ID NOs: 199-350).

In certain embodiments, the second peptide or second population of peptides specifically binds to antibodies against antigens from *A. platys*. For instance, in one embodiment, the second peptide comprises a sequence of SEQ ID NO: 4. In another embodiment, the second population of peptides comprises three or more different peptides, wherein each peptide in the population comprises a sequence of SEQ ID NO: 4 or a fragment thereof. In such embodiments, the first population of peptides may comprise three or more peptides listed in Table 4 (i.e., three or more peptides comprising or consisting of sequences of SEQ ID NOs: 351-398). In other embodiments, the second peptide or second population of peptides may comprise a sequence of SEQ ID NOs. 6-8. In related embodiments, the second population of peptides comprises three or more different peptides listed in Tables 6 or 7 (i.e., three or more peptides comprising or consisting of sequences of SEQ ID NOs: 407-464).

In such embodiments in which the second peptide or second population of peptides specifically binds to antibodies against antigens from *A. platys*, formation of both the first and second antibody-peptide complexes indicates that the subject is infected with *A. platys*. In related embodiments, formation of the first antibody-peptide complex, but not the second antibody-peptide complex indicates that the subject is infected with *A. phagocytophilum*. For instance, in certain embodiments, the first population of isolated peptides is defined by SEQ ID NO: 3 and the second population of isolated peptides is defined by SEQ ID NO: 4, and formation of both the first and second antibody-peptide complexes is detected indicating that the subject is infected with *A. platys*. In other embodiments, the first population of isolated peptides is defined by SEQ ID NO: 3 and the second population of isolated peptides is defined by any one of SEQ ID NOs: 6 to 8, and formation of both the first and second antibody-peptide complexes is detected indicating that the subject is infected with *A. platys*. In some embodiments, the first population of isolated peptides is defined by SEQ ID NO: 3 and the second population of isolated peptides is defined by SEQ ID NO: 4, and formation of the first antibody-peptide complex, but not the second antibody-peptide complex is detected indicating that the subject is infected with *A. phagocytophilum*. In other embodiments, the first population of isolated peptides is defined by SEQ ID NO: 3 and the second population of isolated peptides is defined by any one of SEQ ID NOs: 6 to 8, and formation of the first antibody-peptide complex, but not the second antibody-peptide complex is detected indicating that the subject is infected with *A. phagocytophilum*.

In alternative embodiments, the second peptide or second population of peptides specifically binds to antibodies against antigens from *A. phagocytophilum*. For instance, in one embodiment, the second peptide comprises a sequence of SEQ ID NO: 1. In another embodiment, the second population of peptides comprises three or more different peptides, wherein each peptide in the population comprises a sequence of SEQ ID NO: 1 or a fragment thereof. In such embodiments, the first population of peptides may comprise three or more peptides listed in Table 1 (i.e., three or more peptides comprising or consisting of sequences of SEQ ID NOs: 10-117). In other embodiments, the second peptide or second population of peptides may comprise a sequence of SEQ ID NOs. 2, 5, or 9. In related embodiments, the second population of peptides comprises three or more different peptides listed in Tables 2, 5, or 8 (i.e., three or more peptides comprising or consisting of sequences of SEQ ID NOs: 118-198, 399-406, or 465-542).

In such embodiments in which the second peptide or second population of peptides specifically binds to antibodies against antigens from *A. phagocytophilum*, formation of both the first and second antibody-peptide complexes indicates that the subject is infected with *A. phagocytophilum*. In related embodiments, formation of the first antibody-peptide complex, but not the second antibody-peptide complex indicates that the subject is infected with *A. platys*. For instance, in certain embodiments, the first population of isolated peptides is defined by SEQ ID NO: 3 and the second population of isolated peptides is defined by SEQ ID NO: 1, and formation of both the first and second antibody-peptide complexes is detected indicating that the subject is infected with *A. phagocytophilum*. In other embodiments, the first population of isolated peptides is defined by SEQ ID NO: 3 and the second population of isolated peptides is defined by any one of SEQ ID NOs: 2, 5, or 9, and formation of both the first and second antibody-peptide complexes is detected indicating that the subject is infected with *A. phagocytophilum*. In some embodiments, the first population of isolated peptides is defined by SEQ ID NO: 3 and the second population of isolated peptides is defined by SEQ ID NO: 1, and formation of the first antibody-peptide complex, but not the second antibody-peptide complex is detected indicating that the subject is infected with *A. platys*. In other embodiments, the first population of isolated peptides is defined by SEQ ID NO: 3 and the second population of isolated peptides is defined by any one of SEQ ID NOs: 2, 5, or 9, and formation of the first antibody-peptide complex, but not the second antibody-peptide complex is detected indicating that the subject is infected with *A. platys*.

The first and second antibody-peptide complexes can be detected using various methods including, but not limited to, performing an ELISA assay, running a lateral flow assay, performing an agglutination assay, performing a Western blot, a slot blot, or dot blot, performing a wavelength shift assay, performing an Indirect Fluorescent Antibody test, or running the sample through an analytical or centrifugal rotor. Such methods and devices for use in the methods are described in detail above.

In other embodiments, the method for identifying the species of *Anaplasma* infecting a subject comprises contacting a sample from the subject with a first population of peptides and a cell extract of a single *Anaplasma* species, wherein the first population of isolated peptides specifically binds to antibodies against antigens from multiple *Anaplasma* species; detecting formation of a first antibody-peptide complex comprising one or more peptides in the first population; and detecting formation of an antibody-cell extract complex comprising one or more components in the cell extract, wherein formation of both the first antibody-peptide complex and the antibody-cell extract complex indicates that the subject is infected with the *Anaplasma* species that produced the cell extract. In some embodiments, the cell extract is from *A. phagocytophilum*.

A cell extract comprises components of cells. It can be generated by lysing cells (e.g., with detergents) and removing unwanted components (e.g., using centrifugation to remove insoluble matter such as membrane fragments, vesicles, and nuclei). A cell extract can be a whole-cell lysate or partial-cell lysate. Cell extracts usually consist mostly of cytosol. Various methods of making cell extracts are well known to those of skill in the art. Commercial kits are available for generating cell extracts.

Kits

In yet another aspect, the invention provides kits for use in the detection and diagnostic assays described herein. In some embodiments, the kits comprise one or more peptides of the invention. In certain embodiments, the kits comprise a population of peptides of the invention. The peptides can comprise a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 543, or fragments thereof. In one embodiment, the kits comprise two or more populations of peptides of the invention. For example, in one embodiment, the kits comprise a first population of peptides defined by SEQ ID NO: 3 and a second population of peptides defined by SEQ ID NO: 4. In particular embodiments, the peptides are attached to or immobilized on a solid support. In some embodiments, the peptides are attached to or immobilized on a solid support through a metallic nanolayer (e.g., cadmium, zinc, mercury, gold, silver, copper, or platinum nanolayer). In certain embodiments, the solid support is a bead or plurality of beads (e.g., a colloidal particle or a metallic nanomaterial such as nanoparticles, nanoplates, or nanoshells), a flow path in a lateral flow immunoassay device, a flow path in an analytical or centrifugal rotor, a tube or a well (e.g., in a plate), or a sensor (e.g., an electrochemical, optical, or opto-electronic sensor).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical or centrifugal rotor, a Western blot, a dot blot, a slot blot, or an electrochemical, optical, or opto-electronic sensor. The population of beads, the plate, and the devices are useful for performing an immunoassay. For example, they can be useful for detecting formation of an antibody-peptide complex comprising an antibody from a sample and a peptide of the invention. In certain embodiments, a peptide, a population of different peptides of the invention, or a peptide composition of the invention is attached to or immobilized on the beads, the plate, or the device.

In addition, the kits can include various diluents and buffers, labeled conjugates or other agents for the detection of specifically bound antigens or antibodies (e.g. labeling reagents), and other signal-generating reagents, such as enzyme substrates, cofactors and chromogens. In one embodiment, the kits comprise a labeling reagent capable of binding to an antibody that recognizes an epitope of one or more peptides of the invention. For instance, in some embodiments, the kit comprises an anti-human, anti-canine, or anti-feline IgG or IgM antibody conjugated to a detectable label (e.g., a metallic nanomaterial such as a nanoparticle, a nanoplate, or a metallic nanoshell, a metallic nanolayer, a fluorophore, a quantum dot, a colored latex particle, or an enzyme) as a labeling reagent. In other embodiments, the kit comprises protein A, protein G, protein A/G fusion proteins, protein L, or combinations thereof conjugated to a detectable label (e.g., a metallic nanomaterial such as a metallic nanoparticle, a metallic nanoplate, a metallic nanoshell, a metallic nanolayer, a fluorophore, a quantum dot, a colored latex particle, or an enzyme) as a labeling reagent. An exemplary protein A/G fusion protein combines four Fc-binding domains from protein A with two from protein G. See, e.g., Sikkema, J. W. D., Amer. Biotech. Lab, 7:42, 1989 and Eliasson et al., J. Biol. Chem. 263, 4323-4327, 1988, both which are hereby incorporated by reference in their entireties. In still other embodiments, the labeling reagents of the kit are a second population of peptides of the invention conjugated to a detectable label (e.g., a metallic nanomaterial such as a metallic nanoparticle, a metallic nanoplate, a metallic nanoshell, a metallic nanolayer, a fluorophore, a colored latex particle, or an enzyme). The second population of peptides can be the same as or different than the first population of peptides, which may optionally be attached to or immobilized upon a solid support.

Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, monoclonal antibody detector antibodies, an anti-mouse, anti-dog, anti-cat, anti-chicken, or anti-human antibody conjugated to a detectable label, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

Such kits provide a convenient, efficient way for a clinical laboratory to diagnose infection by a pathogenic *Anaplasma* species, such as *A. phagocytophilum, A. platys*, or *A. marginale*. Thus, in certain embodiments, the kits further comprise an instruction. For example, in certain embodiments, the kits comprise an instruction indicating how to use a peptide or population of peptides of the invention to detect an antibody to one or more *Anaplasma* antigens or to diagnose anaplasmosis or cyclic thrombocytopenia. In certain embodiments, the kits comprise an instruction indicating how to use a population of beads, a plate, or a device (e.g., comprising a peptide or a population of different peptides of the invention) to detect an antibody to one or more *Anaplasma* antigens or to diagnose anaplasmosis or cyclic thrombocytopenia.

The peptides, compositions and devices comprising the peptides, kits and methods of the invention offer a number of advantages. For example, they allow for simple, inexpensive, rapid, sensitive and accurate detection of anaplasmosis or cyclic thrombocytopenia, and avoid serologic cross-reactivity with other conditions with similar symptoms. This allows for an accurate diagnosis. Furthermore, a diagnostic test of the invention (e.g., an ELISA assay, lateral flow immunoassay, or agglutination assay) is useful in serum samples that contain anti-MSP 2/p44 or anti-OMP/p44 antibodies or other antibodies produced in response to a vaccine based on the outer surface proteins of *Anaplasma*.

The following examples illustrate various aspects of the invention. The examples should, of course, be understood to be merely illustrative of only certain embodiments of the invention and not to constitute limitations upon the scope of the invention.

EXAMPLES

Example 1

ELISA Assay

Two different populations of peptides were synthesized using standard synthesis procedures. Each peptide in the first population of peptides (APL-ID1) contained a sequence of SEQ ID NO: 3. The first population of peptides specifically binds to antibodies elicited by both *A. phagocytophilum* and *A. platys*. Each peptide in the second population of peptides (APL-ID2) contained a sequence of SEQ ID NO: 4. The second population of peptides specifically binds to antibodies elicited primarily by *A. platys*.

Each peptide in the two populations was linked separately to the carrier protein bovine serum albumin (BSA) using thio-ether chemistry. The resulting BSA-peptide conjugates were used as capture entities in 96-well ELISA plates to create two separate ELISA assays (one population of peptides per plate). The plates were blocked with 5% non-fat milk powder dissolved in 25 mM borate buffer (pH9.5) to prevent undesirable non-specific binding.

Dogs were inoculated with *A. phagocytophilum*-infected tick cell cultures to initiate exposure of the dogs to *A. phagocytophilum*. Stabilized blood obtained from animals known to harbor *A. platys* infection as determined by PCR and microscopic examination was inoculated into a separate group of dogs for initiating infection with *A. platys*. Blood samples from each group of inoculated dogs were collected at various days following inoculation.

Plasma prepared from the blood samples was tested for reactivity with the APL-ID1 and APL-ID2 peptides using the ELISA plates described above. The plasma samples were diluted 1:250 to 1:1000 in blocking solution and added to blocked wells in each of the two ELISA plates. After a one-hour incubation period, the unreacted materials were removed by washing the micro wells. The specifically captured anti-peptide dog IgG or IgM were detected by reaction with HRP-labeled Protein A. HRP was assayed using a commercial TMB substrate. The optical density of each well was read at 650 nm with a plate reader.

Figure 5:
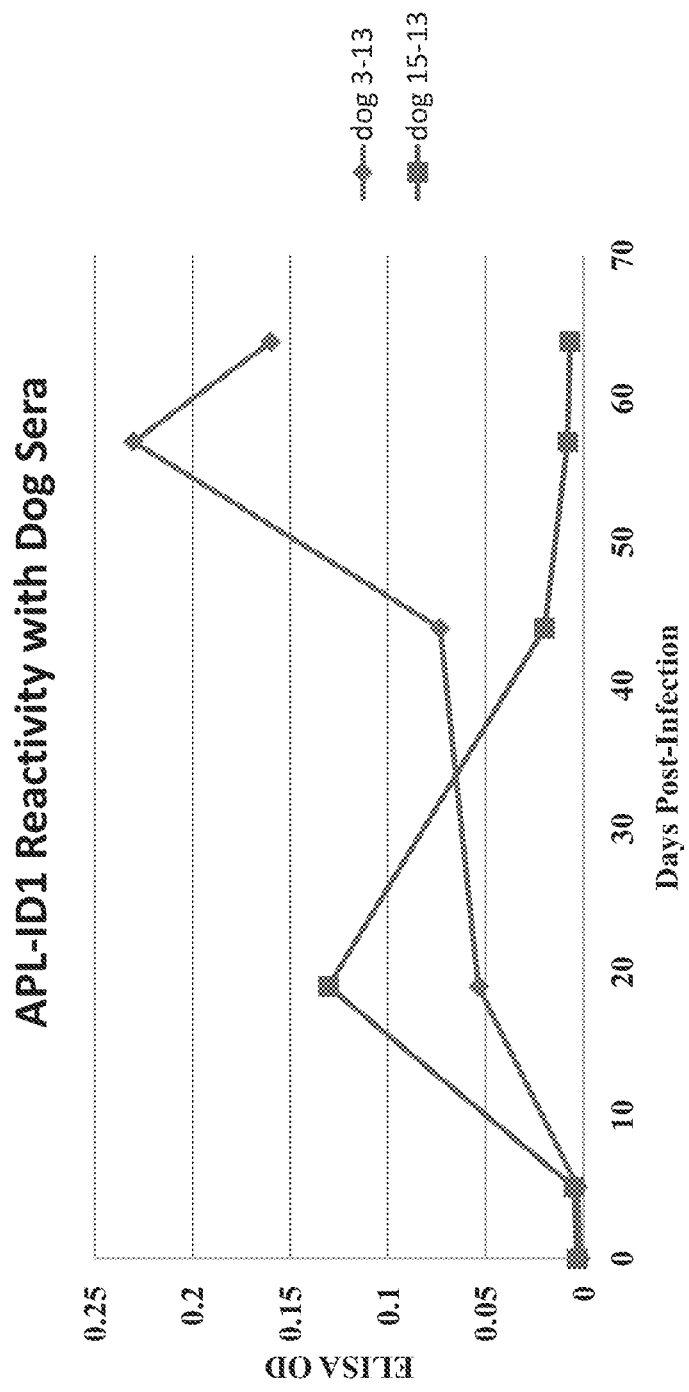
FIG. 5 is a line graph of ELISA scores (OD650 nm) with APL-ID1 peptides of plasma samples drawn at various intervals from dogs infected with either *A. phagocytophilum* (dog 3-13) or *A. platys* (dog 15-13).
Figure 6:
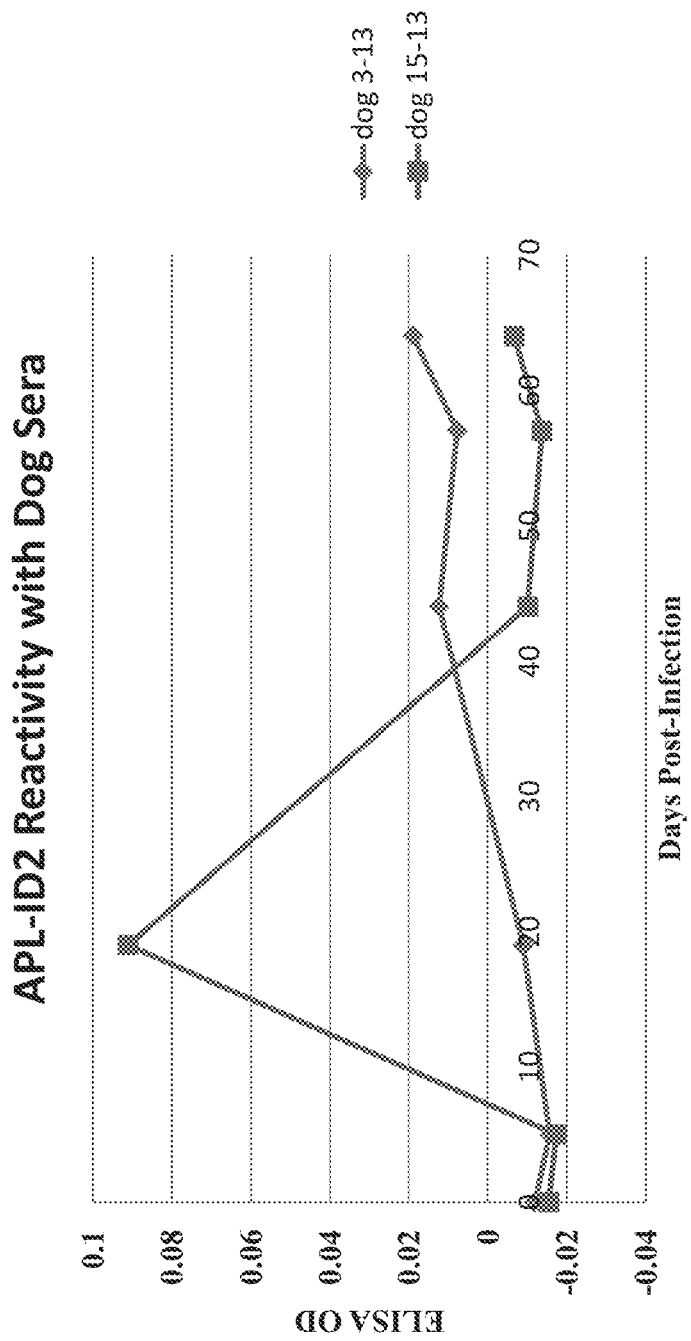
FIG. 6 is a line graph of ELISA scores (OD650 nm) with APL-ID2 peptides of plasma samples drawn at various intervals from dogs infected with either *A. phagocytophilum* (dog 3-13) or *A. platys* (dog 15-13).

Reactivity of plasma samples obtained from an *A. platys*-infected dog (15-13) and an *A. phagocytophilum*-infected dog (3-13) with APL-ID1 peptides and APL-ID2 peptides are shown in FIGS. 5 and 6, respectively. The samples from the *A. phagocytophilum*-infected dog (dog 3-13) showed significant reactivity with APL-ID1 peptides, whereas the reactivity of such samples with APL-ID2 peptides was much lower. In contrast, samples from the *A. platys*-infected dog (dog 15-13) showed similar reactivity towards both populations of peptides. These experimental results show that populations of peptides defined by SEQ ID NO: 3 (APL-ID1) and SEQ ID NO: 4 (APL-ID2) have a high degree of sensitivity in detecting the presence of antibodies to *Anaplasma* antigens. In addition, the results show that these two populations of peptides can be used to identify the infecting species of *Anaplasma*. A sample that tests positive for reactivity with APL-ID1 peptides, but not APL-ID2 peptides is positive for *A. phagocytophilum*, whereas a sample that tests positive for reactivity for both peptides is positive for *A. platys*.

Example 2

Lateral Flow Assay

Figure 7:
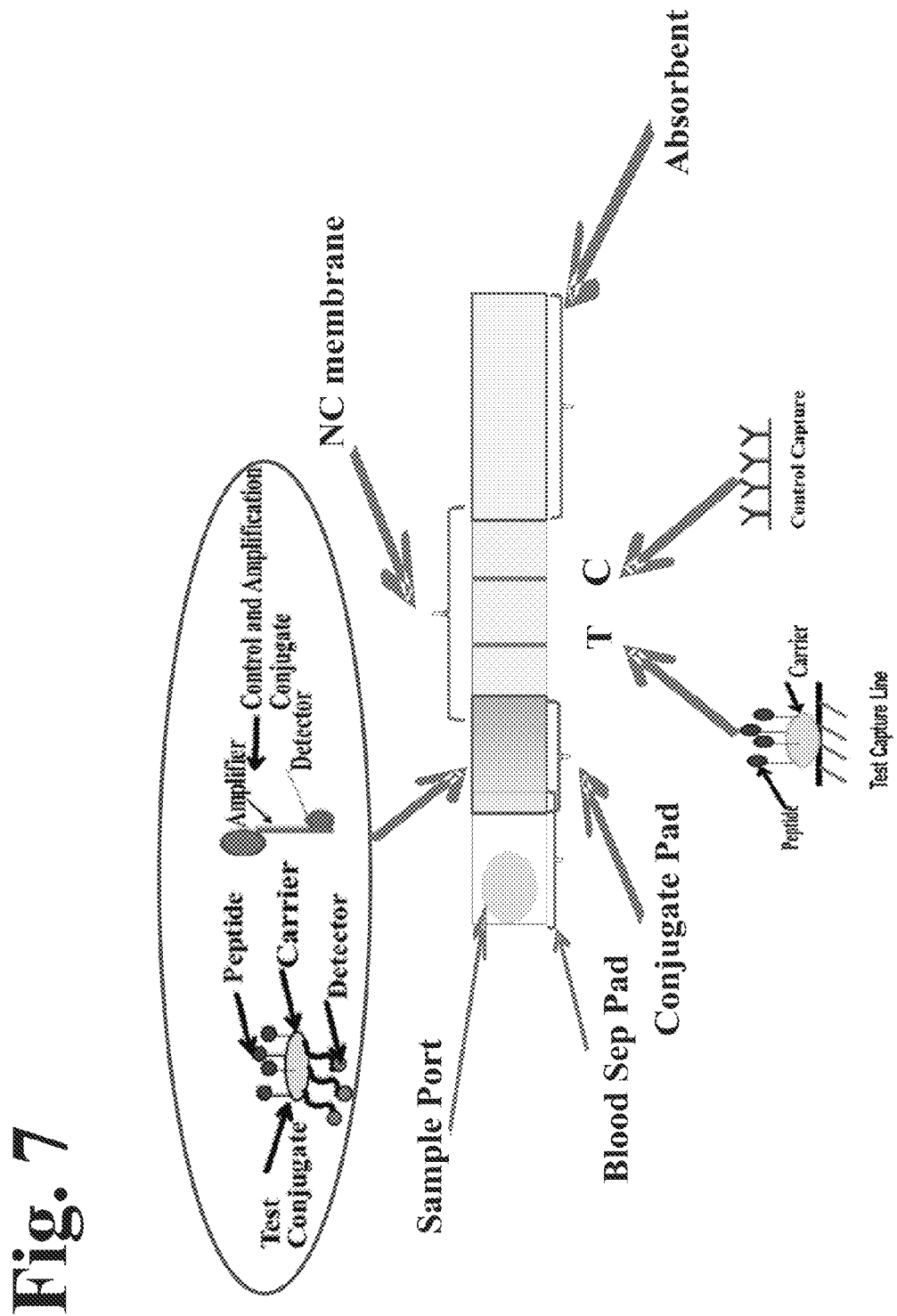
FIG. 7 depicts one example of a lateral flow assay device that can be used to detect antibodies to *Anaplasma* antigens. Peptides of the invention are linked to a carrier protein (e.g. bovine serum albumin) and the resulting BSA-peptide conjugates are immobilized on a nitrocellulose (NC) membrane at a test site (T). The same BSA-peptide conjugates are conjugated to a detectable label (e.g., colloidal gold) and deposited in a conjugate pad positioned upstream of the test site. Gold-conjugated protein A and gold-conjugated protein G (i.e. amplifier) is added to the conjugate pad to enhance the signal by binding to the Fc portion of the captured anti-*Anaplasma* antibody. The device further comprises a control site (C) at which binding partners that recognize the gold-conjugated protein A and/or gold-conjugated protein G are immobilized.

A lateral flow immunoassay in a double antigen sandwich format was constructed to detect the presence of antibodies specific for *Anaplasma* antigens. A population of peptides comprising peptides with a sequence of SEQ ID NO: 3 (APL-ID1), SEQ ID NO: 6 (APL-ID5.1), or SEQ ID NO: 7 (APL-ID6) was linked to BSA and the resulting complexes were used both as test conjugate (peptides labeled with gold nanoparticles) and as capture (immobilized at the test line of the device). The signal produced at the test line was enhanced by Protein A and Protein G-gold conjugates (amplifier) added to the labeled peptide conjugate. The device is depicted in FIG. 7.

Figure 8:
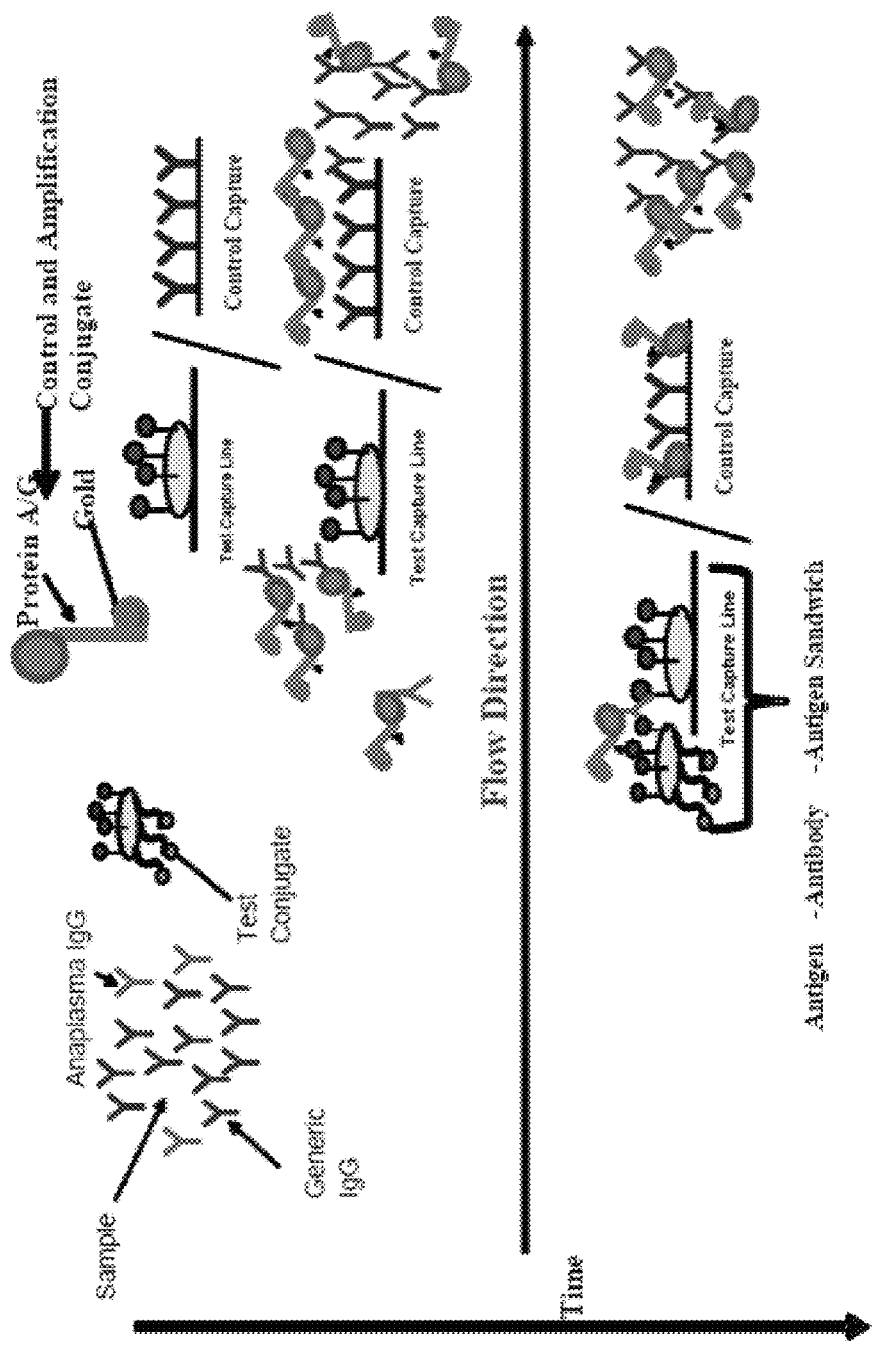
FIG. 8 illustrates the operation of the lateral flow assay device in FIG. 7. A test sample is applied to the sample port of the device and mobilizes the peptide conjugates present on the conjugate pad. Any anti-*Anaplasma* antibodies present in the test sample will specifically bind to the peptide conjugates and the formed complexes will migrate to the nitrocellulose membrane containing the test and control sites. The labeled peptide-antibody complexes are captured by immobilized peptides of the invention at the test site. Gold-conjugated protein A and gold-conjugated protein G also present on the conjugate pad are mobilized by the sample and bind to the Fc regions of IgG and IgM molecules present in the sample. Binding of the gold-conjugated protein A and/or protein G to the captured peptide-antibody complexes amplify the signal at the test site. Gold-conjugated protein A and/or gold-conjugated protein G is captured by a binding partner (e.g. anti-Protein A and/or anti-Protein G antibody) immobilized at the control site, thereby producing a signal indicating that the device is operational.

The operation of the device is illustrated in FIG. 8. To conduct the assay, one drop of anti-coagulated whole blood, serum, or plasma is applied to the sample port of the device. The blood separation pad filters blood cells from whole blood. Plasma (or serum) mobilizes and binds specifically to the test conjugate present on the conjugate pad and any formed antibody-peptide complexes migrate to the nitrocellulose membrane containing the test and the control regions. The application of a chase buffer after sample application moves the free and the bound test conjugates through the nitrocellulose membrane towards the upper absorbent pad. The labeled peptide-antibody complexes move to the test line where immobilized peptides capture labeled peptide-antibody complexes via the second binding sites on the antibodies. Protein A-gold and Protein G-gold conjugates in the conjugate mixture bind to captured antibodies amplifying the detection signal. The appearance of one red line at the test site and a second red line at the control site indicates the presence of antibodies to *Anaplasma* spp. (e.g., *phagocytophilum* or *platys*) in the sample. The appearance of a red line at only the control site indicates the absence of antibodies to all of the *Anaplasma* spp. in the sample. The test is considered invalid if (i) a signal at the test line appears but no signal at the control line is present or (ii) no signal is observed at either the control or test lines.

Ninety-five dog plasma samples positive for *Anaplasma* spp. as determined by indirect immunofluorescence assay, IDEXX SNAP 4DX PLUS™, and ELISA using the same peptide mixture, were tested in the lateral flow device. In addition, fifty-one dog plasma samples that were determined to be negative for *Anaplasma* spp. by the same methods were also evaluated. Each sample was tested twice in the device. Each test was performed by a different operator. At the end of the test period, each test was marked by the operator as either positive or negative. Additionally, scanned images of each test were obtained and analyzed by the ImageJ method. A test where both operators agreed on the designation was recorded as the same designation (pos/neg). Where operators disagreed, a third test was run by a third operator and taken as the final result (pos/neg) for that sample. The results are summarized in Table 9 below. The lateral flow assay had a sensitivity of 97.9% and a specificity of 90.2%. This example demonstrates that a population of peptides comprising peptides having a sequence of SEQ ID NO: 3, SEQ ID NO:6, or SEQ ID NO: 7 can effectively detect antibodies against *Anaplasma* antigens when employed in a lateral flow assay format.

TABLE 9

Lateral Flow Assay Results of Known Anaplasma-Positive and Negative Samples

|  | Negative by Lateral Flow | Positive by Lateral Flow |
| --- | --- | --- |
| No. of known negative samples | 46 | 5 |
| No. of known positive samples | 2 | 93 |

Example 3

Indirect Fluorescent Antibody Assay

An indirect fluorescent antibody test is constructed using latex beads coated with one or more peptides of the invention. In certain embodiments, the peptides defined by SEQ ID NO: 3 (APL-ID1), SEQ ID NO: 4 (APL-ID2), and/or SEQ ID NO: 6 (APL-ID5.1) are used. The peptides of the invention are coated onto maleimide-derivatized latex beads using thio-ether chemistry. Alternatively, the peptides of the invention may be conjugated to BSA via thio-ether or similar chemistries and are passively absorbed on to latex beads. A population of such beads is then immobilized on a glass slide using known techniques.

To conduct the assay, one drop of serum or plasma (diluted appropriately with a suitable buffer) from dogs suspected of having anti-*Anaplasma* antibodies, is applied to the glass slide coated with latex beads. Following a suitable incubation time, the unreacted materials are washed away and a drop of fluorescently labeled anti-dog IgG (or IgM) is applied and the slides are incubated for an additional time period. The final preparation is viewed under a fluorescent microscope to determine fluorescently tagged latex beads. The classification of the test serum/plasma as positive or negative is based on comparison with appropriate controls. An enzyme label may be used in place of the fluorescent label in which case the visualization step employs an enzyme substrate. For example, anti-dog IgG/IgM labeled with alkaline phosphatase can be visualized by exposing the slide to a BCIP-nitro BT substrate. Labeled Protein A, Protein G, or Protein A/G fusion can be used in place of labeled anti-dog IgG and anti-dog IgM to detect antibodies bound to the peptide-coated beads.

Example 4

Identification of the Species of *Anaplasma* Infecting Dogs in Unknown Samples

This example demonstrates successful identification of the species of *Anaplasma* infecting dogs using the peptide populations of the invention and *Anaplasma* cell extracts.

Forty one dog plasma samples, which were all tested and classified by visual inspection as positive for *Anaplasma* infection using the IDEXX SNAP 4DX PLUS™ assay, were tested in an ELISA assay similar to that described in Example 1. Three 96-well ELISA plates were coated with various peptides or cell extract (prepared using a commercial kit from Sigma-Aldrich) at room temperature for 1 hour. Plate 1 was coated with 100 µL/well of a mixture of three peptide populations: APL-ID1 (SEQ ID NO: 3, final concentration 7 µg/mL), APL-ID5.1 (SEQ ID NO: 6, final concentration 7 µg/mL), and APL-ID6 (SEQ ID NO: 7, final concentration 7 µg/mL). Plate 2 was coated with 100 µL/well of a mixture of two peptide populations: APL-ID5.1 (SEQ ID NO: 6, final concentration 7 µg/mL), and APL-ID6 (SEQ ID NO: 7, final concentration 7 µg/mL). Plate 3 was coated with 100 µL/well of an *A. phagocytophilum* whole-cell lysate (final concentration 5 µg/mL). The peptide mixture on plate 1 specifically binds to antibodies elicited by both *A. phagocytophilum* and *A. platys*. The peptide mixture on plate 2 specifically binds to antibodies elicited primarily by *A. platys*. The whole-cell lysate on plate 3 specifically binds to antibodies elicited primarily by *A. phagocytophilum*. The plates were then washed.

The plates were then blocked with 300 µL/well of 7% non-fat milk in 250 mM borate buffer (pH9.5) at room temperature for 1 hour to prevent undesirable non-specific binding. The plates were washed again.

Plasma samples from dogs with or without *Anaplasma* infection (the "unknown samples") were diluted 1/100 in 7% milk, and 100 µL/well of each sample were added to the ELISA plates and incubated at room temperature for 1 hour. The plates were washed again.

The plates were then incubated with 100 µL/well of Protein A-HRP conjugate (diluted 1:1000) at room temperature for 1 hour. The plates were washed again, and 100 µL/well of substrate (TMB) was added and incubated at room temperature for 10 minutes. OD readings of all the samples were obtained and compared to standard curves. For plate 1 and plate 2 (the two "peptide" plates), serial dilutions of pooled positive samples were used to create standard curves. For plate 3 (the lysate plate), a two point curve was made using a negative sample and a canine sample from a dog which was experimentally infected with *A. phagocytophilum* ("3-13").

Species identification results of these samples using the peptide-cell extract ELISA, along with the results of the SNAP test and an indirect immunofluorescence assay (IFA), are shown in Table 10. Both the SNAP and the IFA tests only detected *Anaplasma* at the genus level and could not be used to determine the species of *Anaplasma*.

TABLE 10

Identification of *Anaplasma* Species in Unknown Samples

| Sample ID | Combo Score$^a$ | platys Score$^b$ | phago WCL score$^c$ | *Anaplasma* species determined with peptides and cell extract$^d$ | SNAP 4DX Plus ™ (*Anaplasma*) result$^e$ | IFA titer$^f$ |
|---|---|---|---|---|---|---|
| 1 | 214 | 986 | 315 | platys | 31.6% | 25600 |
| 2 | 9 | 1 | 97 | NEG | 40.1% | 25600 |
| 3 | 37 | 19 | 107 | phago | 14.7% | 12800 |
| 4 | 17 | 5 | 151 | phago | 30.1% | 25600 |
| 5 | 68 | 24 | 38 | phago | 18.3% | 6400 |
| 6 | 37 | 27 | 47 | phago | 23.8% | 6400 |
| 7 | 21 | 6 | 30 | phago | 7.0% | 3200 |
| 8 | 10 | 2 | 39 | phago | 18.7% | 6400 |
| 9 | 29 | 2 | 172 | phago | 32.0% | 25600 |
| 10 | 12 | 1 | 86 | phago | 14.5% | 12800 |
| 11 | 6 | −1 | 89 | NEG | 12.4% | 3200 |
| 12 | 165 | 0 | 110 | phago | 39.0% | 25600 |
| 13 | 52 | 2 | 362 | phago | 37.3% | 25600 |
| 14 | 18 | −1 | 69 | phago | 40.0% | 25600 |
| 15 | 49 | 3 | 206 | phago | 39.3% | 25600 |
| 16 | 26 | 10 | 79 | phago | 22.2% | 3200 |
| 17 | 34 | 4 | 30 | phago | 25.3% | 6400 |
| 18 | 40 | 2 | 82 | phago | 34.3% | 25600 |
| 19 | 6 | 2 | 51 | NEG | 11.4% | 3200 |
| 20 | 22 | 0 | 141 | phago | 26.8% | 1600 |
| 21 | 302 | 245 | 8 | platys | 25.9% | 12800 |
| 22 | 91 | 33 | 10 | platys | 17.5% | 1600 |
| 23 | 12 | 7 | 24 | phago | 46.3% | 51200 |
| 24 | 483 | 714 | 6 | platys | 11.7% | 6400 |
| 25 | 61 | 53 | 18 | platys | 19.7% | 6400 |
| 26 | 117 | 122 | 49 | platys | 7.3% | 51200 |
| 27 | 244 | 140 | 16 | platys | 27.7% | 12800 |
| 28 | 25 | 37 | 15 | platys | 28.2% | 12800 |
| 29 | 56 | 72 | 21 | platys | 17.9% | 12800 |
| 30 | 156 | 250 | 2 | platys | 9.2% | 1600 |
| 31 | 517 | 880 | 17 | platys | 39.3% | 12800 |
| 32 | 23 | 25 | 30 | phago | 8.3% | 3200 |
| 33 | 6 | 4 | 24 | NEG | 20.9% | 25600 |
| 34 | 18 | 23 | 5 | platys | 13.8% | 1600 |
| 35 | 82 | 79 | 33 | platys | 45.0% | 6400 |
| 36 | 35 | 27 | 18 | platys | 17.1% | 3200 |
| 37 | 354 | 256 | 26 | platys | 49.0% | 6400 |
| 38 | 6 | 19 | 36 | NEG | 43.9% | 25600 |
| 39 | 20 | 45 | 20 | platys | 19.7% | 12800 |
| 40 | 60 | 186 | 8 | platys | 1.3% | 1600 |
| 41 | 2 | 1 | 46 | NEG | 4.9% | <1:50 (NEG) |

$^a$Combo Score was calculated by comparing OD readings of unknown samples from Plate 1 to a standard curve generated with OD readings of a serially diluted calibrator made of known positive samples analyzed under the same conditions (with peptide populations APL-ID1, APL-ID5.1, and APL-ID6).
$^b$platys Score was calculated by comparing OD readings of unknown samples from Plate 2 to a standard curve generated with OD readings of a serially diluted calibrator made of known positive samples analyzed under the same conditions (with peptide populations APL-ID5.1, and APL-ID6).
$^c$phago WCL Score was calculated by comparing OD readings of unknown samples from Plate 3 to a two point standard curve comprised of result from a healthy dog's plasma sample (negative control) and result from a plasma sample from 3-13, a dog experimentally infected with *A. phagocytophilum*, analyzed under the same conditions (with *A. phagocytophilum* whole-cell lysate).
$^d$Identification of the *Anaplasma* species infecting dogs in unknown samples using the Combo Score, platys Score, and phago WCL Score. Samples with Combo Scores of 9 or lower are classified as negative for *Anaplasma* infection ("NEG"). Samples with Combo Scores higher than 9 are classified as positive for *Anaplasma* infection and the infecting *Anaplasma* species are assigned by comparing the platys Score with the phago WCL Score--samples with higher platys Scores than phago WCL Scores are classified as positive for *A. platys* infection ("platys"), and samples with lower platys Scores than phago WCL Scores are classified as positive for *A. phagocytophilum* infection ("phago"). If a sample's platys Score is identical to its phago WCL Score, and its combo score is greater than 9, the sample is classified as positive for *Anaplasma* infection with species indeterminate.
$^e$IDEXX SNAP 4DX Plus ™ assay was performed according to manufacturer's instruction. Percentages were calculated through densitometry analysis of images of the SNAP cassettes. They represent "(density of test sample)/(density of test sample + density of positive control)".
$^f$The IFA assay was performed with a commercial kit which used *A. phagocytophilum* cells to detect antibodies against *Anaplasma*. IFA titers were determined by serially diluting plasma samples and testing each dilution with immobilized *A. phagocytophilum* cells.

The result in this Example demonstrates that the species of *Anaplasma* infecting a subject can be successfully identified using the peptide populations and cell extract. In addition, a positive control sample from an *A. phagocytophilum*-infected dog, 3-13, was correctly identified in this Example (data not shown).

To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention. Accordingly, the invention is limited only by the following claims.

The disclosures, including the claims, figures and/or drawings, of each and every patent, patent application, and publication cited herein are hereby incorporated herein by reference in their entireties.

The invention claimed is:

1. A composition comprising a population of isolated peptides, said population comprising three or more different peptides, wherein at least one peptide in the population comprises the sequence of SEQ ID NO; 6, and wherein the population further comprises two or more different peptides selected from:

(i) SEQ ID NO: 1 or a fragment thereof, wherein $X_9$ is an amino acid selected from the group consisting of I, P and H, $X_{17}$ is an amino acid selected from the group consisting of I, W, and Y, $X_{21}$ is an amino acid selected from the group consisting of R, D, and N, $X_{28}$ is an amino acid selected from the group consisting of E and N, and $X_{31}$ is an amino acid selected from the group consisting of L and V;

(ii) SEQ ID NO: 2 or a fragment thereof, wherein $X_3$ is an amino acid selected from the group consisting of L, V and A, $X_7$ is an amino acid selected from the group consisting of K, N and Q, $X_{11}$ is an amino acid selected from the group consisting of R, D, and N, and $X_{15}$ is an amino acid selected from the group consisting of E, N and Q;

(iii) SEQ ID NO: 3 or a fragment thereof, wherein $X_5$ is an amino acid selected from the group consisting of V and A, $X_7$ is an amino acid selected from the group consisting of G, I and H, $X_{11}$ is an amino acid selected from the group consisting of E, N, and Q, $X_{18}$ is an amino acid selected from the group consisting of D and N, $X_{21}$ is an amino acid selected from the group consisting of R, D, and N, $X_{25}$ is an amino acid selected from the group consisting of Q, D, and E, $X_{28}$ is an amino acid selected from the group consisting of E and N, $X_{31}$ is an amino acid selected from the group consisting of L and V, $X_{45}$ is an amino acid selected from the group consisting of K and Q, $X_{48}$ is an amino acid selected from the group consisting of F and V, $X_{51}$ is an amino acid selected from the group consisting of D and N, $X_{54}$ is an amino acid selected from the group consisting of E and Q, $X_{57}$ is an amino acid selected from the group consisting of S and Q, $X_{60}$ is an amino acid selected from the group consisting of F and W, $X_{63}$ is an amino acid selected from the group consisting of I and V, and $X_{66}$ is an amino acid selected from the group consisting of Q and D;

(iv) SEQ ID NO: 4 or a fragment thereof, wherein $X_6$ is an amino acid selected from the group consisting of K and Q, $X_9$ is an amino acid selected from the group consisting of F and V, $X_{12}$ is an amino acid selected from the group consisting of D and N, $X_{15}$ is an amino acid selected from the group consisting of E and Q, $X_{18}$ is an amino acid selected from the group consisting of S and Q, $X_{21}$ is an amino acid selected from the group consisting of F and W, $X_{24}$ is an amino acid selected from the group consisting of I and V, and $X_{27}$ is an amino acid selected from the group consisting of Q and D;

(v) SEQ ID NO: 5 or a fragment thereof, wherein $X_2$ is an amino acid selected from the group consisting of I and V, $X_{10}$ is an amino acid selected from the group consisting of S and Y, and $X_{23}$ is an amino acid selected from the group consisting of E and N;

(vi) SEQ ID NO: 7 or a fragment thereof, wherein $X_5$ is an amino acid selected from the group consisting of S and Q, $X_9$ is an amino acid selected from the group consisting of F and Y, $X_{13}$ is an amino acid selected from the group consisting of R and H, $X_{16}$ is an amino acid selected from the group consisting of W and Y, $X_{18}$ is an amino acid selected from the group consisting of S and Q, $X_{22}$ is an amino acid selected from the group consisting of K and H, and $X_{27}$ is an amino acid selected from the group consisting of N and D;

(vii) SEQ ID NO: 8 or a fragment thereof, wherein $X_{10}$ is an amino acid selected from the group consisting of V, L and I, and $X_{11}$ is an amino acid selected from the group consisting of A and L; and (viii) SEQ ID NO: 9 or a fragment thereof, wherein $X_5$ is an amino acid selected from the group consisting of V and A, $X_7$ is an amino acid selected from the group consisting of G, I and H, $X_{11}$ is an amino acid selected from the group consisting of E, N, and Q, $X_{21}$ is an amino acid selected from the group consisting of R, D, and N, $X_{25}$ is an amino acid selected from the group consisting of Q, D, and E, $X_{28}$ is an amino acid selected from the group consisting of E and N, and $X_{31}$ is an amino acid selected from the group consisting of L and V.

2. The composition of claim 1, wherein one or more of the peptides is conjugated to a ligand.

3. The composition of claim 1, wherein one or more of the peptides is conjugated to biotin, avidin, streptavidin, neutravidin, serum albumin, keyhole limpet hemocyanin (KLH), an enzyme, or a metallic nanomaterial.

4. The composition of claim 1, wherein the population of peptides is immobilized to a solid support optionally through a metallic nanolayer.

5. The composition of claim 4, wherein the solid support is a plurality of beads, a flow path in a lateral flow immunoassay device, a well in a microtiter plate, or a flow path in a rotor.

6. The composition of claim 1, wherein the fragment is at least 15, 20, 25, 30, 35, 40, 45, 50, 55, or 60 amino acids long.

7. The composition of claim 1, wherein the composition further comprises one or more antigenic peptides from an *Anaplasma* species, an *Ehrlichia* species, and/or a *Borrelia* species.

8. The composition of claim 1, wherein at least one of the two or more different peptides comprises SEQ ID NO: 3.

9. The composition of claim 1, wherein the two or more different peptides comprise SEQ ID NO: 3 and SEQ ID NO: 7.

10. A kit comprising the composition of claim 1 and a labeling reagent capable of binding to an antibody that recognizes an epitope of one or more peptides in the composition.

11. The kit of claim 10, wherein the peptides in the composition are attached to or immobilized on a solid support optionally through a metallic nanolayer.

12. The kit of claim 10, wherein the labeling reagent is an anti-human, anti-canine, or anti-feline IgG or IgM antibody conjugated to a detectable label.

13. The kit of claim 12, wherein the detectable label is an enzyme, a metallic nanoparticle, metallic nanoshell, metallic nanolayer, fluorophore, or colored latex particle.

14. The kit of claim 10, wherein the labeling reagent is protein A, protein G, and/or a protein A/G fusion protein conjugated to a detectable label.

15. The kit of claim 14, wherein the detectable label is an enzyme, a metallic nanoparticle, metallic nanoshell, metallic nanolayer, fluorophore, or colored latex particle.

16. A composition comprising a population of isolated peptides, said population comprising three or more different peptides, wherein at least one peptide in the population comprises the sequence of SEQ ID NO: 3, and wherein the population further comprises two or more different peptides selected from:
  (i) SEQ ID NO: 1 or a fragment thereof, wherein $X_9$ is an amino acid selected from the group consisting of I, P and H, $X_{17}$ is an amino acid selected from the group consisting of I, W, and Y, $X_{21}$ is an amino acid selected from the group consisting of R, D, and N, $X_{28}$ is an amino acid selected from the group consisting of E and N, and $X_{31}$ is an amino acid selected from the group consisting of L and V;
  (ii) SEQ ID NO: 2 or a fragment thereof, wherein $X_3$ is an amino acid selected from the group consisting of L, V and A, $X_7$ is an amino acid selected from the group consisting of K, N and Q, $X_{11}$ is an amino acid selected from the group consisting of R, D, and N, and $X_{15}$ is an amino acid selected from the group consisting of E, N and Q;
  (iii) SEQ ID NO: 4 or a fragment thereof, wherein X6 is an amino acid selected from the group consisting of K and Q, $X_9$ is an amino acid selected from the group consisting of F and V, $X_{12}$ is an amino acid selected from the group consisting of D and N, $X_{15}$ is an amino acid selected from the group consisting of E and Q, $X_{18}$ is an amino acid selected from the group consisting of S and Q, $X_{21}$ is an amino acid selected from the group consisting of F and W, $X_{24}$ is an amino acid selected from the group consisting of I and V, and $X_{27}$ is an amino acid selected from the group consisting of Q and D;
  (iv) SEQ ID NO: 5 or a fragment thereof, wherein $X_2$ is an amino acid selected from the group consisting of I and V, $X_{10}$ is an amino acid selected from the group consisting of S and Y, and $X_{23}$ is an amino acid selected from the group consisting of E and N;
  (v) SEQ ID NO: 6 or a fragment thereof;
  (vi) SEQ ID NO: 7 or a fragment thereof, wherein $X_5$ is an amino acid selected from the group consisting of S and Q, $X_9$ is an amino acid selected from the group consisting of F and Y, $X_{13}$ is an amino acid selected from the group consisting of R and H, $X_{16}$ is an amino acid selected from the group consisting of W and Y, $X_{18}$ is an amino acid selected from the group consisting of S and Q, $X_{22}$ is an amino acid selected from the group consisting of K and H, and $X_{27}$ is an amino acid selected from the group consisting of N and D;
  (vii) SEQ ID NO: 8 or a fragment thereof, wherein $X_{10}$ is an amino acid selected from the group consisting of V, L and I, and $X_{11}$ is an amino acid selected from the group consisting of A and L; and
  (viii) SEQ ID NO: 9 or a fragment thereof, wherein $X_5$ is an amino acid selected from the group consisting of V and A, $X_7$ is an amino acid selected from the group consisting of G, I and H, $X_{11}$ is an amino acid selected from the group consisting of E, N, and Q, $X_{21}$ is an amino acid selected from the group consisting of R, D, and N, $X_{25}$ is an amino acid selected from the group consisting of Q, D, and E, $X_{28}$ is an amino acid selected from the group consisting of E and N, and $X_{31}$ is an amino acid selected from the group consisting of L and V.

17. A composition comprising a population of isolated peptides, said population comprising three or more different peptides, wherein at least one peptide in the population comprises the sequence of SEQ ID NO: 7, and wherein the population further comprises two or more different peptides selected from:
  (i) SEQ ID NO: 1 or a fragment thereof, wherein $X_9$ is an amino acid selected from the group consisting of I, P and H, $X_{17}$ is an amino acid selected from the group consisting of I, W, and Y, $X_{21}$ is an amino acid selected from the group consisting of R, D, and N, $X_{28}$ is an amino acid selected from the group consisting of E and N, and $X_{31}$ is an amino acid selected from the group consisting of L and V;
  (ii) SEQ ID NO: 2 or a fragment thereof, wherein $X_3$ is an amino acid selected from the group consisting of L, V and A, $X_7$ is an amino acid selected from the group consisting of K, N and Q, $X_{11}$ is an amino acid selected from the group consisting of R, D, and N, and $X_{15}$ is an amino acid selected from the group consisting of E, N and Q;
  (iii) SEQ ID NO: 3 or a fragment thereof, wherein $X_5$ is an amino acid selected from the group consisting of V and A, $X_7$ is an amino acid selected from the group consisting of G, I and H, $X_{11}$ is an amino acid selected from the group consisting of E, N, and Q, $X_{18}$ is an amino acid selected from the group consisting of D and N, $X_{21}$ is an amino acid selected from the group consisting of R, D, and N, $X_{25}$ is an amino acid selected from the group consisting of Q, D, and E, $X_{28}$ is an amino acid selected from the group consisting of E and N, $X_{31}$ is an amino acid selected from the group consisting of L and V, $X_{45}$ is an amino acid selected from the group consisting of K and Q, $X_{48}$ is an amino acid selected from the group consisting of F and V, $X_{51}$ is an amino acid selected from the group consisting of D and N, $X_{54}$ is an amino acid selected from the group consisting of E and Q, $X_{57}$ is an amino acid selected from the group consisting of S and Q, $X_{60}$ is an amino acid selected from the group consisting of F and W, $X_{63}$ is an amino acid selected from the group consisting of I and V, and $X_{66}$ is an amino acid selected from the group consisting of Q and D;
  (iv) SEQ ID NO: 4 or a fragment thereof, wherein $X_6$ is an amino acid selected from the group consisting of K and Q, $X_9$ is an amino acid selected from the group consisting of F and V, $X_{12}$ is an amino acid selected from the group consisting of D and N, $X_{15}$ is an amino acid selected from the group consisting of E and Q, $X_{18}$ is an amino acid selected from the group consisting of S and Q, $X_{21}$ is an amino acid selected from the group consisting of F and W, $X_{24}$ is an amino acid selected from the group consisting of I and V, and $X_{27}$ is an amino acid selected from the group consisting of Q and D;

(v) SEQ ID NO: 5 or a fragment thereof, wherein $X_2$ is an amino acid selected from the group consisting of I and V, $X_{10}$ is an amino acid selected from the group consisting of S and Y, and $X_{23}$ is an amino acid selected from the group consisting of E and N;
(vi) SEQ ID NO: 6 or a fragment thereof;
(vii) SEQ ID NO: 8 or a fragment thereof, wherein $X_{10}$ is an amino acid selected from the group consisting of V, L and I, and $X_{11}$ is an amino acid selected from the group consisting of A and L; and
(viii) SEQ ID NO: 9 or a fragment thereof, wherein $X_5$ is an amino acid selected from the group consisting of V and A, $X_7$ is an amino acid selected from the group consisting of G, I and H, $X_{11}$ is an amino acid selected from the group consisting of E, N, and Q, $X_{21}$ is an amino acid selected from the group consisting of R, D, and N, $X_{25}$ is an amino acid selected from the group consisting of Q, D, and E, $X_{28}$ is an amino acid selected from the group consisting of E and N, and $X_{31}$ is an amino acid selected from the group consisting of L and V.

\* \* \* \* \*